United States Patent
Watts et al.

(10) Patent No.: US 11,167,038 B2
(45) Date of Patent: Nov. 9, 2021

(54) METHODS FOR IMPROVING SAFETY OF BLOOD-BRAIN BARRIER TRANSPORT

(71) Applicant: Genentech, Inc., South San Francisco, CA (US)

(72) Inventors: Ryan Jefferson Watts, South San Francisco, CA (US); Joy Yu Zuchero, South San Francisco, CA (US); Jessica Couch, South San Francisco, CA (US); Mark Dennis, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 53 days.

(21) Appl. No.: 16/033,489

(22) Filed: Jul. 12, 2018

(65) Prior Publication Data

US 2019/0030160 A1  Jan. 31, 2019

Related U.S. Application Data

(63) Continuation of application No. 14/761,895, filed as application No. PCT/US2013/041860 on May 20, 2013, now abandoned.

(60) Provisional application No. 61/763,915, filed on Feb. 12, 2013, provisional application No. 61/698,495, filed on Sep. 7, 2012, provisional application No. 61/649,878, filed on May 21, 2012.

(51) Int. Cl.
| | | |
|---|---|---|
| *C07K 16/28* | (2006.01) | |
| *A61K 47/68* | (2017.01) | |
| *A61K 35/18* | (2015.01) | |
| *C07K 16/46* | (2006.01) | |
| *C07K 16/44* | (2006.01) | |
| *A61K 39/395* | (2006.01) | |
| *C07K 16/40* | (2006.01) | |
| *A61K 39/00* | (2006.01) | |

(52) U.S. Cl.
CPC .......... *A61K 47/6849* (2017.08); *A61K 35/18* (2013.01); *A61K 39/3955* (2013.01); *A61K 39/39583* (2013.01); *A61K 47/6879* (2017.08); *C07K 16/28* (2013.01); *C07K 16/2881* (2013.01); *C07K 16/40* (2013.01); *C07K 16/44* (2013.01); *C07K 16/468* (2013.01); *A61K 2039/505* (2013.01); *A61K 2039/545* (2013.01); *C07K 2317/21* (2013.01); *C07K 2317/24* (2013.01); *C07K 2317/31* (2013.01); *C07K 2317/41* (2013.01); *C07K 2317/52* (2013.01); *C07K 2317/71* (2013.01); *C07K 2317/90* (2013.01); *C07K 2317/92* (2013.01); *C07K 2317/94* (2013.01); *C07K 2319/30* (2013.01)

(58) Field of Classification Search
CPC ............ C07K 2317/92; C07K 2317/71; C07K 2317/52; C07K 14/79; C07K 16/00; C07K 16/468; C07K 16/79; C07K 16/28; A61K 39/3955; A61K 47/6849; A61K 47/6879

See application file for complete search history.

(56) References Cited

U.S. PATENT DOCUMENTS

| | | | |
|---|---|---|---|
| 7,785,791 B2 | 8/2010 | Presta | |
| 7,862,817 B2 | 1/2011 | Adams et al. | |
| 7,923,011 B2 | 4/2011 | Adams et al. | |
| 9,611,323 B2 | 4/2017 | Dennis et al. | |

FOREIGN PATENT DOCUMENTS

| | | |
|---|---|---|
| CN | 101245107 B | 10/2010 |
| WO | 0042072 A2 | 7/2000 |
| WO | 0077178 A1 | 12/2000 |
| WO | 0123554 A1 | 4/2001 |
| WO | 2007044323 A2 | 4/2007 |
| WO | 2007113172 | 10/2007 |
| WO | 2012/075037 A1 | 6/2012 |

OTHER PUBLICATIONS

Couch et al., "Addressing Safety Liabilities of TfR Bispecific Antibodies That Cross the Blood-Brain Barrier" Science Translational Medicine 5(183):14 pages (2013).
Crepin et al., "Development of Human Single-Chain Antibodies to the Transferrin Receptor that Effectively Antagonize the Growth of Leukemias and Lymphomas"Cancer Research 70(13):5497-5506 (2010).
International Search Report for PCT Application No. PCT/US2013/041860, 9 pgs. (dated Nov. 25, 2013).
Laskey et al., "Evidence that Transferrin Supports Cell Proliferation by Supplying Iron for DNA Synthesis" Experimental Cell Research 176:87-95 (1988).
Ng et al., "An anti-transferrin receptor-avidin fusion protein exhibits both strong proapoptotic activity and the ability to deliver various molecules into cancer cells" PNAS 99(16):10706-10711 (2002).
Paul et al., "Therapeutic Antibodies for Brain Disorders" Science Translational Medicine 3(84):5 pages (2011).
Tefferi et al., "Essential thrombocythemia, polycythemia vera, and myelofibrosis: Current management and the prospect of targeted therapy" Am. J. Hematol. 83:491-497 (2008).
Vannucchi et al., "Treatment options for essential thrombocythemia and polycythemia vera" Expert Rev. Hematol. 2(1):41-55 (2009).

(Continued)

*Primary Examiner* — Robert C Hayes
(74) *Attorney, Agent, or Firm* — McNeill Baur PLLC

(57) ABSTRACT

The present invention relates to compositions and methods for improving the safety of blood-brain barrier receptor-mediated blood-brain barrier transport.

16 Claims, 27 Drawing Sheets

Specification includes a Sequence Listing.

(56) References Cited

OTHER PUBLICATIONS

White et al., "Combinations of Anti-Transferrin Receptor Monoclonal Antibodies Inhibit Human Tumor Cell Growth in Vitro and in Vivo: Evidence for Synergistic Antiproliferartive Effects'" Cancer Research 50:6295-6301 (1990).
Written Opinion of the International Searching Authority for PCT Application No. PCT/US2013/041860, 15 pgs. (dated Nov. 25, 2013).
Yu et al., "Boosting Brain Uptake of a Therapeutic Antibody by Reducing Its Affinity for a Transcytosis Target" Science Translational Medicine 3(84):8 pages (2011).
Schmidt et al., "Control of Erythroid Differentiation: Possible Role of the Transferrin Cycle," Cell (46), pp. 41-51 (1986).
Schmidt et al., "Identification and characterization of the chicken transferrin receptor," Biochem J., vol. (232), pp. 735-741 (1985).
Adolfsson, et al. "An Effector-Reduced Anti-B-Amyloid (AB) Antibody with Unique AB Binding Properties Promotes Neuroprotection and Glial Engulfment of AB," The Journal of Neuroscience, 32(28A); pp. 9677-9689 (2012).
Al-Ejeh et al., "In vivoTargeting of DeadTumor Cells in aMurineTumorModel Using a Monoclonal Antibody Specific for the La Autoantigen," Clin Cancer Res 13(18 Supple), pp. 5519s-5527s (2007).
Atwal et al., "A Therapeutic Antibody Targeting BACE1 Inhibits Amyloid-B Production in Vivo," Sci Transl Med 3, 3(84), pp. 1- 12 (2011).
Boado et al., "Pharmacokinetics and Brain Uptake of a Genetically Engineered Bifunctional Fusion Antibody Targeting the Mouse Transferrin Receptor" Molecular Pharmaceutics 7(1):237-244 (2009).
File History of U.S. Appl. No. 14/761,895, 35 U.S.C. § 371(c) date Jul. 17, 2015.
Jackowski et al., "Laser-assisted flexible endoscopic fenestration of giant cyst of the septum pellucidum" British Journal of Neurosurgery 9(4):303-317 (1995).
Kabat et al., Sequences of Proteins of Immunological Interest, 5th Ed. Public Health Service, National Institutes of Health 11 pages (1991), Table of Contents Only.
Tao et al., "The Differential Ability of Human IgG1 and IgG4 to Activate Complement Is Determined by the COOH-terminal Sequence of the Ch2 Domain," J. Exp. Med. (173), pp. 1025-1028 (1991).
Van Der Zee et al., "Inhibition of Complement Activation by IgG4 Antibodies," Clin. Exp. Immunol. (64), pp. 415-422 (1986).
Vidarte et al., "Serine-132 is the C3 Covalent Attachment Point on the CH1 Domain of Human IgG1," J. Biol. Chem. 276(41): 38217-38223 (2001).
Yu et al., Boosting Brain Uptake of a Therapeutics Antibody by Reducing Its Affinity for a Transcytosis Target, Sci. Transl. Med. (3)(84), p. 84ra44 (2011).

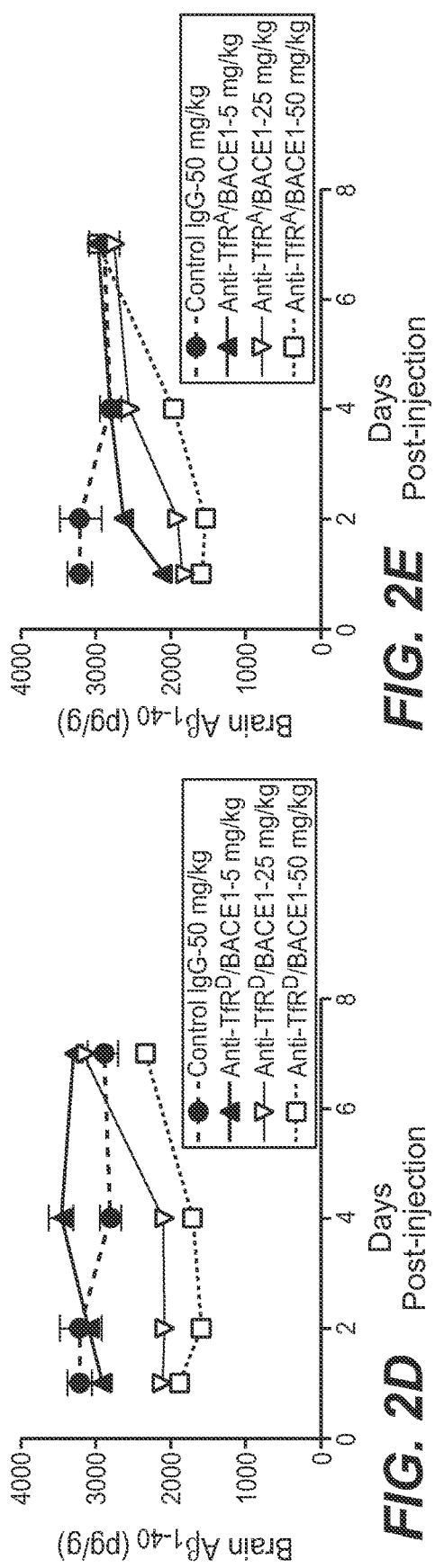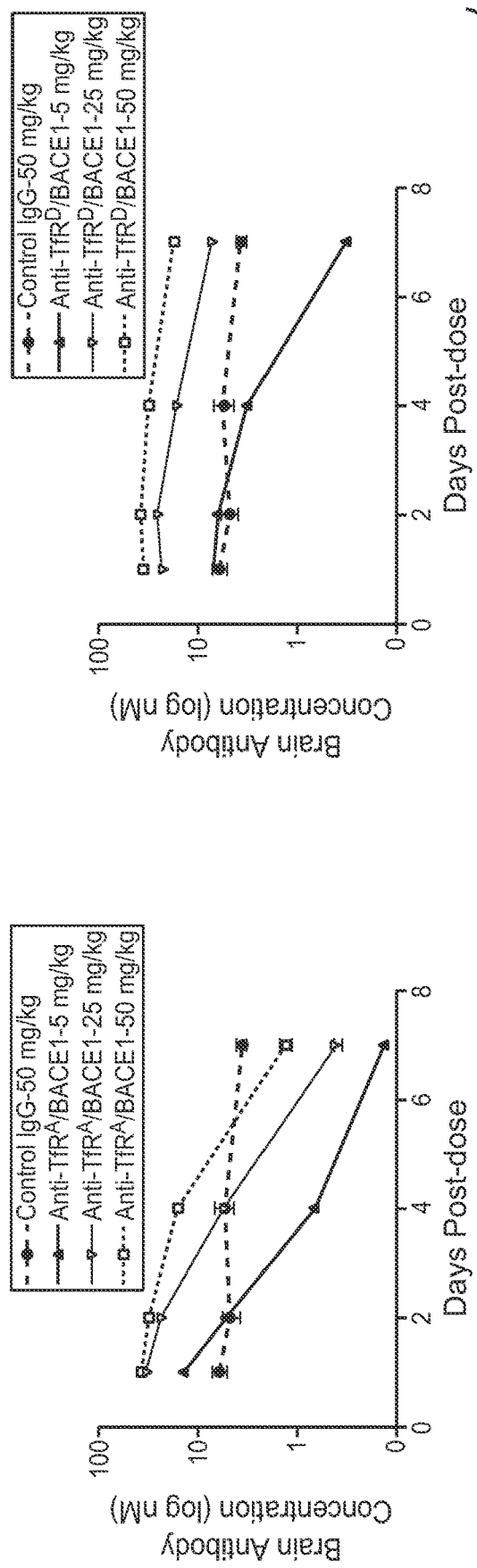
FIG. 2D
FIG. 2E
FIG. 2F

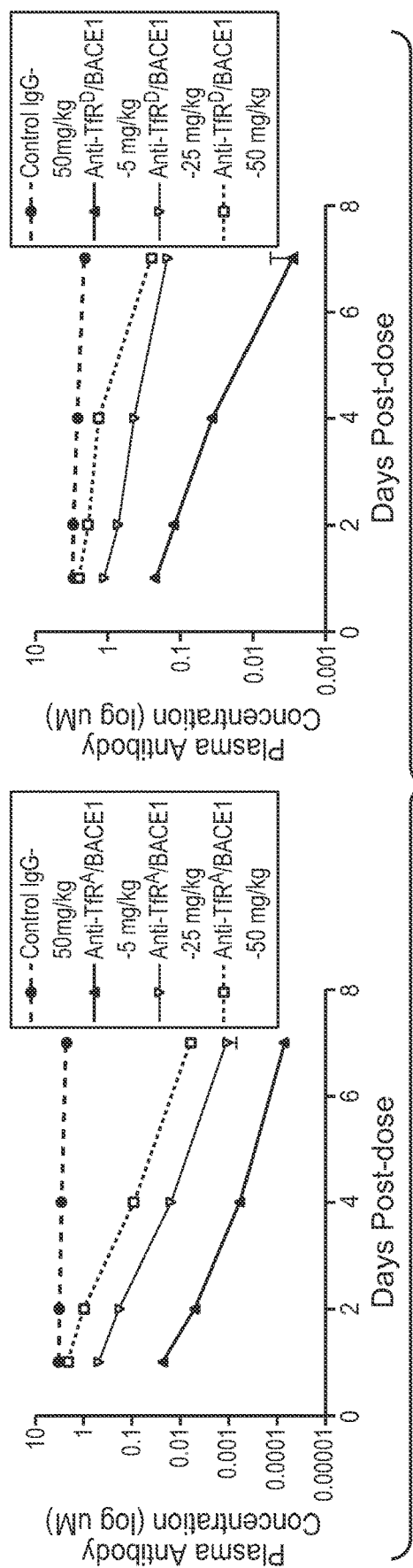
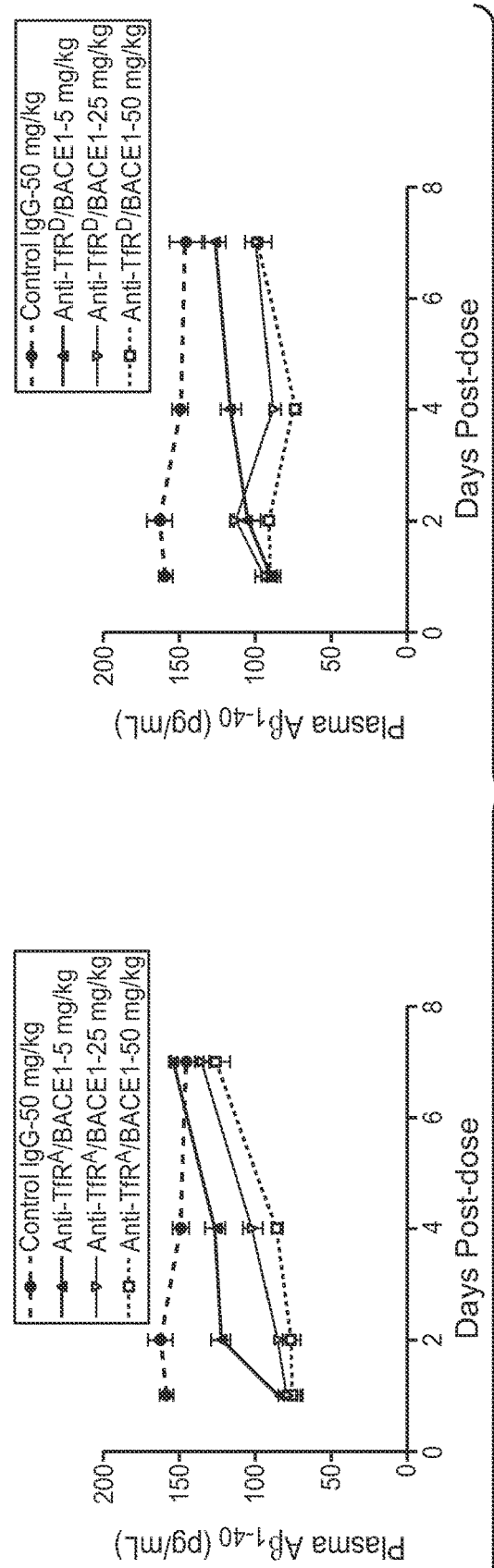
FIG. 2G
FIG. 2H

FIG. 15A

| Kabat# | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | A | B | C | D | E | F | 28 | 29 | 30 | 31 | 32 | 33 | 34 | 35 | 36 | 37 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | | | | | | | | | | | | | | | | | | | Kabat - CDR L1 | | | | | | | | | | | | Contact - CDR L1 | | | | | | |
| | | | | | | | | | | | | | | | | | | | | | | | | | | | Chothia - CDR L1 | | | | | | | | | | | | | | | |
| YW412.8    | D | I | Q | M | T | Q | S | P | S | S | L | S | A | S | V | G | D | R | V | T | I | T | C | R | A | S | Q | | | | D | V | S | T | A | V | A | W | Y | Q |
| YW412.8.31 | D | I | Q | M | T | Q | S | P | S | S | L | S | A | S | V | G | D | R | V | T | I | T | C | R | A | S | Q | | | | | D | V | S | T | A | V | A | W | Y | Q |
| YW412.8.30 | D | I | Q | M | T | Q | S | P | S | S | L | S | A | S | V | G | D | R | V | T | I | T | C | R | A | S | Q | | | | | D | | V | V | A | N | S | L | A | W | Y | Q |
| YW412.8.2  | D | I | Q | M | T | Q | S | P | S | S | L | S | A | S | V | G | D | R | V | T | I | T | C | R | A | S | Q | | | | | D | V | S | T | A | V | A | W | Y | Q |
| YW412.8.29 | D | I | Q | M | T | Q | S | P | S | S | L | S | A | S | V | G | D | R | V | T | I | T | C | R | A | S | Q | | | | | D | V | S | T | A | V | A | W | Y | Q |
| YW412.8.51 | D | I | Q | M | T | Q | S | P | S | S | L | S | A | S | V | G | D | R | V | T | I | T | C | R | A | S | Q | | | | | D | V | S | T | A | V | A | W | Y | Q |

| Kabat# | 38 | 39 | 40 | 41 | 42 | 43 | 44 | 45 | 46 | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | | | | Contact - CDR L2 | | | Kabat - CDR L2 | | | | | | | | | | | | | | | | | | | | | | | | | | | | | | |
| | | | | | | | | | | | | | Chothia - CDR L2 | | | | | | | | | | | | | | | | | | | | | | | | | | | | | | |
| YW412.8    | Q | K | P | G | K | A | P | K | L | L | I | Y | S | A | S | F | L | Y | S | G | V | P | S | R | F | S | G | S | G | S | G | T | D | F | T | L | T | I | S | S | L | Q | P |
| YW412.8.31 | Q | K | P | G | K | A | P | K | L | L | I | Y | S | A | S | F | L | Y | S | G | V | P | S | R | F | S | G | S | G | S | G | T | D | F | T | L | T | I | S | S | L | Q | P |
| YW412.8.30 | Q | K | P | G | K | A | P | K | L | L | I | Y | S | A | S | F | L | Y | S | G | V | P | S | R | F | S | G | S | G | S | G | T | D | F | T | L | T | I | S | S | L | Q | P |
| YW412.8.2  | Q | K | P | G | K | A | P | K | L | L | I | Y | S | A | S | F | L | Y | S | G | V | P | S | R | F | S | G | S | G | S | G | T | D | F | T | L | T | I | S | S | L | Q | P |
| YW412.8.29 | Q | K | P | G | K | A | P | K | L | L | I | Y | L | A | S | E | L | Y | S | G | V | P | S | R | F | S | G | S | G | S | G | T | D | F | T | L | T | I | S | S | L | Q | P |
| YW412.8.51 | Q | K | P | G | K | A | P | K | L | L | I | Y | S | A | S | F | L | Y | S | G | V | P | S | R | F | S | G | S | G | S | G | T | D | F | T | L | T | I | S | S | L | Q | P |

| Kabat# | 81 | 82 | 83 | 84 | 85 | 86 | 87 | 88 | 89 | 90 | 91 | 92 | 93 | 94 | 95 | 96 | 97 | 98 | 99 | 100 | 101 | 102 | 103 | 104 | 105 | 106 | 107 | 108 | |
|---|---|---|---|---|---|---|---|---|---|---|---|---|---|---|---|---|---|---|---|---|---|---|---|---|---|---|---|---|---|
| | | | | | | | | | | Kabat - CDR L3 | | | | | | | | | | | | | | | | | | | |
| | | | | | | | | | | Chothia - CDR L3 | | | | | | | | | | | | | | | | | | | |
| | | | | | | | | | | Contact - CDR L3 | | | | | | | | | | | | | | | | | | | |
| YW412.8    | E | D | F | A | T | Y | Y | C | Q | Q | S | Y | T | T | P | P | T | F | G | Q | G | T | K | V | E | I | K | R | SEQ ID NO: 1 |
| YW412.8.31 | E | D | F | A | T | Y | Y | C | Q | Q | F | P | T | V | L | P | T | F | G | Q | G | T | K | V | E | I | K | R | SEQ ID NO: 2 |
| YW412.8.30 | E | D | F | A | T | Y | Y | C | Q | Q | G | Y | N | D | P | P | T | F | G | Q | G | T | K | V | E | I | K | R | SEQ ID NO: 3 |
| YW412.8.2  | E | D | F | A | T | Y | Y | C | Q | Q | S | T | D | P | P | T | F | G | Q | G | T | K | V | E | I | K | R | | SEQ ID NO: 4 |
| YW412.8.29 | E | D | F | A | T | Y | Y | C | Q | Q | D | A | T | S | P | P | T | F | G | Q | G | T | K | V | E | I | K | R | SEQ ID NO: 5 |
| YW412.8.51 | E | D | F | A | T | Y | Y | C | Q | Q | V | A | T | D | P | P | T | F | G | Q | G | T | K | V | E | I | K | R | SEQ ID NO: 6 |

FIG. 15B

| Kabat# | | | | | | | | | | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | A | B | C | D | E | F | 28 | 29 | 30 | 31 | 32 | 33 | 34 | 35 | 36 | 37 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | | | | | | | | | | | | | | | | | | | | | | | | | | | | Kabat - CDR L1 | | | | | | | | | | | | | | | Contact - CDR L1 |
| | | | | | | | | | | | | | | | | | | | | | | | | | | | | | | | | | | Chothia - CDR L1 | | | | | | | | | | | | | | | |
| Fab12 | | | | | | | | | | D | I | Q | M | T | Q | S | P | S | S | L | S | A | S | V | G | D | R | V | T | I | T | C | R | A | S | Q | | | | | | S | V | S | S | A | V | A | W | Y | Q |
| LC6 IgG | | | | | | | | | | D | I | Q | M | T | Q | S | P | S | S | L | S | A | S | V | G | D | R | V | T | I | T | C | R | A | S | Q | | | | | | S | V | S | S | A | V | A | W | Y | Q |
| LC9 IgG | | | | | | | | | | D | I | Q | M | T | Q | S | P | S | S | L | S | A | S | V | G | D | R | V | T | I | T | C | R | A | S | Q | | | | | | S | V | S | S | A | V | A | W | Y | Q |
| LC10 IgG | | | | | | | | | | D | I | Q | M | T | Q | S | P | S | S | L | S | A | S | V | G | D | R | V | T | I | T | C | R | A | S | Q | | | | | | S | V | S | S | A | V | A | W | Y | Q |

| Kabat# | 38 | 39 | 40 | 41 | 42 | 43 | 44 | 45 | 46 | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | | | | | Kabat - CDR L2 | | | | | | | | | | | | | | | | | | | | | | | | | | | | | | | | |
| | | | | | | | | | | | Chothia - CDR L2 | | | | | | | | | | | | | | | | | | | | | | | | | | | | | | | | |
| | | | | | | | | | | Contact - CDR L2 | | | | | | | | | | | | | | | | | | | | | | | | | | | | | | | | | |
| Fab12 | Q | K | P | G | K | A | P | K | L | L | I | Y | S | A | S | S | L | Y | S | G | V | P | S | R | F | S | G | S | G | S | G | T | D | F | T | L | T | I | S | S | L | Q | P |
| LC6 IgG | Q | K | P | G | K | A | P | K | L | L | I | W | A | S | S | L | Y | S | G | V | P | S | R | F | S | G | S | G | S | G | T | D | F | T | L | T | I | S | S | L | Q | P |
| LC9 IgG | Q | K | P | G | K | A | P | K | L | L | I | W | Y | A | S | S | L | Y | S | G | V | P | S | R | F | S | G | S | G | S | G | T | D | F | T | L | T | I | S | S | L | Q | P |
| LC10 IgG | Q | K | P | G | K | A | P | K | L | L | I | W | A | S | S | L | Y | S | G | V | P | S | R | F | S | G | S | G | S | G | T | D | F | T | L | T | I | S | S | L | Q | P |

| Kabat# | 81 | 82 | 83 | 84 | 85 | 86 | 87 | 88 | 89 | 90 | 91 | 92 | 93 | 94 | 95 | 96 | 97 | 98 | 99 | 100 | 101 | 102 | 103 | 104 | 105 | 106 | 107 | 108 | |
|---|---|---|---|---|---|---|---|---|---|---|---|---|---|---|---|---|---|---|---|---|---|---|---|---|---|---|---|---|---|
| | | | | | | | | | Kabat - CDR L3 | | | | | | | | | | | | | | | | | | | | |
| | | | | | | | | | Chothia - CDR L3 | | | | | | | | | | | | | | | | | | | | |
| | | | | | | | | | Contact - CDR L3 | | | | | | | | | | | | | | | | | | | | |
| Fab12 | E | D | F | A | T | Y | Y | C | Q | Q | Y | S | Y | S | P | F | T | F | G | Q | G | T | K | V | E | I | K | R | SEQ ID NO: 9 |
| LC6 IgG | E | D | F | A | T | Y | Y | C | Q | Q | Y | S | Y | S | P | F | T | F | G | Q | G | T | K | V | E | I | K | R | SEQ ID NO: 10 |
| LC9 IgG | E | D | F | A | T | Y | Y | C | Q | Q | Y | S | Y | S | P | F | T | F | G | Q | G | T | K | V | E | I | K | R | SEQ ID NO: 11 |
| LC10 IgG | E | D | F | A | T | Y | Y | C | Q | Q | Y | S | Y | S | P | F | T | F | G | Q | G | T | K | V | E | I | K | R | SEQ ID NO: 12 |

FIG. 16A

| Kabat# | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 |
|---|---|---|---|---|---|---|---|---|---|---|---|---|---|---|---|---|---|---|---|---|---|---|---|---|---|---|---|---|---|---|---|---|---|---|---|---|---|---|---|---|
| Fab12  | E | V | Q | L | L | E | S | G | G | G | L | V | Q | P | G | G | S | L | R | L | S | C | A | A | S | G | F | N | F | Y | Y | S | S | I | H | W | V | R | Q | A |
| LC6 IgG | E | V | Q | L | V | E | S | G | G | G | L | V | Q | P | G | G | S | L | R | L | S | C | A | A | S | G | F | N | F | Y | Y | S | S | I | H | W | V | R | Q | A |
| LC9 IgG | E | V | Q | L | V | E | S | G | G | G | L | V | Q | P | G | G | S | L | R | L | S | C | A | A | S | G | F | N | F | Y | Y | S | S | I | H | W | V | R | Q | A |
| LC10 IgG | E | V | Q | L | V | E | S | G | G | G | L | V | Q | P | G | G | S | L | R | L | S | C | A | A | S | G | F | N | F | Y | Y | S | S | I | H | W | V | R | Q | A |

Chothia - CDR H1: 26–32
Kabat - CDR H1: 31–35
Contact - CDR H1: 30–35

| Kabat# | 41 | 42 | 43 | 44 | 45 | 46 | 47 | 48 | 49 | 50 | 51 | 52 | 52A | 52B | 52C | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 |
|---|---|---|---|---|---|---|---|---|---|---|---|---|---|---|---|---|---|---|---|---|---|---|---|---|---|---|---|---|---|---|---|---|---|---|---|---|---|---|---|---|---|
| Fab12 | P | G | K | G | L | E | W | V | A | S | I | S | P | | | Y | S | G | Y | T | S | Y | A | D | S | V | K | G | R | F | T | I | S | A | D | T | S | K | N | T | A |
| LC6 IgG | P | G | K | G | L | E | W | V | A | S | I | S | P | | | Y | S | G | Y | T | S | Y | A | D | S | V | K | G | R | F | T | I | S | A | D | T | S | K | N | T | A |
| LC9 IgG | P | G | K | G | L | E | W | V | A | S | I | S | P | | | Y | S | G | Y | T | S | Y | A | D | S | V | K | G | R | F | T | I | S | A | D | T | S | K | N | T | A |
| LC10 IgG | P | G | K | G | L | E | W | V | A | S | I | S | P | | | Y | S | G | Y | T | S | Y | A | D | S | V | K | G | R | F | T | I | S | A | D | T | S | K | N | T | A |

Chothia - CDR H2: 50–52
Kabat - CDR H2: 50–57
Contact - CDR H2: 47–55

| Kabat# | 79 | 80 | 81 | 82 | 82A | 82B | 82C | 83 | 84 | 85 | 86 | 87 | 88 | 89 | 90 | 91 | 92 | 93 | 94 | 95 | 96 | 97 | 98 | 99 | 100 | 100A | 100B | 100C | 100D | 100E | 100F | 100G | 100H | 101 | 102 | 103 | 104 | 105 | 106 | 107 | 108 | 109 | 110 | 111 | 112 | 113 | SEQ ID NO: |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| Fab12 | Y | L | Q | M | N | S | L | R | A | E | D | T | A | V | Y | Y | C | A | R | Q | P | T | H | Y | Y | Y | Y | A | K | G | Y | K | A | M | D | Y | W | G | Q | G | T | L | V | T | V | S | 13 |
| LC6 IgG | Y | L | Q | M | N | S | L | R | A | E | D | T | A | V | Y | Y | C | A | R | Q | P | T | H | Y | Y | Y | Y | A | K | G | Y | K | A | M | D | Y | W | G | Q | G | T | L | V | T | V | S | 13 |
| LC9 IgG | Y | L | Q | M | N | S | L | R | A | E | D | T | A | V | Y | Y | C | A | R | Q | P | T | H | Y | Y | Y | Y | A | K | G | Y | K | A | M | D | Y | W | G | Q | G | T | L | V | T | V | S | 13 |
| LC10 IgG | Y | L | Q | M | N | S | L | R | A | E | D | T | A | V | Y | Y | C | A | R | Q | P | T | H | Y | Y | Y | Y | A | K | G | Y | K | A | M | D | Y | W | G | Q | G | T | L | V | T | V | S | 13 |

Kabat - CDR H3: 95–102
Chothia - CDR H3: 95–102
Contact - CDR H3: 93–101

FIG. 16B

```
  1 EVQLVESGGG LVQPGGSLRL SCAASGFTFS SYGMSWVRQA PGKGLELVAS
 51 INSNGGSTYY PDSVKGRFTI SRDNAKNSLY LQMNSLRAED TAVYYCASGD
101 YWGQGTTVTV SSASTKGPSV FPLAPCSRST SESTAALGCL VKDYFPEPVT
151 VSWNSGALTS GVHTFPAVLQ SSGLYSLSSV VTVPSSSLGT KTYTCNVDHK
201 PSNTKVDKRV ESKYGPPCPP CPAPEFLGGP SVFLFPPKPK DTLMISRTPE
251 VTCVVVDVSQ EDPEVQFNWY VDGVEVHNAK TKPREEQFNS TYRVVSVLTV
301 LHQDWLNGKE YKCKVSNKGL PSSIEKTISK AKGQPREPQV YTLPPSQEEM
351 TKNQVSLTCL VKGFYPSDIA VEWESNGQPE NNYKTTPPVL DSDGSFFLYS
401 RLTVDKSRWQ EGNVFSCSVM HEALHNHYTQ KSLSLSLG (SEQ ID NO: 14)
```

FIG. 17A

```
  1 DIVMTQSPLS LPVTPGEPAS ISCRSSQSLV YSNGDTYLHW YLQKPGQSPQ
 51 LLIYKVSNRF SGVPDRFSGS GSGTDFTLKI SRVEAEDVGV YYCSQSTHVP
101 WTFGQGTKVE IKRTVAAPSV FIFPPSDEQL KSGTASVVCL LNNFYPREAK
151 VQWKVDNALQ SGNSQESVTE QDSKDSTYSL SSTLTLSKAD YEKHKVYACE
201 VTHQGLSSPV TKSFNRGEC (SEQ ID NO: 15)
```

FIG. 17B

SEQUENCE LISTING

```
<160> NUMBER OF SEQ ID NOS: 15

<210> SEQ ID NO 1
<211> LENGTH: 108
<212> TYPE: PRT
<213> ORGANISM: Artificial sequence
<220> FEATURE:
<223> OTHER INFORMATION: sequence is synthesized

<400> SEQUENCE: 1

Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Asp Val Ser
                20                  25                  30

Thr Ala Val Ala Trp Tyr Gln Gln Lys Pro Gly Lys Ala Pro Lys
                35                  40                  45

Leu Leu Ile Tyr Ser Ala Ser Phe Leu Tyr Ser Gly Val Pro Ser
                50                  55                  60

Arg Phe Ser Gly Ser Gly Ser Gly Thr Asp Phe Thr Leu Thr Ile
                65                  70                  75

Ser Ser Leu Gln Pro Glu Asp Phe Ala Thr Tyr Tyr Cys Gln Gln
                80                  85                  90

Ser Tyr Thr Thr Pro Pro Thr Phe Gly Gln Gly Thr Lys Val Glu
                95                  100                 105

Ile Lys Arg
```

```
<210> SEQ ID NO 2
<211> LENGTH: 108
<212> TYPE: PRT
<213> ORGANISM: Artificial sequence
<220> FEATURE:
<223> OTHER INFORMATION: sequence is synthesized

<400> SEQUENCE: 2

Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Asp Val Ser
                20                  25                  30

Thr Ala Val Ala Trp Tyr Gln Gln Lys Pro Gly Lys Ala Pro Lys
            35                  40                  45

Leu Leu Ile Tyr Ser Ala Ser Phe Leu Tyr Ser Gly Val Pro Ser
        50                  55                  60

Arg Phe Ser Gly Ser Gly Ser Gly Thr Asp Phe Thr Leu Thr Ile
 65                  70                  75

Ser Ser Leu Gln Pro Glu Asp Phe Ala Thr Tyr Tyr Cys Gln Gln
                80                  85                  90

Phe Pro Thr Tyr Leu Pro Thr Phe Gly Gln Gly Thr Lys Val Glu
                95                 100                 105

Ile Lys Arg

<210> SEQ ID NO 3
<211> LENGTH: 108
<212> TYPE: PRT
<213> ORGANISM: Artificial sequence
<220> FEATURE:
<223> OTHER INFORMATION: sequence is synthesized

<400> SEQUENCE: 3

Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Asp Val Ser
                20                  25                  30

Thr Ala Val Ala Trp Tyr Gln Gln Lys Pro Gly Lys Ala Pro Lys
            35                  40                  45

Leu Leu Ile Tyr Ser Ala Ser Phe Leu Tyr Ser Gly Val Pro Ser
        50                  55                  60

Arg Phe Ser Gly Ser Gly Ser Gly Thr Asp Phe Thr Leu Thr Ile
 65                  70                  75

Ser Ser Leu Gln Pro Glu Asp Phe Ala Thr Tyr Tyr Cys Gln Gln
                80                  85                  90

Gly Tyr Asn Asp Pro Pro Thr Phe Gly Gln Gly Thr Lys Val Glu
                95                 100                 105

Ile Lys Arg

<210> SEQ ID NO 4
<211> LENGTH: 108
<212> TYPE: PRT
<213> ORGANISM: Artificial sequence
<220> FEATURE:
<223> OTHER INFORMATION: sequence is synthesized

<400> SEQUENCE: 4

Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Asp Val Ser
```

```
                    20                  25                  30

Thr Ala Val Ala Trp Tyr Gln Gln Lys Pro Gly Lys Ala Pro Lys
                35                  40                  45

Leu Leu Ile Tyr Ser Ala Ser Phe Leu Tyr Ser Gly Val Pro Ser
                50                  55                  60

Arg Phe Ser Gly Ser Gly Ser Gly Thr Asp Phe Thr Leu Thr Ile
                65                  70                  75

Ser Ser Leu Gln Pro Glu Asp Phe Ala Thr Tyr Tyr Cys Gln Gln
                80                  85                  90

Ser Ser Thr Asp Pro Thr Thr Phe Gly Gln Gly Thr Lys Val Glu
                95                 100                 105

Ile Lys Arg

<210> SEQ ID NO 5
<211> LENGTH: 108
<212> TYPE: PRT
<213> ORGANISM: Artificial sequence
<220> FEATURE:
<223> OTHER INFORMATION: sequence is synthesized

<400> SEQUENCE: 5

Asp Ile Gln Met Thr Gln Ser Pro Ser Ser Leu Ser Ala Ser Val
  1               5                  10                  15

Gly Asp Arg Val Thr Ile Thr Cys Arg Ala Ser Gln Val Val Ala
                20                  25                  30

Asn Ser Leu Ala Trp Tyr Gln Gln Lys Pro Gly Lys Ala Pro Lys
                35                  40                  45

Leu Leu Ile Tyr Leu Ala Ser Phe Leu Tyr Ser Gly Val Pro Ser
                50                  55                  60

Arg Phe Ser Gly Ser Gly Ser Gly Thr Asp Phe Thr Leu Thr Ile
                65                  70                  75

Ser Ser Leu Gln Pro Glu Asp Phe Ala Thr Tyr Tyr Cys Gln Gln
                80                  85                  90

Asp Ala Thr Ser Pro Pro Thr Phe Gly Gln Gly Thr Lys Val Glu
                95                 100                 105

Ile Lys Arg

<210> SEQ ID NO 6
<211> LENGTH: 108
<212> TYPE: PRT
<213> ORGANISM: Artificial sequence
<220> FEATURE:
<223> OTHER INFORMATION: sequence is synthesized

<400> SEQUENCE: 6

Asp Ile Gln Met Thr Gln Ser Pro Ser Ser Leu Ser Ala Ser Val
  1               5                  10                  15

Gly Asp Arg Val Thr Ile Thr Cys Arg Ala Ser Gln Asp Val Ser
                20                  25                  30

Thr Ala Val Ala Trp Tyr Gln Gln Lys Pro Gly Lys Ala Pro Lys
                35                  40                  45

Leu Leu Ile Tyr Ser Ala Ser Phe Leu Tyr Ser Gly Val Pro Ser
                50                  55                  60

Arg Phe Ser Gly Ser Gly Ser Gly Thr Asp Phe Thr Leu Thr Ile
                65                  70                  75

Ser Ser Leu Gln Pro Glu Asp Phe Ala Thr Tyr Tyr Cys Gln Gln
                80                  85                  90
```

Tyr Ala Thr Asp Pro Pro Thr Phe Gly Gln Gly Thr Lys Val Glu
                95                 100                 105

Ile Lys Arg

<210> SEQ ID NO 7
<211> LENGTH: 119
<212> TYPE: PRT
<213> ORGANISM: Artificial sequence
<220> FEATURE:
<223> OTHER INFORMATION: sequence is synthesized

<400> SEQUENCE: 7

Glu Val Gln Leu Val Glu Ser Gly Gly Gly Leu Val Gln Pro Gly
  1               5                  10                  15

Gly Ser Leu Arg Leu Ser Cys Ala Ala Ser Gly Phe Thr Phe Ser
                 20                  25                  30

Gly Tyr Ala Ile His Trp Val Arg Gln Ala Pro Gly Lys Gly Leu
                 35                  40                  45

Glu Trp Val Gly Trp Ile Ser Pro Ala Gly Gly Ser Thr Asp Tyr
                 50                  55                  60

Ala Asp Ser Val Lys Gly Arg Phe Thr Ile Ser Ala Asp Thr Ser
                 65                  70                  75

Lys Asn Thr Ala Tyr Leu Gln Met Asn Ser Leu Arg Ala Glu Asp
                 80                  85                  90

Thr Ala Val Tyr Tyr Cys Ala Arg Gly Pro Phe Ser Pro Trp Val
                 95                 100                 105

Met Asp Tyr Trp Gly Gln Gly Thr Leu Val Thr Val Ser Ser
                110                 115

<210> SEQ ID NO 8
<211> LENGTH: 119
<212> TYPE: PRT
<213> ORGANISM: Artificial sequence
<220> FEATURE:
<223> OTHER INFORMATION: sequence is synthesized

<400> SEQUENCE: 8

Glu Val Gln Leu Val Glu Ser Gly Gly Gly Leu Val Gln Pro Gly
  1               5                  10                  15

Gly Ser Leu Arg Leu Ser Cys Ala Ala Ser Gly Phe Thr Phe Leu
                 20                  25                  30

Gly Tyr Gly Ile His Trp Val Arg Gln Ala Pro Gly Lys Gly Leu
                 35                  40                  45

Glu Trp Val Gly Trp Ile Ser Pro Ala Gly Gly Ser Thr Asp Tyr
                 50                  55                  60

Ala Asp Ser Val Lys Gly Arg Phe Thr Ile Ser Ala Asp Thr Ser
                 65                  70                  75

Lys Asn Thr Ala Tyr Leu Gln Met Asn Ser Leu Arg Ala Glu Asp
                 80                  85                  90

Thr Ala Val Tyr Tyr Cys Ala Arg Gly Pro Phe Ser Pro Trp Val
                 95                 100                 105

Met Asp Tyr Trp Gly Gln Gly Thr Leu Val Thr Val Ser Ser
                110                 115

<210> SEQ ID NO 9
<211> LENGTH: 108
<212> TYPE: PRT
<213> ORGANISM: Artificial sequence

```
<220> FEATURE:
<223> OTHER INFORMATION: sequence is synthesized

<400> SEQUENCE: 9
```

Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Ser Val Ser
                20                  25                  30

Ser Ala Val Ala Trp Tyr Gln Gln Lys Pro Gly Lys Ala Pro Lys
                35                  40                  45

Leu Leu Ile Tyr Ser Ala Ser Ser Leu Tyr Ser Gly Val Pro Ser
                50                  55                  60

Arg Phe Ser Gly Ser Gly Ser Gly Thr Asp Phe Thr Leu Thr Ile
                65                  70                  75

Ser Ser Leu Gln Pro Glu Asp Phe Ala Thr Tyr Tyr Cys Gln Gln
                80                  85                  90

Tyr Ser Tyr Ser Pro Phe Thr Phe Gly Gln Gly Thr Lys Val Glu
                95                 100                 105

Ile Lys Arg

```
<210> SEQ ID NO 10
<211> LENGTH: 108
<212> TYPE: PRT
<213> ORGANISM: Artificial sequence
<220> FEATURE:
<223> OTHER INFORMATION: sequence is synthesized

<400> SEQUENCE: 10
```

Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Ser Val Ser
                20                  25                  30

Ser Ala Val Ala Trp Tyr Gln Gln Lys Pro Gly Lys Ala Pro Lys
                35                  40                  45

Leu Leu Ile Ser Trp Ala Ser Trp Leu Tyr Ser Gly Val Pro Ser
                50                  55                  60

Arg Phe Ser Gly Ser Gly Ser Gly Thr Asp Phe Thr Leu Thr Ile
                65                  70                  75

Ser Ser Leu Gln Pro Glu Asp Phe Ala Thr Tyr Tyr Cys Gln Gln
                80                  85                  90

Tyr Ser Tyr Ser Pro Phe Thr Phe Gly Gln Gly Thr Lys Val Glu
                95                 100                 105

Ile Lys Arg

```
<210> SEQ ID NO 11
<211> LENGTH: 108
<212> TYPE: PRT
<213> ORGANISM: Artificial sequence
<220> FEATURE:
<223> OTHER INFORMATION: sequence is synthesized

<400> SEQUENCE: 11
```

Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Ser Val Ser
                20                  25                  30

Ser Ala Val Ala Trp Tyr Gln Gln Lys Pro Gly Lys Ala Pro Lys
                35                  40                  45

```
Leu Leu Ile Trp Tyr Ala Ser Trp Leu Tyr Ser Gly Val Pro Ser
            50                  55                  60

Arg Phe Ser Gly Ser Gly Ser Gly Thr Asp Phe Thr Leu Thr Ile
            65                  70                  75

Ser Ser Leu Gln Pro Glu Asp Phe Ala Thr Tyr Tyr Cys Gln Gln
            80                  85                  90

Tyr Ser Tyr Ser Pro Phe Thr Phe Gly Gln Gly Thr Lys Val Glu
            95                 100                 105

Ile Lys Arg

<210> SEQ ID NO 12
<211> LENGTH: 108
<212> TYPE: PRT
<213> ORGANISM: Artificial sequence
<220> FEATURE:
<223> OTHER INFORMATION: sequence is synthesized

<400> SEQUENCE: 12

Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Ser Val Ser
            20                  25                  30

Ser Ala Val Ala Trp Tyr Gln Gln Lys Pro Gly Lys Ala Pro Lys
            35                  40                  45

Leu Leu Ile Trp Trp Ala Ser Ser Leu Tyr Ser Gly Val Pro Ser
            50                  55                  60

Arg Phe Ser Gly Ser Gly Ser Gly Thr Asp Phe Thr Leu Thr Ile
            65                  70                  75

Ser Ser Leu Gln Pro Glu Asp Phe Ala Thr Tyr Tyr Cys Gln Gln
            80                  85                  90

Tyr Ser Tyr Ser Pro Phe Thr Phe Gly Gln Gly Thr Lys Val Glu
            95                 100                 105

Ile Lys Arg

<210> SEQ ID NO 13
<211> LENGTH: 126
<212> TYPE: PRT
<213> ORGANISM: Artificial sequence
<220> FEATURE:
<223> OTHER INFORMATION: sequence is synthesized

<400> SEQUENCE: 13

Glu Val Gln Leu Val Glu Ser Gly Gly Gly Leu Val Gln Pro Gly
 1               5                  10                  15

Gly Ser Leu Arg Leu Ser Cys Ala Ala Ser Gly Phe Asn Phe Tyr
            20                  25                  30

Tyr Ser Ser Ile His Trp Val Arg Gln Ala Pro Gly Lys Gly Leu
            35                  40                  45

Glu Trp Val Ala Ser Ile Ser Pro Tyr Ser Gly Tyr Thr Ser Tyr
            50                  55                  60

Ala Asp Ser Val Lys Gly Arg Phe Thr Ile Ser Ala Asp Thr Ser
            65                  70                  75

Lys Asn Thr Ala Tyr Leu Gln Met Asn Ser Leu Arg Ala Glu Asp
            80                  85                  90

Thr Ala Val Tyr Tyr Cys Ala Arg Gln Pro Thr His Tyr Tyr Tyr
            95                 100                 105
```

Tyr Ala Lys Gly Tyr Lys Ala Met Asp Tyr Trp Gly Gln Gly Thr
                    110                 115                 120

Leu Val Thr Val Ser Ser
                125

<210> SEQ ID NO 14
<211> LENGTH: 438
<212> TYPE: PRT
<213> ORGANISM: Artificial sequence
<220> FEATURE:
<223> OTHER INFORMATION: sequence is synthesized

<400> SEQUENCE: 14

Glu Val Gln Leu Val Glu Ser Gly Gly Gly Leu Val Gln Pro Gly
 1               5                  10                  15

Gly Ser Leu Arg Leu Ser Cys Ala Ala Ser Gly Phe Thr Phe Ser
                20                  25                  30

Ser Tyr Gly Met Ser Trp Val Arg Gln Ala Pro Gly Lys Gly Leu
                35                  40                  45

Glu Leu Val Ala Ser Ile Asn Ser Asn Gly Gly Ser Thr Tyr Tyr
                50                  55                  60

Pro Asp Ser Val Lys Gly Arg Phe Thr Ile Ser Arg Asp Asn Ala
                65                  70                  75

Lys Asn Ser Leu Tyr Leu Gln Met Asn Ser Leu Arg Ala Glu Asp
                80                  85                  90

Thr Ala Val Tyr Tyr Cys Ala Ser Gly Asp Tyr Trp Gly Gln Gly
                95                  100                 105

Thr Thr Val Thr Val Ser Ser Ala Ser Thr Lys Gly Pro Ser Val
                110                 115                 120

Phe Pro Leu Ala Pro Cys Ser Arg Ser Thr Ser Glu Ser Thr Ala
                125                 130                 135

Ala Leu Gly Cys Leu Val Lys Asp Tyr Phe Pro Glu Pro Val Thr
                140                 145                 150

Val Ser Trp Asn Ser Gly Ala Leu Thr Ser Gly Val His Thr Phe
                155                 160                 165

Pro Ala Val Leu Gln Ser Ser Gly Leu Tyr Ser Leu Ser Ser Val
                170                 175                 180

Val Thr Val Pro Ser Ser Ser Leu Gly Thr Lys Thr Tyr Thr Cys
                185                 190                 195

Asn Val Asp His Lys Pro Ser Asn Thr Lys Val Asp Lys Arg Val
                200                 205                 210

Glu Ser Lys Tyr Gly Pro Pro Cys Pro Pro Cys Pro Ala Pro Glu
                215                 220                 225

Phe Leu Gly Gly Pro Ser Val Phe Leu Phe Pro Pro Lys Pro Lys
                230                 235                 240

Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr
                260                 265                 270

Val Asp Gly Val Glu Val His Asn Ala Lys Thr Lys Pro Arg Glu
                275                 280                 285

Glu Gln Phe Asn Ser Thr Tyr Arg Val Val Ser Val Leu Thr Val
                290                 295                 300

Leu His Gln Asp Trp Leu Asn Gly Lys Glu Tyr Lys Cys Lys Val
                305                 310                 315

```
Ser Asn Lys Gly Leu Pro Ser Ser Ile Glu Lys Thr Ile Ser Lys
            320                 325                 330

Ala Lys Gly Gln Pro Arg Glu Pro Gln Val Tyr Thr Leu Pro Pro
            335                 340                 345

Ser Gln Glu Glu Met Thr Lys Asn Gln Val Ser Leu Thr Cys Leu
            350                 355                 360

Val Lys Gly Phe Tyr Pro Ser Asp Ile Ala Val Glu Trp Glu Ser
            365                 370                 375

Asn Gly Gln Pro Glu Asn Asn Tyr Lys Thr Thr Pro Pro Val Leu
            380                 385                 390

Asp Ser Asp Gly Ser Phe Phe Leu Tyr Ser Arg Leu Thr Val Asp
            395                 400                 405

Lys Ser Arg Trp Gln Glu Gly Asn Val Phe Ser Cys Ser Val Met
            410                 415                 420

His Glu Ala Leu His Asn His Tyr Thr Gln Lys Ser Leu Ser Leu
            425                 430                 435

Ser Leu Gly

<210> SEQ ID NO 15
<211> LENGTH: 219
<212> TYPE: PRT
<213> ORGANISM: Artificial sequence
<220> FEATURE:
<223> OTHER INFORMATION: sequence is synthesized

<400> SEQUENCE: 15

Asp Ile Val Met Thr Gln Ser Pro Leu Ser Leu Pro Val Thr Pro
  1               5                  10                  15

Gly Glu Pro Ala Ser Ile Ser Cys Arg Ser Ser Gln Ser Leu Val
             20                  25                  30

Tyr Ser Asn Gly Asp Thr Tyr Leu His Trp Tyr Leu Gln Lys Pro
             35                  40                  45

Gly Gln Ser Pro Gln Leu Leu Ile Tyr Lys Val Ser Asn Arg Phe
             50                  55                  60

Ser Gly Val Pro Asp Arg Phe Ser Gly Ser Gly Ser Gly Thr Asp
             65                  70                  75

Phe Thr Leu Lys Ile Ser Arg Val Glu Ala Glu Asp Val Gly Val
             80                  85                  90

Tyr Tyr Cys Ser Gln Ser Thr His Val Pro Trp Thr Phe Gly Gln
             95                 100                 105

Gly Thr Lys Val Glu Ile Lys Arg Thr Val Ala Ala Pro Ser Val
            110                 115                 120

Phe Ile Phe Pro Pro Ser Asp Glu Gln Leu Lys Ser Gly Thr Ala
            125                 130                 135

Ser Val Val Cys Leu Leu Asn Asn Phe Tyr Pro Arg Glu Ala Lys
            140                 145                 150

Val Gln Trp Lys Val Asp Asn Ala Leu Gln Ser Gly Asn Ser Gln
            155                 160                 165

Glu Ser Val Thr Glu Gln Asp Ser Lys Asp Ser Thr Tyr Ser Leu
            170                 175                 180
```

-continued

```
Ser Ser Thr Leu Thr Leu Ser Lys Ala Asp Tyr Glu Lys His Lys
            185                 190                 195

Val Tyr Ala Cys Glu Val Thr His Gln Gly Leu Ser Ser Pro Val
            200                 205                 210

Thr Lys Ser Phe Asn Arg Gly Glu Cys
            215
```

METHODS FOR IMPROVING SAFETY OF BLOOD-BRAIN BARRIER TRANSPORT

CROSS-REFERENCE TO RELATED APPLICATIONS

This application is a continuation of U.S. application Ser. No. 14/761,895, whose 35 U.S.C. § 371(c) date is Jul. 17, 2015, which is a national phase entry pursuant to 35 U.S.C. § 371 of International Application No. PCT/US2013/041860, filed May 20, 2013, which claims priority to U.S. Provisional Application No. 61/763,915, filed Feb. 12, 2013, U.S. Provisional Application No. 61/698,495, filed Sep. 7, 2012, and U.S. Provisional Application No. 61/649,878, filed May 21, 2012, all of which are incorporated by reference herein in their entirety for any purpose.

SEQUENCE LISTING

The instant application contains a Sequence Listing submitted via EFS-Web in ASCII format and hereby incorporated by reference in its entirety. Said Sequence Listing, created on Jul. 10, 2018, is named 2018-07-11_01146-0049-01US_SeqListing.txt, and is 19,754 bytes in size.

FIELD OF THE INVENTION

The present invention relates to compositions and methods for improving the safety of blood-brain barrier receptor-mediated blood-brain barrier transport.

BACKGROUND

Brain penetration of large molecule drugs is severely limited by the largely impermeable blood-brain barrier (BBB). Among the many strategies to overcome this obstacle is to utilize transcytosis trafficking pathways of endogenous receptors expressed at the brain capillary endothelium. Recombinant proteins such as monoclonal antibodies have been designed against these receptors to enable receptor-mediated delivery of large molecules to the brain. Strategies to maximize brain uptake while minimizing reverse transcytosis back to the blood, and to also maximize the extent of accumulation after therapeutic dosing have been addressed with the finding that antibodies with low affinity to BBB receptors offer the potential to substantially increase BBB transport and CNS retention of associated therapeutic moieties/molecules relative to typical high-affinity antibodies to such receptors (Atwal et al., Sci. Transl. Med. 3, 84ra43 (2011); Yu et al., Sci. Transl. Med. 25 May 2011: Vol. 3, Issue 84, p. 84ra44). However, the safety of administration of such antibodies and conjugates has not been fully explored.

SUMMARY

Monoclonal antibodies have vast therapeutic potential for treatment of neurological or central nervous system (CNS) diseases, but their passage into the brain is restricted by the blood-brain barrier (BBB). Past studies have shown that a very small percentage (approximately 0.1%) of an IgG circulating in the bloodstream crosses through the BBB into the CNS (Felgenhauer, Klin. Wschr. 52: 1158-1164 (1974)), where the CNS concentration of the antibody may be insufficient to permit a robust effect. It was previously found that the percentage of the antibody that distributes into the CNS could be improved by exploiting BBB receptors (ie, transferrin receptor, insulin receptor, low density lipoprotein receptor-related protein 8, glucose transporter 1 (Glut1) and the like) (see, e.g., WO9502421). For example, the anti-BBB receptor antibody can be made multispecific to target one or more desired antigens in the CNS, or one or more heterologous molecules can be coupled to the anti-BBB receptor antibody; in either case, the anti-BBB receptor antibody can assist in delivering a therapeutic molecule into the CNS across the BBB.

However, targeting a BBB receptor with a traditional specific high-affinity antibody generally resulted in limited increase in BBB transport. It was later found by Applicants that the magnitude of antibody uptake into and distribution in the CNS is inversely related to its binding affinity for the BBB receptor amongst the anti-BBB antibodies studied. For example, a low-affinity antibody to transferrin receptor (TfR) dosed at therapeutic dose levels greatly improves BBB transport and CNS retention of the anti-TfR antibody relative to a higher-affinity anti-TfR antibody, and makes it possible to more readily attain therapeutic concentrations in the CNS (Atwal et al., Sci. Transl. Med. 3, 84ra43 (2011)). Proof of such BBB transport was achieved using a bispecific antibody that binds both TfR and the amyloid precursor protein (APP) cleavage enzyme, β-secretase (BACE1). A single systemic dose of the bispecific anti-TfR/BACE1 antibody engineered using the methodology of the invention not only resulted in significant antibody uptake in brain, but also dramatically reduced levels of brain $A\beta_{1-40}$ compared to monospecific anti-BACE1 alone, suggesting that BBB penetrance affects the potency of anti-BACE1. (Atwal et al., Sci. Transl. Med. 3, 84ra43 (2011); Yu et al., Sci. Transl. Med. 3, 84ra44 (2011)).

Those data and experiments highlighted several causative mechanisms behind increasing uptake of an antibody into the CNS using a lower-affinity antibody approach. First, high affinity anti-BBB receptor (BBB-R) antibodies (e.g., anti-TfR$^A$) limit brain uptake by quickly saturating the BBB-R in the brain vasculature, thus reducing the total amount of antibody taken up into the brain and also restricting its distribution to the vasculature. Strikingly, lowering affinity for the BBB-R improves brain uptake and distribution, with a robust shift observed in localization from the vasculature to neurons and associated neuropil distributed within the CNS. Second, the lower affinity of the antibody for the BBB-R is proposed to impair the ability of the antibody to return to the vascular side of the BBB via the BBB-R from the CNS side of the membrane because the overall affinity of the antibody for the BBB-R is low and the local concentration of the antibody on the CNS side of the BBB is non-saturating due to the rapid dispersal of the antibody into the CNS compartment. Third, in vivo, and as observed for the TfR system, antibodies with less affinity for the BBB-R are not cleared from the system as efficiently as those with greater affinity for the BBB-R, and thus remain at higher circulating concentrations than their higher-affinity counterparts. This is advantageous because the circulating antibody levels of the lower-affinity antibody are sustained at therapeutic levels for a longer period of time than the higher-affinity antibody, which consequently improves uptake of antibody in brain for a longer period of time. Furthermore, this improvement in both plasma and brain exposure may reduce the frequency of dosing in the clinic, which would have potential benefit not only for patient compliance and convenience but also in lessening any potential side effects or off-target effects of the antibody and/or of a therapeutic compound coupled thereto.

The low-affinity BBB-R antibodies described in the above-referenced work were selected/engineered to avoid interference with the natural binding between transferrin and the TfR, and thus to avoid potential iron transport-related side effects. Nonetheless, upon administration of certain of these antibodies in mice, some marked side effects were observed. The mice displayed a primary response of robust depletion of reticulocyte populations accompanied by rapid onset acute clinical symptoms, as described in the Examples. Further in vitro studies using a human erythroblast cell line and primary bone marrow cells treated with anti-human TfR antibodies demonstrated that a robust depletion of TfR-positive erythroid cells is also observable in human cellular systems (see, e.g., Example 7). Though the mice recovered from both the acute clinical symptoms and the decreased reticulocyte levels in due course, avoiding or otherwise mitigating this impact on reticulocytes is clearly desirable for an anti-TfR antibody to be able to be used safely as a therapeutic molecule.

Accordingly, the invention provides compositions and methods that greatly reduce or eliminate the unwanted reduction in the reticulocyte population upon anti-TfR administration while still enabling the enhanced BBB transport, increased CNS distribution and CNS retention provided by low-affinity anti-TfR antibodies administered at therapeutic concentrations. The results described herein show that the primary response to anti-TfR administration (robust reticulocyte depletion and acute clinical signs) is driven in large part by the antibody-dependent cell-mediated cytotoxicity (ADCC) activity of the antibody, while the residual reticulocyte depletion effect is mediated by the complement pathway. Several general approaches to mitigate the observed effect of anti-TfR antibodies on both the primary and residual reticulocyte depletion are provided herein, and may be used singly or in combination.

In one approach, the effector function of the anti-BBB-R antibody is reduced or eliminated in order to reduce or eliminate ADCC activity. In another approach, the affinity of the anti-BBB-R antibody for the BBB-R is further lessened such that interactions of the antibody with the reticulocyte population are less detrimental to that population. A third approach is directed to reducing the amount of anti-BBB-R antibody that is present in the plasma to reduce exposure of the reticulocyte population to potentially detrimental concentrations of the antibody. A fourth approach seeks to protect, stabilize and/or replenish reticulocyte populations such that any potential depletion of the reticulocyte population by administration of the anti-BBB-R antibody is avoided, lessened, or mitigated.

Effector function reduction or elimination, as described herein, may be accomplished by: (i) reduction or elimination of wild-type mammalian glycosylation of the antibody, (for example, by producing the antibody in an environment where such glycosylation cannot occur, by mutating one or more carbohydrate attachment points such that the antibody cannot be glycosylated, or by chemically or enzymatically removing one or more carbohydrates from the antibody after it has been glycosylated); (ii) by reduction or elimination of the Fc receptor-binding capability of the anti-BBB-R antibody (for example, by mutation of the Fc region, by deletion within the Fc region or elimination of the Fc region); or (iii) by utilization of an antibody isotype known to have minimal or no effector function (ie., including but not limited to IgG4).

Decreasing antibody complement activation, as described herein, may be accomplished by reduction or elimination of the C1q binding capability of the anti-BBB-R antibody (for example, by mutation of, deletion within or elimination of the Fc region, or by modifying the non-Fc portion of the anti-BBB-R antibody), or by otherwise suppressing activation or activity of the complement system (for example, by co-administering one or more complement pathway activation or complement pathway activity inhibitors).

When binding of anti-BBB-R antibody to BBB-R on reticulocytes or other cell types triggers their depletion, as with the anti-TfR antibodies exemplified herein, reduction of binding of the antibodies to the BBB-R on the reticulocytes or other cell types should in turn decrease the amount of reticulocyte or other cell type depletion observed upon antibody administration. In fact, this was demonstrated herein (see, e.g., FIG. 6B). The affinity of the anti-BBB-R antibody for the BBB-R may be modified using any of the methods described herein and as shown in the Examples.

Reducing the amount of anti-BBB-R antibody present in the plasma in order to reduce exposure of the reticulocyte population to potentially detrimental concentrations of the antibody may be accomplished in several ways. One method is to simply decrease the amount of the antibody that is dosed, potentially while also increasing the frequency of the dosing, such that the maximal concentration in the plasma is lowered but a sufficient serum level is maintained for efficacy, while still below the threshold of the cell-depleting side effect.

Another method, which may be combined with dosing modifications, is to select or engineer an anti-TfR antibody that has pH-sensitive binding to TfR such that it binds to cell surface TfR in the plasma at pH 7.4 with desirably low affinity as described herein, but upon internalization into an endosomal compartment, such binding to TfR is rapidly and significantly reduced at the relatively lower pH of that compartment (pH 5.5-6.0). Such dissociation may protect the antibody from antigen-mediated clearance, or increase the amount of antibody that is either delivered to the CNS or recycled back across the BBB—in either case, the effective concentration of the antibody is increased relative to an anti-TfR antibody that does not comprise such pH sensitivity, without increasing the administered dose of the antibody.

Protecting, stabilizing and/or replenishing reticulocyte populations may be accomplished using pharmaceutical or physical methods. In addition to the anti-BBB-R antibody, at least one further therapeutic agent may be coadministered (simultaneously or sequentially) that mitigates negative side effects of the antibody on reticulocyte populations. Examples of such therapeutic agents include, but are not limited to, erythropoietin (EPO), iron supplements, vitamin C, folic acid, and vitamin B12. Physical replacement of red blood cells (ie, reticulocytes) is also possible by, for example, transfusion with similar cells, which may be from another individual of similar blood type or may have been previously extracted from the subject to whom the anti-BBB-R antibody is administered.

One of ordinary skill in the art will appreciate that any combination of the foregoing methods may be employed to engineer an antibody (and/or dosage regimen for same) with the optimum balance between (i) the desirably low affinity for the BBB-R that will maximize transport of the antibody and any conjugated compounds into the CNS; (ii) the affinity of the conjugated compound (including as a nonlimiting example, a second or further antigen-binding specificity in the anti-TfR antibody) for its CNS antigen, since this is relevant to the amount of the compound that needs to be present in the CNS to have a therapeutic effect; (iii) the clearance rate of the anti-BBB-R antibody; and (iv) the impact on reticulocyte populations.

It will also be appreciated that the reticulocyte-depleting effect recognized herein of anti-TfR antibody administration may be useful in the treatment of any disease or disorder where overproliferation of reticulocytes is problematic. For example, in congenital polycythemia or neoplastic polycythemia vera, raised red blood cell counts due to hyperproliferation of, e.g., reticulocytes, results in thickening of blood and concomitant physiological symptoms. Administration of an anti-TfR antibody of the invention wherein at least partial effector function of the antibody was preserved would permit selective removal of immature reticulocyte populations without impacting normal transferrin transport into the CNS. Dosing of such an antibody could be modulated such that acute clinical symptoms could be minimized (ie, by dosing at a very low dose or at widely-spaced intervals), as well-understood in the art.

Anti-TfR/BACE1 and anti-TfR/Abeta are each promising and novel therapeutic candidates for the treatment of Alzheimer's disease. Furthermore, receptor mediated transport (RMT)-based bispecific targeting technology opens the door for a wide range of potential therapeutics for CNS diseases. The invention provides methods of engineering BBB-penetrant therapeutics that greatly improve transport across the BBB and CNS distribution of the therapeutic without depletion of reticulocytes.

Accordingly, in a first embodiment, the invention provides a method of transporting a compound across the blood-brain barrier in a subject comprising exposing an antibody which binds with low affinity to a blood-brain barrier receptor (BBB-R) coupled to a compound to the blood-brain barrier such that the antibody transports the compound coupled thereto across the blood-brain barrier, wherein reduction of red blood cell levels in the subject upon antibody administration to the subject is decreased or eliminated. In one aspect, the BBB-R is selected from the group consisting of transferrin receptor (TfR), insulin receptor, insulin-like growth factor receptor (IGF receptor), low density lipoprotein receptor-related protein 8 (LRP8), low density lipoprotein receptor-related protein 1 (LRP1), glucose transporter 1 (Glut1) and heparin-binding epidermal growth factor-like growth factor (HB-EGF). In another such aspect, the BBB-R is a human BBB-R. In one such aspect, the BBB-R is TfR. In another such aspect, the BBB-R is TfR, and the antibody does not inhibit TfR activity. In another such aspect, the BBB-R is TfR and the antibody does not inhibit the binding of TfR to transferrin.

In another aspect, the red blood cells are immature red blood cells. In another such aspect, the immature red blood cells are reticulocytes. In another aspect, reduction of reticulocyte levels is accompanied by acute clinical symptoms. In another aspect, the method further comprises the step of monitoring the subject for depletion of red blood cells.

In another aspect, one or more properties of the antibody have been modified to reduce the impact of the antibody on reticulocyte levels and/or reduce the severity or presence of acute clinical symptoms in the subject. In one such aspect, the affinity of the antibody for the BBB-R is modified, i.e., decreased. In another such aspect, the effector function of the antibody Fc region is modified. In one such aspect, the effector function has been reduced or eliminated relative to the effector function of a wild-type antibody of the same isotype. In another such aspect, the effector function is reduced or eliminated by reduction of glycosylation of the antibody. In another such aspect, the glycosylation of the antibody is reduced by production of the antibody in an environment that does not permit wild-type glycosylation. In one such aspect, the antibody is produced in a non-mammalian cell production system. In another such aspect, the antibody is produced synthetically. In another such aspect, the glycosylation of the antibody is reduced by removal of carbohydrate groups already present on the antibody. In another such aspect, the glycosylation of the antibody is reduced by modification of the antibody such that wild-type glycosylation does not occur. In another such aspect, the Fc region of the antibody comprises a mutation at position 297 such that the wild-type asparagine residue at that position is replaced with another amino acid that interferes with glycosylation at that position. In another aspect, the effector function is reduced or eliminated by modification of the antibody isotype to an isotype that naturally has reduced or eliminated effector function.

In another aspect, the Fc region is modified to reduce or eliminate effector function. In one such aspect, the effector function is reduced or eliminated by at least one modification of the Fc region. In one such aspect, the modification is a point mutation of the Fc region to impair binding to one or more Fc receptors selected from the following positions: 238, 239, 248, 249, 252, 254, 265, 268, 269, 270, 272, 278, 289, 292, 293, 294, 295, 296, 297, 298, 301, 303, 322, 324, 327, 329, 333, 335, 338, 340, 373, 376, 382, 388, 389, 414, 416, 419, 434, 435, 437, 438, and 439. In another such aspect, the modification is elimination of some or all of the Fc region. In another such aspect, the effector function is reduced or eliminated by deletion of all or a portion of the Fc region, or by engineering the antibody such that it does not include an Fc region competent for effector function. In one such aspect, the antibody is selected from a Fab or a single chain antibody.

In another aspect, the Fc region and/or the non-Fc region of the antibody is modified to reduce or eliminate activation of the complement pathway by the antibody. In one such aspect, the modification is a point mutation of the Fc region to impair binding to C1q selected from the following positions: 270, 322, 329, and 321. In another such aspect, the modification is elimination of some or all of the Fc region. In another such aspect, complement-triggering function is reduced or eliminated by deletion of all or a portion of the Fc region, or by engineering the antibody such that it does not include an Fc region that engages the complement pathway. In one such aspect, the antibody is selected from a Fab or a single chain antibody. In another such aspect, the non-Fc region of the antibody is modified to reduce or eliminate activation of the complement pathway by the antibody. In one such aspect, the modification is a point mutation of the CH1 region to impair binding to C3. In one such aspect, the point mutation is at position 132 (see, e.g., Vidarte et al., (2001) J. Biol. Chem. 276(41): 38217-38223).

In another aspect, the dose amount and/or frequency of administration of the antibody is modulated to reduce the concentration of the antibody to which the red blood cells are exposed. In another aspect, the antibody is modified to comprise pH-sensitive binding to the BBB-R.

In another aspect, a further compound is administered in addition to the antibody and the coupled compound. In one such aspect, the further compound is responsible for or contributes to the lack of reduction of reticulocyte levels. In another such aspect, the further compound inhibits or prevents the activation or activity of the complement pathway (see, e.g., Mollnes and Kirschfink (2006) Molec. Immunol. 43:107-121). In another such aspect, the further compound protects reticulocytes from antibody-related depletion. In another such aspect, the further compound supports the growth, development, or reestablishment of reticulocytes. In another aspect, the further compound is selected from erythropoietin (EPO), an iron supplement, vitamin C, folic acid and vitamin B12. In another aspect, the further compound is red blood cells or reticulocytes from the same subject. In another aspect, the further compound is red blood cells or reticulocytes from another subject.

In another aspect, the compound is a neurological disorder drug. In another aspect, the compound is an imaging agent. In another aspect, the compound is labeled. In another aspect, the antibody is labeled. In another aspect, the antibody does not impair the binding of the BBB-R to one or more of its native ligands. In another such aspect, the antibody specifically binds to TfR in such a manner that it does not inhibit binding of the TfR to transferrin. In another aspect, the BBB is in a mammal. In another such aspect, the mammal is a human. In another such aspect, the mammal has a neurological disorder. In another such aspect, the neurological disorder is selected from the group consisting of Alzheimer's disease (AD), stroke, dementia, muscular dystrophy (MD), multiple sclerosis (MS), amyotrophic lateral sclerosis (ALS), cystic fibrosis, Angelman's syndrome, Liddle syndrome, Parkinson's disease, Pick's disease, Paget's disease, cancer, and traumatic brain injury. In another aspect, the BBB is in a human.

In another aspect, the antibody has an IC50 for the BBB-R from about 1 nM to about 100 µM. In another such aspect, the IC50 is from about 5 nM to about 100 µM. In another such aspect, the IC50 is from about 50 nM to about 100 µM. In another such aspect, the IC50 is from about 100 nM to about 100 µM. In another aspect, the antibody has an affinity for the BBB-R from about 5 nM to about 50 µM. In another aspect, the antibody has an affinity for the BBB-R from about 30 nM to about 30 µM. In another such aspect, the antibody, when coupled to a compound, has an affinity for the BBB-R from about 30 nM to about 1 µM. In another such aspect, the antibody, when coupled to a compound, has an affinity for the BBB-R from about 50 nM to about 1 µM. In another such aspect, the compound-coupled antibody specifically binds to TfR and has an affinity for TfR between those affinities observed for the anti-TfR$^A$/BACE1 antibody and the anti-TfR$^E$/BACE1 antibody. In another such aspect, the compound-coupled antibody specifically binds to TfR and has an affinity for TfR between those affinities observed for the anti-TfR$^D$/BACE1 antibody and the anti-TfR$^E$/BACE1 antibody. In another such aspect, the compound-coupled antibody specifically binds to TfR and has an IC50 for TfR between those IC50s observed for the anti-TfR$^A$/BACE1 antibody and the anti-TfR$^E$/BACE1 antibody. In another such aspect, the compound-coupled antibody specifically binds to TfR and has an IC50 for TfR between those IC50s observed for the anti-TfR$^D$/BACE1 antibody and the anti-TfR$^E$/BACE1 antibody. In one aspect, the affinity of the anti-BBB-R or anti-BBB-R/compound for the BBB-R is measured using scatchard analysis. In another aspect, the affinity of the anti-BBB-R or anti-BBB-R/compound for the BBB-R is measured using BIACORE analysis. In another aspect, the affinity of the anti-BBB-R or anti-BBB-R/compound for the BBB-R is measured using a competition ELISA.

In another aspect, the dissociation half-life of the antibody from the BBB-R to which it specifically binds is from about 30 seconds to about 30 minutes. In another such aspect, the dissociation half-life is from about 30 seconds to about 20 minutes. In another such aspect, the dissociation half-life is from about 30 seconds to about 10 minutes. In another such aspect, the dissociation half-life is from about 30 seconds to about 5 minutes. In another such aspect, the dissociation half-life is from about 30 seconds to about 3 minutes. In another such aspect, the dissociation half-life is from about 30 seconds to about 2 minutes. In another such aspect, the dissociation half-life is about two minutes. In another such aspect, the dissociation half-life is one minute or less. In another such aspect, the compound-coupled antibody specifically binds to TfR and has a dissociation half-life for TfR between those dissociation half-lives observed for the anti-TfR$^A$/BACE1 antibody and the anti-TfR$^E$/BACE1 antibody from their respective binding to TfR. In another such aspect, the compound-coupled antibody specifically binds to TfR and has a dissociation half-life for TfR between those dissociation half-lives observed for the anti-TfR$^D$/BACE1 antibody and the anti-TfR$^E$/BACE1 antibody from their respective binding to TfR. In another aspect, the dissociation half-life of the anti-BBB-R or anti-BBB-R/compound for the BBB-R is measured using BIACORE analysis. In another aspect, the dissociation half-life of the anti-BBB-R or anti-BBB-R/compound for the BBB-R is measured using a competition binding assay, such as a competition ELISA. In another aspect, the compound-coupled antibody is administered at a therapeutic dose. In one such aspect, the therapeutic dose is a dose that saturates the BBB-R to which the antibody specifically binds. In another such aspect, the compound-coupled antibody is administered at a dose and dose frequency that minimizes red blood cell interaction with the compound-coupled antibody while still facilitating compound delivery across the BBB into the CNS at therapeutic levels.

In another aspect, the compound is covalently coupled to the antibody. In one such aspect, the compound is joined to the antibody by a linker. In one such aspect, the linker is cleavable. In another such aspect, the linker is not cleavable. In another such aspect, the compound is directly linked to the antibody. In one such aspect, the antibody is a multi-specific antibody and the compound forms one portion of the multispecific antibody. In another such aspect, the multispecific antibody comprises a first antigen binding site which binds the BBB-R and a second antigen binding site which binds a brain antigen. In another such aspect, the brain antigen is selected from the group consisting of: beta-secretase 1 (BACE1), Abeta, epidermal growth factor receptor (EGFR), human epidermal growth factor receptor 2 (HER2), Tau, apolipoprotein E4 (ApoE4), alpha-synuclein, CD20, huntingtin, prion protein (PrP), leucine rich repeat kinase 2 (LRRK2), parkin, presenilin 1, presenilin 2, gamma secretase, death receptor 6 (DR6), amyloid precursor protein (APP), p75 neurotrophin receptor (p75NTR), interleukin 6 receptor (IL6R), TNF receptor 1 (TNFR1), interleukin 1 beta (IL1β), and caspase 6. In another such aspect, the multispecific antibody binds both TfR and BACE1. In another such aspect, the multispecific antibody binds both TfR and Abeta. In another such aspect, the multispecific antibody is labeled. In another aspect, the compound is reversibly coupled to the antibody such that the compound is released from the antibody concurrent with or after BBB transport.

It will be appreciated that any of the foregoing aspects may be applied singly or in combination with the foregoing embodiment.

In another embodiment, the invention provides a method of increasing exposure of the CNS of a subject to a compound, wherein the compound is coupled to an antibody which binds with low affinity to a BBB-R, thereby increasing the exposure of the CNS to the compound, and wherein reduction of red blood cell levels in the subject upon compound-coupled antibody administration to the subject is decreased or eliminated. In one aspect, the BBB-R is selected from the group consisting of transferrin receptor (TfR), insulin receptor, insulin-like growth factor receptor (IGF receptor), low density lipoprotein receptor-related protein 8 (LRP8), low density lipoprotein receptor-related protein 1 (LRP1), glucose transporter 1 (Glut1) and heparin-binding epidermal growth factor-like growth factor (HB-EGF). In another such aspect, the BBB-R is a human BBB-R. In one such aspect, the BBB-R is TfR. In another such aspect, the BBB-R is TfR, and the antibody does not inhibit TfR activity. In another such aspect, the BBB-R is TfR and the antibody does not inhibit the binding of TfR to transferrin.

In another aspect, the red blood cells are immature red blood cells. In another such aspect, the immature red blood cells are reticulocytes. In another aspect, reduction of reticulocyte levels is accompanied by acute clinical symptoms. In another aspect, the method further comprises the step of monitoring the subject for depletion of red blood cells.

In another aspect, one or more properties of the antibody have been modified to reduce the impact of the antibody on reticulocyte levels and/or reduce the severity or presence of acute clinical symptoms in the subject. In one such aspect, the affinity of the antibody for the BBB-R is modified, i.e., decreased. In another such aspect, the effector function of the antibody Fc region is modified. In one such aspect, the effector function has been reduced or eliminated relative to the effector function of a wild-type antibody of the same isotype. In another such aspect, the effector function is reduced or eliminated by reduction of glycosylation of the antibody. In another such aspect, the glycosylation of the antibody is reduced by production of the antibody in an environment that does not permit wild-type glycosylation. In one such aspect, the antibody is produced in a non-mammalian cell production system. In another such aspect, the antibody is produced synthetically. In another such aspect, the glycosylation of the antibody is reduced by removal of carbohydrate groups already present on the antibody. In another such aspect, the glycosylation of the antibody is reduced by modification of the antibody such that wild-type glycosylation does not occur. In another such aspect, the Fc region of the antibody comprises a mutation at position 297 such that the wild-type asparagine residue at that position is replaced with another amino acid that interferes with glycosylation at that position. In another aspect, the effector function is reduced or eliminated by modification of the antibody isotype to an isotype that naturally has reduced or eliminated effector function.

In another aspect, the Fc region is modified to reduce or eliminate effector function. In one such aspect, the effector function is reduced or eliminated by at least one modification of the Fc region. In one such aspect, the modification is a point mutation of the Fc region to impair binding to one or more Fc receptors selected from the following positions: 238, 239, 248, 249, 252, 254, 265, 268, 269, 270, 272, 278, 289, 292, 293, 294, 295, 296, 297, 298, 301, 303, 322, 324, 327, 329, 333, 335, 338, 340, 373, 376, 382, 388, 389, 414, 416, 419, 434, 435, 437, 438, and 439. In another such aspect, the modification is elimination of some or all of the Fc region. In another such aspect, the effector function is reduced or eliminated by deletion of all or a portion of the Fc region, or by engineering the antibody such that it does not include an Fc region competent for effector function. In one such aspect, the antibody is selected from a Fab or a single chain antibody.

In another such aspect, the Fc region and/or the non-Fc region of the antibody is modified to reduce or eliminate activation of the complement pathway by the antibody. In one such aspect, the modification is a point mutation of the Fc region to impair binding to C1q selected from the following positions: 270, 322, 329, and 321. In another such aspect, the modification is elimination of some or all of the Fc region. In another such aspect, complement-triggering function is reduced or eliminated by deletion of all or a portion of the Fc region, or by engineering the antibody such that it does not include an Fc region that engages the complement pathway. In one such aspect, the antibody is selected from a Fab or a single chain antibody. In another such aspect, the non-Fc region of the antibody is modified to reduce or eliminate activation of the complement pathway by the antibody. In one such aspect, the modification is a point mutation of the CH1 region to impair binding to C3. In one such aspect, the point mutation is at position 132 (see, e.g., Vidarte et al., (2001) J. Biol. Chem. 276(41): 38217-38223).

In another aspect, the dose amount and/or frequency of administration of the antibody is modulated to reduce the concentration of the antibody to which the red blood cells are exposed. In another aspect, the antibody is modified to comprise pH-sensitive binding to the BBB-R.

In another aspect, a further compound is administered in addition to the antibody and the coupled compound. In one such aspect, the further compound is responsible for or contributes to the lack of reduction of reticulocyte levels. In another such aspect, the further compound inhibits or prevents the activation or activity of the complement pathway (see, e.g., Mollnes and Kirschfink (2006) Molec. Immunol. 43:107-121). In another such aspect, the further compound protects reticulocytes from antibody-related depletion. In another such aspect, the further compound supports the growth, development, or reestablishment of reticulocytes. In another aspect, the further compound is selected from erythropoietin (EPO), an iron supplement, vitamin C, folic acid and vitamin B12. In another aspect, the further compound is red blood cells or reticulocytes from the same subject. In another such aspect, the further compound is red blood cells or reticulocytes from another subject.

In another aspect, the compound is a neurological disorder drug. In another aspect, the compound is an imaging agent. In another aspect, the compound is labeled. In another aspect, the antibody is labeled. In another aspect, the antibody does not impair the binding of the BBB-R to one or more of its native ligands. In another such aspect, the antibody specifically binds to TfR in such a manner that it does not inhibit binding of the TfR to transferrin. In another aspect, the antibody-coupled compound is administered to a mammal. In another such aspect, the mammal is a human. In another such aspect, the mammal has a neurological disorder. In another such aspect, the neurological disorder is selected from the group consisting of Alzheimer's disease (AD), stroke, dementia, muscular dystrophy (MD), multiple sclerosis (MS), amyotrophic lateral sclerosis (ALS), cystic fibrosis, Angelman's syndrome, Liddle syndrome, Parkinson's disease, Pick's disease, Paget's disease, cancer, and traumatic brain injury.

In another aspect, the increase in CNS exposure to the compound is measured relative to the CNS exposure of a compound coupled with a typical antibody not having lowered affinity for the BBB-R. In another aspect, the increase in CNS exposure to the compound is measured as a ratio of the amount of the compound found in the CNS relative to the amount found in the serum after administration. In another such aspect, the increase in CNS exposure results in a ratio of greater than 0.1%. In another aspect, the increase in CNS exposure to the compound is measured relative to the CNS exposure of a compound in the absence of a coupled antibody. In another aspect, the increase in CNS exposure to the compound is measured by imaging. In another aspect, the increase in CNS exposure to the compound is measured by an indirect readout such as a modification of one or more physiological symptoms.

In another aspect, the antibody has an IC50 for the BBB-R from about 1 nM to about 100 µM. In another such aspect, the IC50 is from about 5 nM to about 100 µM. In another such aspect, the IC50 is from about 50 nM to about 100 µM. In another such aspect, the IC50 is from about 100 nM to about 100 µM. In another aspect, the antibody has an affinity for the BBB-R from about 5 nM to about 50 µM. In another aspect, the antibody has an affinity for the BBB-R from about 30 nM to about 30 µM. In another such aspect, the antibody, when coupled to a compound, has an affinity for the BBB-R from about 30 nM to about 1 µM. In another such aspect, the antibody, when coupled to a compound, has an affinity for the BBB-R from about 50 nM to about 1 µM. In another such aspect, the compound-coupled antibody specifically binds to TfR and has an affinity for TfR between those affinities observed for the anti-TfR$^A$/BACE1 antibody and the anti-TfR$^E$/BACE1 antibody. In another such aspect, the compound-coupled antibody specifically binds to TfR and has an affinity for TfR between those affinities observed for the anti-TfR$^D$/BACE1 antibody and the anti-TfR$^E$/BACE1 antibody. In another such aspect, the compound-coupled antibody specifically binds to TfR and has an IC50 for TfR between those IC50s observed for the anti-TfR$^A$/BACE1 antibody and the anti-TfR$^E$/BACE1 antibody. In another such aspect, the compound-coupled antibody specifically binds to TfR and has an IC50 for TfR between those IC50s observed for the anti-TfR$^D$/BACE1 antibody and the anti-TfR$^E$/BACE1 antibody. In one aspect, the affinity of the anti-BBB-R or anti-BBB-R/compound for the BBB-R is measured using scatchard analysis.

In another aspect, the affinity of the anti-BBB-R or anti-BBB-R/compound for the BBB-R is measured using BIACORE analysis. In another aspect, the affinity of the anti-BBB-R or anti-BBB-R/compound for the BBB-R is measured using a competition ELISA.

In another aspect, the dissociation half-life of the antibody from the BBB-R to which it specifically binds is from about 30 seconds to about 30 minutes. In another such aspect, the dissociation half-life is from about 30 seconds to about 20 minutes. In another such aspect, the dissociation half-life is from about 30 seconds to about 10 minutes. In another such aspect, the dissociation half-life is from about 30 seconds to about 5 minutes. In another such aspect, the dissociation half-life is from about 30 seconds to about 3 minutes. In another such aspect, the dissociation half-life is from about 30 seconds to about 2 minutes. In another such aspect, the dissociation half-life is about two minutes. In another such aspect, the dissociation half-life is one minute or less. In another such aspect, the compound-coupled antibody specifically binds to TfR and has a dissociation half-life for TfR between those dissociation half-lives observed for the anti-TfR$^A$/BACE1 antibody and the anti-TfR$^E$/BACE1 antibody from their respective binding to TfR. In another such aspect, the compound-coupled antibody specifically binds to TfR and has a dissociation half-life for TfR between those dissociation half-lives observed for the anti-TfR$^D$/BACE1 antibody and the anti-TfR$^E$/BACE1 antibody from their respective binding to TfR. In another aspect, the dissociation half-life of the anti-BBB-R or anti-BBB-R/compound for the BBB-R is measured using BIACORE analysis. In another aspect, the dissociation half-life of the anti-BBB-R or anti-BBB-R/compound for the BBB-R is measured using a competition binding assay, such as a competition ELISA.

In another aspect, the compound-coupled antibody is administered at a therapeutic dose. In one such aspect, the therapeutic dose is a dose that saturates the BBB-R to which the antibody specifically binds. In another such aspect, the compound-coupled antibody is administered at a dose and dose frequency that minimizes red blood cell interaction with the compound-coupled antibody while still facilitating compound delivery across the BBB into the CNS at therapeutic levels.

In another aspect, the compound is covalently coupled to the antibody. In one such aspect, the compound is joined to the antibody by a linker. In one such aspect, the linker is cleavable. In another such aspect, the linker is not cleavable. In another such aspect, the compound is directly linked to the antibody. In one such aspect, the antibody is a multispecific antibody and the compound forms one portion of the multispecific antibody. In another such aspect, the multispecific antibody comprises a first antigen binding site which binds the BBB-R and a second antigen binding site which binds a brain antigen. In another such aspect, the brain antigen is selected from the group consisting of: beta-secretase 1 (BACE1), Abeta, epidermal growth factor receptor (EGFR), human epidermal growth factor receptor 2 (HER2), Tau, apolipoprotein E4 (ApoE4), alpha-synuclein, CD20, huntingtin, prion protein (PrP), leucine rich repeat kinase 2 (LRRK2), parkin, presenilin 1, presenilin 2, gamma secretase, death receptor 6 (DR6), amyloid precursor protein (APP), p75 neurotrophin receptor (p75NTR), interleukin 6 receptor (IL6R), TNF receptor 1 (TNFR1), interleukin 1 beta (IL1β), and caspase 6. In another such aspect, the multispecific antibody binds both TfR and BACE1. In another such aspect, the multispecific antibody binds both TfR and Abeta. In another such aspect, the multispecific antibody is labeled. In another aspect, the compound is reversibly coupled to the antibody such that the compound is released from the antibody concurrent with or after BBB transport.

It will be appreciated that any of the foregoing aspects may be applied singly or in combination with the foregoing embodiment.

In another embodiment, the invention provides a method of decreasing clearance of a compound administered to a subject, wherein the compound is coupled to an antibody which binds with low affinity to a BBB-R, such that the clearance of the compound is decreased, and wherein reduction of red blood cell levels in the subject upon compound-coupled antibody administration to the subject is decreased or eliminated. In one aspect, the BBB-R is selected from the group consisting of transferrin receptor (TfR), insulin receptor, insulin-like growth factor receptor (IGF receptor), low density lipoprotein receptor-related protein 8 (LRP8), low density lipoprotein receptor-related protein 1 (LRP1), glucose transporter 1 (Glut1) and heparin-binding epidermal growth factor-like growth factor (HB-EGF). In another such aspect, the BBB-R is a human BBB-R. In one such aspect, the BBB-R is TfR. In another such aspect, the BBB-R is TfR, and the antibody does not inhibit TfR activity. In another such aspect, the BBB-R is TfR and the antibody does not inhibit the binding of TfR to transferrin.

In another aspect, the red blood cells are immature red blood cells. In another such aspect, the immature red blood cells are reticulocytes. In another aspect, reduction of reticulocyte levels is accompanied by acute clinical symptoms. In another aspect, the method further comprises the step of monitoring the subject for depletion of red blood cells.

In another aspect, one or more properties of the antibody have been modified to reduce the impact of the antibody on reticulocyte levels and/or reduce the severity or presence of acute clinical symptoms in the subject. In one such aspect, the affinity of the antibody for the BBB-R is modified, i.e., decreased. In another such aspect, the effector function of the antibody Fc region is modified. In one such aspect, the effector function has been reduced or eliminated relative to the effector function of a wild-type antibody of the same isotype. In another such aspect, the effector function is reduced or eliminated by reduction of glycosylation of the antibody. In another such aspect, the glycosylation of the antibody is reduced by production of the antibody in an environment that does not permit wild-type glycosylation. In one such aspect, the antibody is produced in a non-mammalian cell production system. In another such aspect, the antibody is produced synthetically. In another such aspect, the glycosylation of the antibody is reduced by removal of carbohydrate groups already present on the antibody. In another such aspect, the glycosylation of the antibody is reduced by modification of the antibody such that wild-type glycosylation does not occur. In another such aspect, the Fc region of the antibody comprises a mutation at position 297 such that the wild-type asparagine residue at that position is replaced with another amino acid that interferes with glycosylation at that position. In another aspect, the effector function is reduced or eliminated by modification of the antibody isotype to an isotype that naturally has reduced or eliminated effector function.

In another aspect, the Fc region is modified to reduce or eliminate effector function. In one such aspect, the effector function is reduced or eliminated by at least one modification of the Fc region. In one such aspect, the modification is a point mutation of the Fc region to impair binding to one or more Fc receptors selected from the following positions: 238, 239, 248, 249, 252, 254, 265, 268, 269, 270, 272, 278, 289, 292, 293, 294, 295, 296, 297, 298, 301, 303, 322, 324, 327, 329, 333, 335, 338, 340, 373, 376, 382, 388, 389, 414, 416, 419, 434, 435, 437, 438, and 439. In another such aspect, the modification is elimination of some or all of the Fc region. In another such aspect, the effector function is reduced or eliminated by deletion of all or a portion of the Fc region, or by engineering the antibody such that it does not include an Fc region competent for effector function. In one such aspect, the antibody is selected from a Fab or a single chain antibody.

In another aspect, the Fc region and/or the non-Fc region of the antibody is modified to reduce or eliminate activation of the complement pathway by the antibody. In one such aspect, the modification is a point mutation of the Fc region to impair binding to C1q selected from the following positions: 270, 322, 329, and 321. In another such aspect, the modification is elimination of some or all of the Fc region. In another such aspect, complement-triggering function is reduced or eliminated by deletion of all or a portion of the Fc region, or by engineering the antibody such that it does not include an Fc region that engages the complement pathway. In one such aspect, the antibody is selected from a Fab or a single chain antibody. In another such aspect, the non-Fc region of the antibody is modified to reduce or eliminate activation of the complement pathway by the antibody. In one such aspect, the modification is a point mutation of the CH1 region to impair binding to C3. In one such aspect, the point mutation is at position 132 (see, e.g., Vidarte et al., (2001) J. Biol. Chem. 276(41): 38217-38223).

In another aspect, the dose amount and/or frequency of administration of the antibody is modulated to reduce the concentration of the antibody to which the red blood cells are exposed. In another aspect, the antibody is modified to comprise pH-sensitive binding to the BBB-R.

In another aspect, a further compound is administered in addition to the antibody and the coupled compound. In one such aspect, the further compound is responsible for or contributes to the lack of reduction of reticulocyte levels. In another such aspect, the further compound inhibits or prevents the activation or activity of the complement pathway (see, e.g., Mollnes and Kirschfink (2006) *Molec. Immunol.* 43:107-121). In another such aspect, the further compound protects reticulocytes from antibody-related depletion. In another such aspect, the further compound supports the growth, development, or reestablishment of reticulocytes. In another aspect, the further compound is selected from erythropoietin (EPO), an iron supplement, vitamin C, folic acid and vitamin B12. In another aspect, the further compound is red blood cells or reticulocytes from the same subject. In another aspect, the further compound is red blood cells or reticulocytes from another subject.

In another aspect, the compound is a neurological disorder drug. In another aspect, the compound is an imaging agent. In another aspect, the compound is labeled. In another aspect, the antibody is labeled. In another aspect, the antibody does not impair the binding of the BBB-R to one or more of its native ligands. In another such aspect, the antibody specifically binds to TfR in such a manner that it does not inhibit binding of the TfR to transferrin. In another aspect, the subject is a mammal. In another such aspect, the mammal is a human. In another such aspect, the mammal has a neurological disorder. In another such aspect, the neurological disorder is selected from the group consisting of Alzheimer's disease (AD), stroke, dementia, muscular dystrophy (MD), multiple sclerosis (MS), amyotrophic lateral sclerosis (ALS), cystic fibrosis, Angelman's syndrome, Liddle syndrome, Parkinson's disease, Pick's disease, Paget's disease, cancer, and traumatic brain injury.

In another aspect, the decrease in clearance of the compound is measured relative to the clearance of a compound coupled with a typical antibody not having lowered affinity for the BBB-R. In another aspect, the decrease in clearance of the compound is measured relative to the clearance of the compound in the absence of a coupled antibody.

In another aspect, the antibody has an IC50 for the BBB-R from about 1 nM to about 100 μM. In another such aspect, the IC50 is from about 5 nM to about 100 μM. In another such aspect, the IC50 is from about 50 nM to about 100 μM. In another such aspect, the IC50 is from about 100 nM to about 100 μM. In another aspect, the antibody has an affinity for the BBB-R from about 5 nM to about 50 μM. In another aspect, the antibody has an affinity for the BBB-R from about 30 nM to about 30 μM. In another such aspect, the antibody, when coupled to a compound, has an affinity for the BBB-R from about 30 nM to about 1 μM. In another such aspect, the antibody, when coupled to a compound, has an affinity for the BBB-R from about 50 nM to about 1 μM. In another such aspect, the compound-coupled antibody specifically binds to TfR and has an affinity for TfR between those affinities observed for the anti-$TfR^A$/BACE1 antibody and the anti-$TfR^E$/BACE1 antibody. In another such aspect, the compound-coupled antibody specifically binds to TfR and has an affinity for TfR between those affinities observed for the anti-$TfR^D$/BACE1 antibody and the anti-$TfR^E$/BACE1 antibody. In another such aspect, the compound-coupled antibody specifically binds to TfR and has an IC50 for TfR between those IC50s observed for the anti-$TfR^A$/BACE1 antibody and the anti-$TfR^E$/BACE1 antibody. In another such aspect, the compound-coupled antibody specifically binds to TfR and has an IC50 for TfR between those IC50s observed for the anti-TfR$^D$/BACE1 antibody and the anti-TfR$^E$/BACE1 antibody. In one aspect, the affinity of the anti-BBB-R or anti-BBB-R/compound for the BBB-R is measured using scatchard analysis. In another aspect, the affinity of the anti-BBB-R or anti-BBB-R/compound for the BBB-R is measured using BIACORE analysis. In another aspect, the affinity of the anti-BBB-R or anti-BBB-R/compound for the BBB-R is measured using a competition ELISA.

In another aspect, the dissociation half-life of the antibody from the BBB-R to which it specifically binds is from about 30 seconds to about 30 minutes. In another such aspect, the dissociation half-life is from about 30 seconds to about 20 minutes. In another such aspect, the dissociation half-life is from about 30 seconds to about 10 minutes. In another such aspect, the dissociation half-life is from about 30 seconds to about 5 minutes. In another such aspect, the dissociation half-life is from about 30 seconds to about 3 minutes. In another such aspect, the dissociation half-life is from about 30 seconds to about 2 minutes. In another such aspect, the dissociation half-life is about two minutes. In another such aspect, the dissociation half-life is one minute or less. In another such aspect, the compound-coupled antibody specifically binds to TfR and has a dissociation half-life for TfR between those dissociation half-lives observed for the anti-TfR$^A$/BACE1 antibody and the anti-TfR$^E$/BACE1 antibody from their respective binding to TfR. In another such aspect, the compound-coupled antibody specifically binds to TfR and has a dissociation half-life for TfR between those dissociation half-lives observed for the anti-TfR$^D$/BACE1 antibody and the anti-TfR$^E$/BACE1 antibody from their respective binding to TfR. In another aspect, the dissociation half-life of the anti-BBB-R or anti-BBB-R/compound for the BBB-R is measured using BIACORE analysis. In another aspect, the dissociation half-life of the anti-BBB-R or anti-BBB-R/compound for the BBB-R is measured using a competition binding assay, such as a competition ELISA.

In another aspect, the compound-coupled antibody is administered at a therapeutic dose. In one such aspect, the therapeutic dose is a dose that saturates the BBB-R to which the antibody specifically binds. In another such aspect, the compound-coupled antibody is administered at a dose and dose frequency that minimizes red blood cell interaction with the compound-coupled antibody while still facilitating compound delivery across the BBB into the CNS at therapeutic levels.

In another aspect, the compound is covalently coupled to the antibody. In one such aspect, the compound is joined to the antibody by a linker. In one such aspect, the linker is cleavable. In another such aspect, the linker is not cleavable. In another such aspect, the compound is directly linked to the antibody. In one such aspect, the antibody is a multispecific antibody and the compound forms one portion of the multispecific antibody. In another such aspect, the multispecific antibody comprises a first antigen binding site which binds the BBB-R and a second antigen binding site which binds a brain antigen. In another such aspect, the brain antigen is selected from the group consisting of: beta-secretase 1 (BACE1), Abeta, epidermal growth factor receptor (EGFR), human epidermal growth factor receptor 2 (HER2), Tau, apolipoprotein E4 (ApoE4), alpha-synuclein, CD20, huntingtin, prion protein (PrP), leucine rich repeat kinase 2 (LRRK2), parkin, presenilin 1, presenilin 2, gamma secretase, death receptor 6 (DR6), amyloid precursor protein (APP), p75 neurotrophin receptor (p75NTR), interleukin 6 receptor (IL6R), TNF receptor 1 (TNFR1), interleukin 1 beta (IL1β), and caspase 6. In another such aspect, the multispecific antibody binds both TfR and BACE1. In another such aspect, the multispecific antibody binds both TfR and Abeta. In another such aspect, the multispecific antibody is labeled. In another such aspect, the compound is reversibly coupled to the antibody such that the compound is released from the antibody concurrent with or after BBB transport.

It will be appreciated that any of the foregoing aspects may be applied singly or in combination with the foregoing embodiment.

A method of increasing retention in the CNS of a compound administered to a subject, wherein the compound is coupled to an antibody which binds with low affinity to a BBB-R, such that the retention in the CNS of the compound is increased, and wherein reduction of red blood cell levels in the subject upon compound-coupled antibody administration to the subject is decreased or eliminated. In one aspect, the BBB-R is selected from the group consisting of transferrin receptor (TfR), insulin receptor, insulin-like growth factor receptor (IGF receptor), low density lipoprotein receptor-related protein 8 (LRP8), low density lipoprotein receptor-related protein 1 (LRP1), glucose transporter 1 (Glut1) and heparin-binding epidermal growth factor-like growth factor (HB-EGF). In another such aspect, the BBB-R is a human BBB-R. In one such aspect, the BBB-R is TfR. In another such aspect, the BBB-R is TfR, and the antibody does not inhibit TfR activity. In another such aspect, the BBB-R is TfR and the antibody does not inhibit the binding of TfR to transferrin.

In another aspect, the red blood cells are immature red blood cells. In another such aspect, the immature red blood cells are reticulocytes. In another aspect, reduction of reticulocyte levels is accompanied by acute clinical symptoms. In another aspect, the method further comprises the step of monitoring the subject for depletion of red blood cells.

In another aspect, one or more properties of the antibody have been modified to reduce the impact of the antibody on reticulocyte levels and/or reduce the severity or presence of acute clinical symptoms in the subject. In one such aspect, the affinity of the antibody for the BBB-R is modified, i.e., decreased. In another such aspect, the effector function of the antibody Fc region is modified. In one such aspect, the effector function has been reduced or eliminated relative to the effector function of a wild-type antibody of the same isotype. In another such aspect, the effector function is reduced or eliminated by reduction of glycosylation of the antibody. In another such aspect, the glycosylation of the antibody is reduced by production of the antibody in an environment that does not permit wild-type glycosylation. In one such aspect, the antibody is produced in a non-mammalian cell production system. In another such aspect, the antibody is produced synthetically. In another such aspect, the glycosylation of the antibody is reduced by removal of carbohydrate groups already present on the antibody. In another such aspect, the glycosylation of the antibody is reduced by modification of the antibody such that wild-type glycosylation does not occur. In another such aspect, the Fc region of the antibody comprises a mutation at position 297 such that the wild-type asparagine residue at that position is replaced with another amino acid that interferes with glycosylation at that position. In another aspect, the effector function is reduced or eliminated by modification of the antibody isotype to an isotype that naturally has reduced or eliminated effector function.

In another aspect, the Fc region is modified to reduce or eliminate effector function. In one such aspect, the effector function is reduced or eliminated by at least one modification of the Fc region. In one such aspect, the modification is a point mutation of the Fc region to impair binding to one or more Fc receptors selected from the following positions: 238, 239, 248, 249, 252, 254, 265, 268, 269, 270, 272, 278, 289, 292, 293, 294, 295, 296, 297, 298, 301, 303, 322, 324, 327, 329, 333, 335, 338, 340, 373, 376, 382, 388, 389, 414, 416, 419, 434, 435, 437, 438, and 439. In another such aspect, the modification is elimination of some or all of the Fc region. In another such aspect, the effector function is reduced or eliminated by deletion of all or a portion of the Fc region, or by engineering the antibody such that it does not include an Fc region competent for effector function. In one such aspect, the antibody is selected from a Fab or a single chain antibody.

In another aspect, the Fc region and/or the non-Fc region of the antibody is modified to reduce or eliminate activation of the complement pathway by the antibody. In one such aspect, the modification is a point mutation of the Fc region to impair binding to C1q selected from the following positions: 270, 322, 329, and 321. In another such aspect, the modification is elimination of some or all of the Fc region. In another such aspect, complement-triggering function is reduced or eliminated by deletion of all or a portion of the Fc region, or by engineering the antibody such that it does not include an Fc region that engages the complement pathway. In one such aspect, the antibody is selected from a Fab or a single chain antibody. In another such aspect, the non-Fc region of the antibody is modified to reduce or eliminate activation of the complement pathway by the antibody. In one such aspect, the modification is a point mutation of the CH1 region to impair binding to C3. In one such aspect, the point mutation is at position 132 (see, e.g., Vidarte et al., (2001) J. Biol. Chem. 276(41): 38217-38223).

In another aspect, the dose amount and/or frequency of administration of the antibody is modulated to reduce the concentration of the antibody to which the red blood cells are exposed. In another aspect, the antibody is modified to comprise pH-sensitive binding to the BBB-R.

In another aspect, a further compound is administered in addition to the antibody and the coupled compound. In one such aspect, the further compound is responsible for or contributes to the lack of reduction of reticulocyte levels. In another such aspect, the further compound inhibits or prevents the activation or activity of the complement pathway (see, e.g., Mollnes and Kirschfink (2006) Molec. Immunol. 43:107-121). In another such aspect, the further compound protects reticulocytes from antibody-related depletion. In another such aspect, the further compound supports the growth, development, or reestablishment of reticulocytes. In another aspect, the further compound is selected from erythropoietin (EPO), an iron supplement, vitamin C, folic acid and vitamin B12. In another aspect, the further compound is red blood cells or reticulocytes from the same subject. In another aspect, the further compound is red blood cells or reticulocytes from another subject.

In another aspect, the compound is a neurological disorder drug. In another aspect, the compound is an imaging agent. In another aspect, the compound is labeled. In another aspect, the antibody is labeled. In another such aspect, the antibody does not impair the binding of the BBB-R to one or more of its native ligands. In another such aspect, the antibody specifically binds to TfR in such a manner that it does not inhibit binding of the TfR to transferrin. In another aspect, the compound is administered to a mammal. In another such aspect, the mammal is a human. In another such aspect, the mammal has a neurological disorder. In another such aspect, the neurological disorder is selected from the group consisting of Alzheimer's disease (AD), stroke, dementia, muscular dystrophy (MD), multiple sclerosis (MS), amyotrophic lateral sclerosis (ALS), cystic fibrosis, Angelman's syndrome, Liddle syndrome, Parkinson's disease, Pick's disease, Paget's disease, cancer, and traumatic brain injury.

In another aspect, the increase in CNS retention of the compound is measured relative to the CNS retention of a compound coupled with a typical antibody not having lowered affinity for the BBB-R. In another aspect, the increase in CNS retention of the compound is measured as a ratio of the amount of the compound found in the CNS relative to the amount found in the serum at one or more time points after administration. In another such aspect, the increase in CNS retention results in a ratio of greater than 0.1% at one or more time points after administration. In another aspect, the increase in CNS retention of the compound is measured relative to the CNS retention of a compound in the absence of a coupled antibody. In another aspect, the increase in CNS retention of the compound is measured by imaging. In another aspect, the increase in CNS retention of the compound is measured by an indirect readout such as a modification of one or more physiological symptoms.

In another aspect, the antibody has an IC50 for the BBB-R from about 1 nM to about 100 µM. In another such aspect, the IC50 is from about 5 nM to about 100 µM. In another such aspect, the IC50 is from about 50 nM to about 100 µM. In another such aspect, the IC50 is from about 100 nM to about 100 µM. In another aspect, the antibody has an affinity for the BBB-R from about 5 nM to about 50 µM. In another aspect, the antibody has an affinity for the BBB-R from about 30 nM to about 30 µM. In another such aspect, the antibody, when coupled to a compound, has an affinity for the BBB-R from about 30 nM to about 1 µM. In another such aspect, the antibody, when coupled to a compound, has an affinity for the BBB-R from about 50 nM to about 1 µM. In another such aspect, the compound-coupled antibody specifically binds to TfR and has an affinity for TfR between those affinities observed for the anti-TfR$^A$/BACE1 antibody and the anti-TfR$^E$/BACE1 antibody. In another such aspect, the compound-coupled antibody specifically binds to TfR and has an affinity for TfR between those affinities observed for the anti-TfR$^D$/BACE1 antibody and the anti-TfR$^E$/BACE1 antibody. In another such aspect, the compound-coupled antibody specifically binds to TfR and has an IC50 for TfR between those IC50s observed for the anti-TfR$^A$/BACE1 antibody and the anti-TfR$^E$/BACE1 antibody. In another such aspect, the compound-coupled antibody specifically binds to TfR and has an IC50 for TfR between those IC50s observed for the anti-TfR$^D$/BACE1 antibody and the anti-TfR$^E$/BACE1 antibody. In one aspect, the affinity of the anti-BBB-R or anti-BBB-R/compound for the BBB-R is measured using scatchard analysis. In another aspect, the affinity of the anti-BBB-R or anti-BBB-R/compound for the BBB-R is measured using BIACORE analysis. In another aspect, the affinity of the anti-BBB-R or anti-BBB-R/compound for the BBB-R is measured using a competition ELISA.

In another aspect, the dissociation half-life of the antibody from the BBB-R to which it specifically binds is from about 30 seconds to about 30 minutes. In another such aspect, the dissociation half-life is from about 30 seconds to about 20 minutes. In another such aspect, the dissociation half-life is from about 30 seconds to about 10 minutes. In another such aspect, the dissociation half-life is from about 30 seconds to about 5 minutes. In another such aspect, the dissociation half-life is from about 30 seconds to about 3 minutes. In another such aspect, the dissociation half-life is from about 30 seconds to about 2 minutes. In another such aspect, the dissociation half-life is about two minutes. In another such aspect, the dissociation half-life is one minute or less. In another such aspect, the compound-coupled antibody specifically binds to TfR and has a dissociation half-life for TfR between those dissociation half-lives observed for the anti-TfR$^A$/BACE1 antibody and the anti-TfR$^E$/BACE1 antibody from their respective binding to TfR. In another such aspect, the compound-coupled antibody specifically binds to TfR and has a dissociation half-life for TfR between those dissociation half-lives observed for the anti-TfR$^A$/BACE1 antibody and the anti-TfR$^E$/BACE1 antibody from their respective binding to TfR. In another aspect, the dissociation half-life of the anti-BBB-R or anti-BBB-R/compound for the BBB-R is measured using BIACORE analysis. In another aspect, the dissociation half-life of the anti-BBB-R or anti-BBB-R/compound for the BBB-R is measured using a competition binding assay, such as a competition ELISA.

In another aspect, the compound-coupled antibody is administered at a therapeutic dose. In one such aspect, the therapeutic dose is a dose that saturates the BBB-R to which the antibody specifically binds. In another such aspect, the compound-coupled antibody is administered at a dose and dose frequency that minimizes red blood cell interaction with the compound-coupled antibody while still facilitating compound delivery across the BBB into the CNS at therapeutic levels.

In another aspect, the compound is covalently coupled to the antibody. In one such aspect, the compound is joined to the antibody by a linker. In one such aspect, the linker is cleavable. In another such aspect, the linker is not cleavable. In another such aspect, the compound is directly linked to the antibody. In one such aspect, the antibody is a multispecific antibody and the compound forms one portion of the multispecific antibody. In another such aspect, the multispecific antibody comprises a first antigen binding site which binds the BBB-R and a second antigen binding site which binds a brain antigen. In another such aspect, the brain antigen is selected from the group consisting of: beta-secretase 1 (BACE1), Abeta, epidermal growth factor receptor (EGFR), human epidermal growth factor receptor 2 (HER2), Tau, apolipoprotein E4 (ApoE4), alpha-synuclein, CD20, huntingtin, prion protein (PrP), leucine rich repeat kinase 2 (LRRK2), parkin, presenilin 1, presenilin 2, gamma secretase, death receptor 6 (DR6), amyloid precursor protein (APP), p75 neurotrophin receptor (p75NTR), interleukin 6 receptor (IL6R), TNF receptor 1 (TNFR1), interleukin 1 beta (IL1β), and caspase 6. In another such aspect, the multispecific antibody binds both TfR and BACE1. In another such aspect, the multispecific antibody binds both TfR and Abeta. In another such aspect, the multispecific antibody is labeled. In another aspect, the compound is reversibly coupled to the antibody such that the compound is released from the antibody concurrent with or after BBB transport.

It will be appreciated that any of the foregoing aspects may be applied singly or in combination with the foregoing embodiment.

In another embodiment, the invention provides a method of optimizing the pharmcokinetics and/or pharmacodynamics of a compound to be efficacious in the CNS of a subject, wherein the compound is coupled to an antibody which binds with low affinity to a BBB-R, and the antibody is selected such that its affinity for the BBB-R after coupling to the compound results in an amount of transport of the antibody conjugated to the compound across the BBB that optimizes the pharmacokinetics and/or pharmacodynamics of the compound in the CNS, wherein reduction of red blood cell levels in the subject upon compound-coupled antibody administration to the subject is decreased or eliminated. In one aspect, the BBB-R is selected from the group consisting of transferrin receptor (TfR), insulin receptor, insulin-like growth factor receptor (IGF receptor), low density lipoprotein receptor-related protein 8 (LRP8), low density lipoprotein receptor-related protein 1 (LRP1), glucose transporter 1 (Glut1) and heparin-binding epidermal growth factor-like growth factor (HB-EGF). In another such aspect, the BBB-R is a human BBB-R. In one such aspect, the BBB-R is TfR. In another such aspect, the BBB-R is TfR, and the antibody does not inhibit TfR activity. In another such aspect, the BBB-R is TfR and the antibody does not inhibit the binding of TfR to transferrin.

In another aspect, the red blood cells are immature red blood cells. In another such aspect, the immature red blood cells are reticulocytes. In another aspect, reduction of reticulocyte levels is accompanied by acute clinical symptoms. In another aspect, the method further comprises the step of monitoring the subject for depletion of red blood cells.

In another aspect, one or more properties of the antibody have been modified to reduce the impact of the antibody on reticulocyte levels and/or reduce the severity or presence of acute clinical symptoms in the subject. In one such aspect, the affinity of the antibody for the BBB-R is modified, i.e., decreased. In another such aspect, the effector function of the antibody Fc region is modified. In one such aspect, the effector function has been reduced or eliminated relative to the effector function of a wild-type antibody of the same isotype. In another such aspect, the effector function is reduced or eliminated by reduction of glycosylation of the antibody. In another such aspect, the glycosylation of the antibody is reduced by production of the antibody in an environment that does not permit wild-type glycosylation. In one such aspect, the antibody is produced in a non-mammalian cell production system. In another such aspect, the antibody is produced synthetically. In another such aspect, the glycosylation of the antibody is reduced by removal of carbohydrate groups already present on the antibody. In another such aspect, the glycosylation of the antibody is reduced by modification of the antibody such that wild-type glycosylation does not occur. In another such aspect, the Fc region of the antibody comprises a mutation at position 297 such that the wild-type asparagine residue at that position is replaced with another amino acid that interferes with glycosylation at that position. In another aspect, the effector function is reduced or eliminated by modification of the antibody isotype to an isotype that naturally has reduced or eliminated effector function.

In another aspect, the Fc region is modified to reduce or eliminate effector function. In one such aspect, the effector function is reduced or eliminated by at least one modification of the Fc region. In one such aspect, the modification is a point mutation of the Fc region to impair binding to one or more Fc receptors selected from the following positions: 238, 239, 248, 249, 252, 254, 265, 268, 269, 270, 272, 278, 289, 292, 293, 294, 295, 296, 297, 298, 301, 303, 322, 324, 327, 329, 333, 335, 338, 340, 373, 376, 382, 388, 389, 414, 416, 419, 434, 435, 437, 438, and 439. In another such aspect, the modification is elimination of some or all of the Fc region. In another such aspect, the effector function is reduced or eliminated by deletion of all or a portion of the Fc region, or by engineering the antibody such that it does not include an Fc region competent for effector function. In one such aspect, the antibody is selected from a Fab or a single chain antibody.

In another aspect, the Fc region and/or the non-Fc region of the antibody is modified to reduce or eliminate activation of the complement pathway by the antibody. In one such aspect, the modification is a point mutation of the Fc region to impair binding to C1q selected from the following positions: 270, 322, 329, and 321. In another such aspect, the modification is elimination of some or all of the Fc region. In another such aspect, complement-triggering function is reduced or eliminated by deletion of all or a portion of the Fc region, or by engineering the antibody such that it does not include an Fc region that engages the complement pathway. In one such aspect, the antibody is selected from a Fab or a single chain antibody. In another such aspect, the non-Fc region of the antibody is modified to reduce or eliminate activation of the complement pathway by the antibody. In one such aspect, the modification is a point mutation of the CH1 region to impair binding to C3. In one such aspect, the point mutation is at position 132 (see, e.g., Vidarte et al., (2001) J. Biol. Chem. 276(41): 38217-38223).

In another aspect, the dose amount and/or frequency of administration of the antibody is modulated to reduce the concentration of the antibody to which the red blood cells are exposed. In another aspect, the antibody is modified to comprise pH-sensitive binding to the BBB-R.

In another aspect, a further compound is administered in addition to the antibody and the coupled compound. In one such aspect, the further compound is responsible for or contributes to the lack of reduction of reticulocyte levels. In another aspect, the further compound inhibits or prevents the activation or activity of the complement pathway (see, e.g., Mollnes and Kirschfink (2006) Molec. Immunol. 43:107-121). In another such aspect, the further compound protects reticulocytes from antibody-related depletion. In another such aspect, the further compound supports the growth, development, or reestablishment of reticulocytes. In another aspect, the further compound is selected from erythropoietin (EPO), an iron supplement, vitamin C, folic acid and vitamin B12. In another aspect, the further compound is red blood cells or reticulocytes from the same subject. In another aspect, the further compound is red blood cells or reticulocytes from another subject.

In another aspect, the compound is a neurological disorder drug. In another aspect, the compound is an imaging agent. In another aspect, the compound is labeled. In another aspect, the antibody is labeled. In another aspect, the antibody does not impair the binding of the BBB-R to one or more of its native ligands. In another such aspect, the antibody specifically binds to TfR in such a manner that it does not inhibit binding of the TfR to transferrin. In another aspect, the BBB is in a mammal. In another such aspect, the mammal is a human. In another such aspect, the mammal has a neurological disorder. In another such aspect, the neurological disorder is selected from the group consisting of Alzheimer's disease (AD), stroke, dementia, muscular dystrophy (MD), multiple sclerosis (MS), amyotrophic lateral sclerosis (ALS), cystic fibrosis, Angelman's syndrome, Liddle syndrome, Parkinson's disease, Pick's disease, Paget's disease, cancer, and traumatic brain injury. In another aspect, the BBB is in a human.

In one aspect, the optimizing may include the generation of a series of antibody-compound complexes in which each antibody has a different affinity for the BBB-R, and assessing the pharmacokinetics and/or pharmacodynamics of each in the CNS. In another aspect, optimizing may be relative to a known standard, such as, but not limited to, the pharmacokinetics and/or pharmacodynamics of the compound when directly introduced into the CNS or when introduced to the subject in the absence of a coupled anti-BBB-R antibody.

In another aspect, the antibody has an IC50 for the BBB-R from about 1 nM to about 100 µM. In another such aspect, the IC50 is from about 5 nM to about 100 µM. In another such aspect, the IC50 is from about 50 nM to about 100 µM. In another such aspect, the IC50 is from about 100 nM to about 100 µM. In another aspect, the antibody has an affinity for the BBB-R from about 5 nM to about 50 µM. In another aspect, the antibody has an affinity for the BBB-R from about 30 nM to about 30 µM. In another such aspect, the antibody, when coupled to a compound, has an affinity for the BBB-R from about 30 nM to about 1 µM. In another such aspect, the antibody, when coupled to a compound, has an affinity for the BBB-R from about 50 nM to about 1 µM. In another such aspect, the compound-coupled antibody specifically binds to TfR and has an affinity for TfR between those affinities observed for the anti-TfR$^A$/BACE1 antibody and the anti-TfR$^E$/BACE1 antibody. In another such aspect, the compound-coupled antibody specifically binds to TfR and has an affinity for TfR between those affinities observed for the anti-TfR$^D$/BACE1 antibody and the anti-TfR$^E$/BACE1 antibody. In another such aspect, the compound-coupled antibody specifically binds to TfR and has an IC50 for TfR between those IC50s observed for the anti-TfR$^A$/BACE1 antibody and the anti-TfR$^E$/BACE1 antibody. In another such aspect, the compound-coupled antibody specifically binds to TfR and has an IC50 for TfR between those IC50s observed for the anti-TfR$^D$/BACE1 antibody and the anti-TfR$^E$/BACE1 antibody. In one aspect, the affinity of the anti-BBB-R or anti-BBB-R/compound for the BBB-R is measured using scatchard analysis. In another aspect, the affinity of the anti-BBB-R or anti-BBB-R/compound for the BBB-R is measured using BIACORE analysis. In another aspect, the affinity of the anti-BBB-R or anti-BBB-R/compound for the BBB-R is measured using a competition ELISA.

In another aspect, the dissociation half-life of the antibody from the BBB-R to which it specifically binds is from about 30 seconds to about 30 minutes. In another such aspect, the dissociation half-life is from about 30 seconds to about 20 minutes. In another such aspect, the dissociation half-life is from about 30 seconds to about 10 minutes. In another such aspect, the dissociation half-life is from about 30 seconds to about 5 minutes. In another such aspect, the dissociation half-life is from about 30 seconds to about 3 minutes. In another such aspect, the dissociation half-life is from about 30 seconds to about 2 minutes. In another such aspect, the dissociation half-life is about two minutes. In another such aspect, the dissociation half-life is one minute or less. In another such aspect, the compound-coupled antibody specifically binds to TfR and has a dissociation half-life for TfR between those dissociation half-lives observed for the anti-TfR$^A$/BACE1 antibody and the anti-TfR$^E$/BACE1 antibody from their respective binding to TfR. In another such aspect, the compound-coupled antibody specifically binds to TfR and has a dissociation half-life for TfR between those dissociation half-lives observed for the anti-TfR$^D$/BACE1 antibody and the anti-TfR$^E$/BACE1 antibody from their respective binding to TfR. In another aspect, the dissociation half-life of the anti-BBB-R or anti-BBB-R/compound for the BBB-R is measured using BIACORE analysis. In another aspect, the dissociation half-life of the anti-BBB-R or anti-BBB-R/compound for the BBB-R is measured using a competition binding assay, such as a competition ELISA.

In another aspect, the compound-coupled antibody is administered at a therapeutic dose. In one such aspect, the therapeutic dose is a dose that saturates the BBB-R to which the antibody specifically binds. In another such aspect, the compound-coupled antibody is administered at a dose and dose frequency that minimizes red blood cell interaction with the compound-coupled antibody while still facilitating compound delivery across the BBB into the CNS at therapeutic levels.

In another aspect, the compound is covalently coupled to the antibody. In one such aspect, the compound is joined to the antibody by a linker. In one such aspect, the linker is cleavable. In another such aspect, the linker is not cleavable. In another such aspect, the compound is directly linked to the antibody. In one such aspect, the antibody is a multispecific antibody and the compound forms one portion of the multispecific antibody. In another such aspect, the multispecific antibody comprises a first antigen binding site which binds the BBB-R and a second antigen binding site which binds a brain antigen. In another such aspect, the brain antigen is selected from the group consisting of: beta-secretase 1 (BACE1), Abeta, epidermal growth factor receptor (EGFR), human epidermal growth factor receptor 2 (HER2), Tau, apolipoprotein E4 (ApoE4), alpha-synuclein, CD20, huntingtin, prion protein (PrP), leucine rich repeat kinase 2 (LRRK2), parkin, presenilin 1, presenilin 2, gamma secretase, death receptor 6 (DR6), amyloid precursor protein (APP), p75 neurotrophin receptor (p75NTR), interleukin 6 receptor (IL6R), TNF receptor 1 (TNFR1), interleukin 1 beta (IL1β), and caspase 6. In another such aspect, the multispecific antibody binds both TfR and BACE1. In another such aspect, the multispecific antibody binds both TfR and Abeta. In another such aspect, the multispecific antibody is labeled. In another aspect, the compound is reversibly coupled to the antibody such that the compound is released from the antibody concurrent with or after BBB transport.

It will be appreciated that any of the foregoing aspects may be applied singly or in combination with the foregoing embodiment.

In another embodiment the invention provides a method of treating a neurological disorder in a mammal comprising treating the mammal with an antibody that binds a BBB-R and is coupled to a compound, wherein the antibody has been selected to have a low affinity for the BBB-R and thereby improves CNS uptake of the antibody and coupled compound, and wherein reduction of red blood cell levels in the subject upon compound-coupled antibody administration to the subject is decreased or eliminated. In one aspect, the BBB-R is selected from the group consisting of transferrin receptor (TfR), insulin receptor, insulin-like growth factor receptor (IGF receptor), low density lipoprotein receptor-related protein 8 (LRP8), low density lipoprotein receptor-related protein 1 (LRP1), glucose transporter 1 (Glut1) and heparin-binding epidermal growth factor-like growth factor (HB-EGF). In another such aspect, the BBB-R is a human BBB-R. In one such aspect, the BBB-R is TfR. In another such aspect, the BBB-R is TfR, and the antibody does not inhibit TfR activity. In another such aspect, the BBB-R is TfR and the antibody does not inhibit the binding of TfR to transferrin.

In another aspect, the red blood cells are immature red blood cells. In another such aspect, the immature red blood cells are reticulocytes. In another aspect, reduction of reticulocyte levels is accompanied by acute clinical symptoms. In another aspect, the method further comprises the step of monitoring the subject for depletion of red blood cells.

In another aspect, one or more properties of the antibody have been modified to reduce the impact of the antibody on reticulocyte levels and/or reduce the severity or presence of acute clinical symptoms in the subject. In one such aspect, the affinity of the antibody for the BBB-R is modified, i.e., decreased. In another such aspect, the effector function of the antibody Fc region is modified. In one such aspect, the effector function has been reduced or eliminated relative to the effector function of a wild-type antibody of the same isotype. In another such aspect, the effector function is reduced or eliminated by reduction of glycosylation of the antibody. In another such aspect, the glycosylation of the antibody is reduced by production of the antibody in an environment that does not permit wild-type glycosylation. In one such aspect, the antibody is produced in a non-mammalian cell production system. In another such aspect, the antibody is produced synthetically. In another such aspect, the glycosylation of the antibody is reduced by removal of carbohydrate groups already present on the antibody. In another such aspect, the glycosylation of the antibody is reduced by modification of the antibody such that wild-type glycosylation does not occur. In another such aspect, the Fc region of the antibody comprises a mutation at position 297 such that the wild-type asparagine residue at that position is replaced with another amino acid that interferes with glycosylation at that position. In another aspect, the effector function is reduced or eliminated by modification of the antibody isotype to an isotype that naturally has reduced or eliminated effector function.

In another aspect, the Fc region is modified to reduce or eliminate effector function. In one such aspect, the effector function is reduced or eliminated by at least one modification of the Fc region. In one such aspect, the modification is a point mutation of the Fc region to impair binding to one or more Fc receptors selected from the following positions: 238, 239, 248, 249, 252, 254, 265, 268, 269, 270, 272, 278, 289, 292, 293, 294, 295, 296, 297, 298, 301, 303, 322, 324, 327, 329, 333, 335, 338, 340, 373, 376, 382, 388, 389, 414, 416, 419, 434, 435, 437, 438, and 439. In another such aspect, the modification is elimination of some or all of the Fc region. In another such aspect, the effector function is reduced or eliminated by deletion of all or a portion of the Fc region, or by engineering the antibody such that it does not include an Fc region competent for effector function. In one such aspect, the antibody is selected from a Fab or a single chain antibody.

In another aspect, the dose amount and/or frequency of administration of the antibody is modulated to reduce the concentration of the antibody to which the red blood cells are exposed. In another aspect, the antibody is modified to comprise pH-sensitive binding to the BBB-R.

In another aspect, a further compound is administered in addition to the antibody and the coupled compound. In one such aspect, the further compound is responsible for or contributes to the lack of reduction of reticulocyte levels. In another such aspect, the further compound inhibits or prevents the activation or activity of the complement pathway (see, e.g., Mollnes and Kirschfink (2006) Molec. Immunol. 43:107-121). In another such aspect, the further compound protects reticulocytes from antibody-related depletion. In another such aspect, the further compound supports the growth, development, or reestablishment of reticulocytes. In another aspect, the further compound is selected from erythropoietin (EPO), an iron supplement, vitamin C, folic acid and vitamin B12. In another aspect, the further compound is red blood cells or reticulocytes from the same subject. In another aspect, the further compound is red blood cells or reticulocytes from another subject.

In another aspect, the compound is a neurological disorder drug. In another aspect, the compound is an imaging agent. In another aspect, the compound is labeled. In another aspect, the antibody is labeled. In another aspect, the antibody does not impair the binding of the BBB-R to one or more of its native ligands. In another such aspect, the antibody specifically binds to TfR in such a manner that it does not inhibit binding of the TfR to transferrin. In one aspect, the mammal is a human. In another such aspect, the mammal has a neurological disorder. In another such aspect, the neurological disorder is selected from the group consisting of Alzheimer's disease (AD), stroke, dementia, muscular dystrophy (MD), multiple sclerosis (MS), amyotrophic lateral sclerosis (ALS), cystic fibrosis, Angelman's syndrome, Liddle syndrome, Parkinson's disease, Pick's disease, Paget's disease, cancer, and traumatic brain injury.

In one aspect, the treating results in lessening or elimination of disorder symptoms. In another aspect, the treating results in amelioration of the neurological disorder.

In another aspect, the antibody has an IC50 for the BBB-R from about 1 nM to about 100 µM. In another such aspect, the IC50 is from about 5 nM to about 100 µM. In another such aspect, the IC50 is from about 50 nM to about 100 µM. In another such aspect, the IC50 is from about 100 nM to about 100 µM. In another aspect, the antibody has an affinity for the BBB-R from about 5 nM to about 50 µM. In another aspect, the antibody has an affinity for the BBB-R from about 30 nM to about 30 µM. In another such aspect, the antibody, when coupled to a compound, has an affinity for the BBB-R from about 30 nM to about 1 µM. In another such aspect, the antibody, when coupled to a compound, has an affinity for the BBB-R from about 50 nM to about 1 µM. In another such aspect, the compound-coupled antibody specifically binds to TfR and has an affinity for TfR between those affinities observed for the anti-TfR$^A$/BACE1 antibody and the anti-TfR$^E$/BACE1 antibody. In another such aspect, the compound-coupled antibody specifically binds to TfR and has an affinity for TfR between those affinities observed for the anti-TfR$^D$/BACE1 antibody and the anti-TfR$^E$/BACE1 antibody. In another such aspect, the compound-coupled antibody specifically binds to TfR and has an IC50 for TfR between those IC50s observed for the anti-TfR$^A$/BACE1 antibody and the anti-TfR$^E$/BACE1 antibody. In another such aspect, the compound-coupled antibody specifically binds to TfR and has an IC50 for TfR between those IC50s observed for the anti-TfR$^D$/BACE1 antibody and the anti-TfR$^E$/BACE1 antibody. In one aspect, the affinity of the anti-BBB-R or anti-BBB-R/compound for the BBB-R is measured using scatchard analysis. In another aspect, the affinity of the anti-BBB-R or anti-BBB-R/compound for the BBB-R is measured using BIACORE analysis. In another aspect, the affinity of the anti-BBB-R or anti-BBB-R/compound for the BBB-R is measured using a competition ELISA.

In another aspect, the dissociation half-life of the antibody from the BBB-R to which it specifically binds is from about 30 seconds to about 30 minutes. In another such aspect, the dissociation half-life is from about 30 seconds to about 20 minutes. In another such aspect, the dissociation half-life is from about 30 seconds to about 10 minutes. In another such aspect, the dissociation half-life is from about 30 seconds to about 5 minutes. In another such aspect, the dissociation half-life is from about 30 seconds to about 3 minutes. In another such aspect, the dissociation half-life is from about 30 seconds to about 2 minutes. In another such aspect, the dissociation half-life is about two minutes. In another such aspect, the dissociation half-life is one minute or less. In another such aspect, the compound-coupled antibody specifically binds to TfR and has a dissociation half-life for TfR between those dissociation half-lives observed for the anti-TfR$^A$/BACE1 antibody and the anti-TfR$^E$/BACE1 antibody from their respective binding to TfR. In another such aspect, the compound-coupled antibody specifically binds to TfR and has a dissociation half-life for TfR between those dissociation half-lives observed for the anti-TfR$^D$/BACE1 antibody and the anti-TfR$^E$/BACE1 antibody from their respective binding to TfR. In another aspect, the dissociation half-life of the anti-BBB-R or anti-BBB-R/compound for the BBB-R is measured using BIACORE analysis. In another aspect, the dissociation half-life of the anti-BBB-R or anti-BBB-R/compound for the BBB-R is measured using a competition binding assay, such as a competition ELISA.

In another aspect, the compound-coupled antibody is administered at a therapeutic dose. In one such aspect, the therapeutic dose is a dose that saturates the BBB-R to which the antibody specifically binds. In another such aspect, the compound-coupled antibody is administered at a dose and dose frequency that minimizes red blood cell interaction with the compound-coupled antibody while still facilitating compound delivery across the BBB into the CNS at therapeutic levels.

In another aspect, the compound is covalently coupled to the antibody. In one such aspect, the compound is joined to the antibody by a linker. In one such aspect, the linker is cleavable. In another such aspect, the linker is not cleavable. In another such aspect, the compound is directly linked to the antibody. In one such aspect, the antibody is a multispecific antibody and the compound forms one portion of the multispecific antibody. In another such aspect, the multispecific antibody comprises a first antigen binding site which binds the BBB-R and a second antigen binding site which binds a brain antigen. In another such aspect, the brain antigen is selected from the group consisting of: beta-secretase 1 (BACE1), Abeta, epidermal growth factor receptor (EGFR), human epidermal growth factor receptor 2 (HER2), Tau, apolipoprotein E4 (ApoE4), alpha-synuclein, CD20, huntingtin, prion protein (PrP), leucine rich repeat kinase 2 (LRRK2), parkin, presenilin 1, presenilin 2, gamma secretase, death receptor 6 (DR6), amyloid precursor protein (APP), p75 neurotrophin receptor (p75NTR), interleukin 6 receptor (IL6R), TNF receptor 1 (TNFR1), interleukin 1 beta (IL1β), and caspase 6. In another such aspect, the multispecific antibody binds both TfR and BACE1. In another such aspect, the multispecific antibody binds both TfR and Abeta. In another such aspect, the multispecific antibody is labeled. In another aspect, the compound is reversibly coupled to the antibody such that the compound is released from the antibody concurrent with or after BBB transport.

It will be appreciated that any of the foregoing aspects may be applied singly or in combination with the foregoing embodiment.

In another embodiment, the invention provides a method of improving the safety in a subject of an antibody that binds a BBB-R comprising modifying one or more properties of the antibody such that administration of the antibody decreases or eliminates reduction of red blood cell levels in the subject observed upon administration of the unmodified antibody. In one aspect, the BBB-R is selected from the group consisting of transferrin receptor (TfR), insulin receptor, insulin-like growth factor receptor (IGF receptor), low density lipoprotein receptor-related protein 8 (LRP8), low density lipoprotein receptor-related protein 1 (LRP1), glucose transporter 1 (Glut1) and heparin-binding epidermal growth factor-like growth factor (HB-EGF). In another such aspect, the BBB-R is a human BBB-R. In one such aspect, the BBB-R is TfR. In another such aspect, the BBB-R is TfR, and the antibody does not inhibit TfR activity. In another such aspect, the BBB-R is TfR and the antibody does not inhibit the binding of TfR to transferrin.

In another aspect, the red blood cells are immature red blood cells. In another such aspect, the immature red blood cells are reticulocytes. In another aspect, reduction of reticulocyte levels is accompanied by acute clinical symptoms.

In another aspect, one or more properties of the antibody have been modified to reduce the impact of the antibody on reticulocyte levels and/or reduce the severity or presence of acute clinical symptoms in the subject. In one such aspect, the affinity of the antibody for the BBB-R is modified, i.e., decreased. In another such aspect, the modification of the affinity of the antibody is measured relative to a wild-type antibody of the same isotype not having modified (i.e., decreased) affinity for the BBB-R. In another such aspect, the effector function of the antibody Fc region is modified. In one such aspect, the effector function has been reduced or eliminated relative to the effector function of a wild-type antibody of the same isotype. In another such aspect, the effector function is reduced or eliminated by reduction of glycosylation of the antibody. In another such aspect, the glycosylation of the antibody is reduced by production of the antibody in an environment that does not permit wild-type glycosylation. In one such aspect, the antibody is produced in a non-mammalian cell production system. In another such aspect, the antibody is produced synthetically. In another such aspect, the glycosylation of the antibody is reduced by removal of carbohydrate groups already present on the antibody. In another such aspect, the glycosylation of the antibody is reduced by modification of the antibody such that wild-type glycosylation does not occur. In another such aspect, the Fc region of the antibody comprises a mutation at position 297 such that the wild-type asparagine residue at that position is replaced with another amino acid that interferes with glycosylation at that position. In another aspect, the effector function is reduced or eliminated by modification of the antibody isotype to an isotype that naturally has reduced or eliminated effector function.

In another aspect, the Fc region is modified to reduce or eliminate effector function. In one such aspect, the effector function is reduced or eliminated by at least one modification of the Fc region. In one such aspect, the modification is a point mutation of the Fc region to impair binding to one or more Fc receptors selected from the following positions: 238, 239, 248, 249, 252, 254, 265, 268, 269, 270, 272, 278, 289, 292, 293, 294, 295, 296, 297, 298, 301, 303, 322, 324, 327, 329, 333, 335, 338, 340, 373, 376, 382, 388, 389, 414, 416, 419, 434, 435, 437, 438, and 439. In another such aspect, the modification is elimination of some or all of the Fc region. In another such aspect, the effector function is reduced or eliminated by deletion of all or a portion of the Fc region, or by engineering the antibody such that it does not include an Fc region competent for effector function. In one such aspect, the antibody is selected from a Fab or a single chain antibody.

In another aspect, the Fc region and/or the non-Fc region of the antibody is modified to reduce or eliminate activation of the complement pathway by the antibody. In one such aspect, the modification is a point mutation of the Fc region to impair binding to C1q selected from the following positions: 270, 322, 329, and 321. In another such aspect, the modification is elimination of some or all of the Fc region. In another such aspect, complement-triggering function is reduced or eliminated by deletion of all or a portion of the Fc region, or by engineering the antibody such that it does not include an Fc region that engages the complement pathway. In one such aspect, the antibody is selected from a Fab or a single chain antibody. In another such aspect, the non-Fc region of the antibody is modified to reduce or eliminate activation of the complement pathway by the antibody. In one such aspect, the modification is a point mutation of the CH1 region to impair binding to C3. In one such aspect, the point mutation is at position 132 (see, e.g., Vidarte et al., (2001) J. Biol. Chem. 276(41): 38217-38223).

In another aspect, the dose amount and/or frequency of administration of the antibody is modulated to reduce the concentration of the antibody to which the red blood cells are exposed. In another aspect, the antibody is modified to comprise pH-sensitive binding to the BBB-R.

In another aspect, the antibody is coupled with a therapeutic compound. In another such aspect, the compound is a neurological disorder drug. In another aspect, the compound is an imaging agent. In another aspect, the compound is labeled. In another aspect, the antibody is labeled. In another aspect, the antibody does not impair the binding of the BBB-R to one or more of its native ligands. In another such aspect, the antibody specifically binds to TfR in such a manner that it does not inhibit binding of the TfR to transferrin. In another aspect, the BBB is in a mammal. In another such aspect, the mammal is a human. In another such aspect, the mammal has a neurological disorder. In another such aspect, the neurological disorder is selected from the group consisting of Alzheimer's disease (AD), stroke, dementia, muscular dystrophy (MD), multiple sclerosis (MS), amyotrophic lateral sclerosis (ALS), cystic fibrosis, Angelman's syndrome, Liddle syndrome, Parkinson's disease, Pick's disease, Paget's disease, cancer, and traumatic brain injury. In another aspect, the BBB is in a human.

In another aspect, the antibody has an IC50 for the BBB-R from about 1 nM to about 100 μM. In another such aspect, the IC50 is from about 5 nM to about 100 μM. In another such aspect, the IC50 is from about 50 nM to about 100 μM. In another such aspect, the IC50 is from about 100 nM to about 100 μM. In another aspect, the antibody has an affinity for the BBB-R from about 5 nM to about 50 μM. In another aspect, the antibody has an affinity for the BBB-R from about 30 nM to about 30 μM. In another such aspect, the antibody, when coupled to a compound, has an affinity for the BBB-R from about 30 nM to about 1 μM. In another such aspect, the antibody, when coupled to a compound, has an affinity for the BBB-R from about 50 nM to about 1 μM. In another such aspect, the compound-coupled antibody specifically binds to TfR and has an affinity for TfR between those affinities observed for the anti-TfR$^A$/BACE1 antibody and the anti-TfR$^E$/BACE1 antibody. In another such aspect, the compound-coupled antibody specifically binds to TfR and has an affinity for TfR between those affinities observed for the anti-TfR$^D$/BACE1 antibody and the anti-TfR$^E$/BACE1 antibody. In another such aspect, the compound-coupled antibody specifically binds to TfR and has an IC50 for TfR between those IC50s observed for the anti-TfR$^A$/BACE1 antibody and the anti-TfR$^E$/BACE1 antibody. In another such aspect, the compound-coupled antibody specifically binds to TfR and has an IC50 for TfR between those IC50s observed for the anti-TfR$^D$/BACE1 antibody and the anti-TfR$^E$/BACE1 antibody. In one aspect, the affinity of the anti-BBB-R or anti-BBB-R/compound for the BBB-R is measured using scatchard analysis. In another aspect, the affinity of the anti-BBB-R or anti-BBB-R/compound for the BBB-R is measured using BIACORE analysis. In another aspect, the affinity of the anti-BBB-R or anti-BBB-R/compound for the BBB-R is measured using a competition ELISA.

In another aspect, the dissociation half-life of the antibody from the BBB-R to which it specifically binds is from about 30 seconds to about 30 minutes. In another such aspect, the dissociation half-life is from about 30 seconds to about 20 minutes. In another such aspect, the dissociation half-life is from about 30 seconds to about 10 minutes. In another such aspect, the dissociation half-life is from about 30 seconds to about 5 minutes. In another such aspect, the dissociation half-life is from about 30 seconds to about 3 minutes. In another such aspect, the dissociation half-life is from about 30 seconds to about 2 minutes. In another such aspect, the dissociation half-life is about two minutes. In another such aspect, the dissociation half-life is one minute or less. In another such aspect, the compound-coupled antibody specifically binds to TfR and has a dissociation half-life for TfR between those dissociation half-lives observed for the anti-TfR$^A$/BACE1 antibody and the anti-TfR$^E$/BACE1 antibody from their respective binding to TfR. In another such aspect, the compound-coupled antibody specifically binds to TfR and has a dissociation half-life for TfR between those dissociation half-lives observed for the anti-TfR$^D$/BACE1 antibody and the anti-TfR$^E$/BACE1 antibody from their respective binding to TfR. In another aspect, the dissociation half-life of the anti-BBB-R or anti-BBB-R/compound for the BBB-R is measured using BIACORE analysis. In another aspect, the dissociation half-life of the anti-BBB-R or anti-BBB-R/compound for the BBB-R is measured using a competition binding assay, such as a competition ELISA.

In another aspect, the antibody is selected from a panel of antibodies based upon the affinity of the selected antibody. In another aspect, the antibody is engineered to have the desired affinity. In one such aspect, the antibody is generated using any art-known protein engineering methodology including, but not limited to, phage display, yeast display, random mutagenesis, and site-directed mutagenesis.

In another aspect, the compound-coupled antibody is administered at a therapeutic dose. In one such aspect, the therapeutic dose is a dose that saturates the BBB-R to which the antibody specifically binds. In another such aspect, the compound-coupled antibody is administered at a dose and dose frequency that minimizes red blood cell interaction with the compound-coupled antibody while still facilitating compound delivery across the BBB into the CNS at therapeutic levels.

In another aspect, the compound is covalently coupled to the antibody. In one such aspect, the compound is joined to the antibody by a linker. In one such aspect, the linker is cleavable. In another such aspect, the linker is not cleavable. In another such aspect, the compound is directly linked to the antibody. In one such aspect, the antibody is a multispecific antibody and the compound forms one portion of the multispecific antibody. In another such aspect, the multispecific antibody comprises a first antigen binding site which binds the BBB-R and a second antigen binding site which binds a brain antigen. In another such aspect, the brain antigen is selected from the group consisting of: beta-secretase 1 (BACE1), Abeta, epidermal growth factor receptor (EGFR), human epidermal growth factor receptor 2 (HER2), Tau, apolipoprotein E4 (ApoE4), alpha-synuclein, CD20, huntingtin, prion protein (PrP), leucine rich repeat kinase 2 (LRRK2), parkin, presenilin 1, presenilin 2, gamma secretase, death receptor 6 (DR6), amyloid precursor protein (APP), p75 neurotrophin receptor (p75NTR), interleukin 6 receptor (IL6R), TNF receptor 1 (TNFR1), interleukin 1 beta (IL1β), and caspase 6. In another such aspect, the multispecific antibody binds both TfR and BACE1. In another such aspect, the multispecific antibody binds both TfR and Abeta. In another such aspect, the multispecific antibody is labeled. In another aspect, the compound is reversibly coupled to the antibody such that the compound is released from the antibody concurrent with or after BBB transport.

It will be appreciated that any of the foregoing aspects may be applied singly or in combination with the foregoing embodiment.

In another embodiment, the invention provides a method of making an antibody useful for transporting a compound across the BBB with improved safety comprising selecting an antibody specific for a blood-brain barrier receptor (BBB-R) that has a desirably low affinity for the BBB-R, and modifying one or more properties of the antibody such that administration of the antibody decreases or eliminates reduction of red blood cell levels in the subject observed upon administration of an unmodified antibody. In one aspect, the BBB-R is selected from the group consisting of transferrin receptor (TfR), insulin receptor, insulin-like growth factor receptor (IGF receptor), low density lipoprotein receptor-related protein 8 (LRP8), low density lipoprotein receptor-related protein 1 (LRP1), glucose transporter 1 (Glut1) and heparin-binding epidermal growth factor-like growth factor (HB-EGF). In another aspect, the BBB-R is a human BBB-R. In one such aspect, the BBB-R is TfR. In another such aspect, the BBB-R is TfR, and the antibody does not inhibit TfR activity. In another such aspect, the BBB-R is TfR and the antibody does not inhibit the binding of TfR to transferrin.

In another aspect, the red blood cells are immature red blood cells. In another such aspect, the immature red blood cells are reticulocytes. In another aspect, reduction of reticulocyte levels is accompanied by acute clinical symptoms.

In another aspect, one or more properties of the antibody have been modified to reduce the impact of the antibody on reticulocyte levels and/or reduce the severity or presence of acute clinical symptoms in the subject. In one such aspect, the affinity of the antibody for the BBB-R is modified, i.e., decreased. In another such aspect, the modification of the affinity of the antibody is measured relative to a wild-type antibody of the same isotype not having modified (i.e., decreased) affinity for the BBB-R. In another such aspect, the effector function of the antibody Fc region is modified. In one such aspect, the effector function has been reduced or eliminated relative to the effector function of a wild-type antibody of the same isotype. In another such aspect, the effector function is reduced or eliminated by reduction of glycosylation of the antibody. In another such aspect, the glycosylation of the antibody is reduced by production of the antibody in an environment that does not permit wild-type glycosylation. In one such aspect, the antibody is produced in a non-mammalian cell production system. In another such aspect, the antibody is produced synthetically. In another such aspect, the glycosylation of the antibody is reduced by removal of carbohydrate groups already present on the antibody. In another such aspect, the glycosylation of the antibody is reduced by modification of the antibody such that wild-type glycosylation does not occur. In another such aspect, the Fc region of the antibody comprises a mutation at position 297 such that the wild-type asparagine residue at that position is replaced with another amino acid that interferes with glycosylation at that position. In another aspect, the effector function is reduced or eliminated by modification of the antibody isotype to an isotype that naturally has reduced or eliminated effector function.

In another aspect, the Fc region is modified to reduce or eliminate effector function. In one such aspect, the effector function is reduced or eliminated by at least one modification of the Fc region. In one such aspect, the modification is a point mutation of the Fc region to impair binding to one or more Fc receptors selected from the following positions: 238, 239, 248, 249, 252, 254, 265, 268, 269, 270, 272, 278, 289, 292, 293, 294, 295, 296, 297, 298, 301, 303, 322, 324, 327, 329, 333, 335, 338, 340, 373, 376, 382, 388, 389, 414, 416, 419, 434, 435, 437, 438, and 439. In another such aspect, the modification is elimination of some or all of the Fc region. In another such aspect, the effector function is reduced or eliminated by deletion of all or a portion of the Fc region, or by engineering the antibody such that it does not include an Fc region competent for effector function. In one such aspect, the antibody is selected from a Fab or a single chain antibody.

In another aspect, the Fc region and/or the non-Fc region of the antibody is modified to reduce or eliminate activation of the complement pathway by the antibody. In one such aspect, the modification is a point mutation of the Fc region to impair binding to C1q selected from the following positions: 270, 322, 329, and 321. In another such aspect, the modification is elimination of some or all of the Fc region. In another such aspect, complement-triggering function is reduced or eliminated by deletion of all or a portion of the Fc region, or by engineering the antibody such that it does not include an Fc region that engages the complement pathway. In one such aspect, the antibody is selected from a Fab or a single chain antibody. In another such aspect, the non-Fc region of the antibody is modified to reduce or eliminate activation of the complement pathway by the antibody. In one such aspect, the modification is a point mutation of the CH1 region to impair binding to C3. In one such aspect, the point mutation is at position 132 (see, e.g., Vidarte et al., (2001) J. Biol. Chem. 276(41): 38217-38223).

In another aspect, the dose amount and/or frequency of administration of the antibody is modulated to reduce the concentration of the antibody to which the red blood cells are exposed. In another aspect, the antibody is modified to comprise pH-sensitive binding to the BBB-R.

In another aspect, the antibody is coupled with a therapeutic compound. In another such aspect, the compound is a neurological disorder drug. In another aspect, the compound is an imaging agent. In another aspect, the compound is labeled. In another aspect, the antibody is labeled. In another aspect, the antibody does not impair the binding of the BBB-R to one or more of its native ligands. In another such aspect, the antibody specifically binds to TfR in such a manner that it does not inhibit binding of the TfR to transferrin. In another aspect, the BBB is in a mammal. In another such aspect, the mammal is a human. In another such aspect, the mammal has a neurological disorder. In another such aspect, the neurological disorder is selected from the group consisting of Alzheimer's disease (AD), stroke, dementia, muscular dystrophy (MD), multiple sclerosis (MS), amyotrophic lateral sclerosis (ALS), cystic fibrosis, Angelman's syndrome, Liddle syndrome, Parkinson's disease, Pick's disease, Paget's disease, cancer, and traumatic brain injury. In another aspect, the BBB is in a human.

In another aspect, the antibody has an IC50 for the BBB-R from about 1 nM to about 100 μM. In another such aspect, the IC50 is from about 5 nM to about 100 μM. In another such aspect, the IC50 is from about 50 nM to about 100 μM. In another such aspect, the IC50 is from about 100 nM to about 100 μM. In another aspect, the antibody has an affinity for the BBB-R from about 5 nM to about 50 μM. In another aspect, the antibody has an affinity for the BBB-R from about 30 nM to about 30 μM. In another such aspect, the antibody, when coupled to a compound, has an affinity for the BBB-R from about 30 nM to about 1 μM. In another such aspect, the antibody, when coupled to a compound, has an affinity for the BBB-R from about 50 nM to about 1 μM. In another such aspect, the compound-coupled antibody specifically binds to TfR and has an affinity for TfR between those affinities observed for the anti-TfR$^A$/BACE1 antibody and the anti-TfR$^E$/BACE1 antibody. In another such aspect, the compound-coupled antibody specifically binds to TfR and has an affinity for TfR between those affinities observed for the anti-TfR$^D$/BACE1 antibody and the anti-TfR$^E$/BACE1 antibody. In another such aspect, the compound-coupled antibody specifically binds to TfR and has an IC50 for TfR between those IC50s observed for the anti-TfR$^A$/BACE1 antibody and the anti-TfR$^E$/BACE1 antibody. In another such aspect, the compound-coupled antibody specifically binds to TfR and has an IC50 for TfR between those IC50s observed for the anti-TfR$^D$/BACE1 antibody and the anti-TfR$^E$/BACE1 antibody. In one aspect, the affinity of the anti-BBB-R or anti-BBB-R/compound for the BBB-R is measured using scatchard analysis.

In another aspect, the affinity of the anti-BBB-R or anti-BBB-R/compound for the BBB-R is measured using BIACORE analysis. In another aspect, the affinity of the anti-BBB-R or anti-BBB-R/compound for the BBB-R is measured using a competition ELISA.

In another aspect, the dissociation half-life of the antibody from the BBB-R to which it specifically binds is from about 30 seconds to about 30 minutes. In another such aspect, the dissociation half-life is from about 30 seconds to about 20 minutes. In another such aspect, the dissociation half-life is from about 30 seconds to about 10 minutes. In another such aspect, the dissociation half-life is from about 30 seconds to about 5 minutes. In another such aspect, the dissociation half-life is from about 30 seconds to about 3 minutes. In another such aspect, the dissociation half-life is from about 30 seconds to about 2 minutes. In another such aspect, the dissociation half-life is about two minutes. In another such aspect, the dissociation half-life is one minute or less. In another such aspect, the compound-coupled antibody specifically binds to TfR and has a dissociation half-life for TfR between those dissociation half-lives observed for the anti-TfR$^A$/BACE1 antibody and the anti-TfR$^E$/BACE1 antibody from their respective binding to TfR. In another such aspect, the compound-coupled antibody specifically binds to TfR and has a dissociation half-life for TfR between those dissociation half-lives observed for the anti-TfR$^D$/BACE1 antibody and the anti-TfR$^E$/BACE1 antibody from their respective binding to TfR. In another aspect, the dissociation half-life of the anti-BBB-R or anti-BBB-R/compound for the BBB-R is measured using BIACORE analysis. In another aspect, the dissociation half-life of the anti-BBB-R or anti-BBB-R/compound for the BBB-R is measured using a competition binding assay, such as a competition ELISA.

In another aspect, the antibody is selected from a panel of antibodies based upon the affinity of the selected antibody. In another aspect, the antibody is engineered to have the desired affinity. In one such aspect, the antibody is generated using any art-known protein engineering methodology including, but not limited to, phage display, yeast display, random mutagenesis, and site-directed mutagenesis.

In another aspect, the compound-coupled antibody is administered at a therapeutic dose. In one such aspect, the therapeutic dose is a dose that saturates the BBB-R to which the antibody specifically binds. In another such aspect, the compound-coupled antibody is administered at a dose and dose frequency that minimizes red blood cell interaction with the compound-coupled antibody while still facilitating compound delivery across the BBB into the CNS at therapeutic levels.

In another aspect, the compound is covalently coupled to the antibody. In one such aspect, the compound is joined to the antibody by a linker. In one such aspect, the linker is cleavable. In another such aspect, the linker is not cleavable. In another such aspect, the compound is directly linked to the antibody. In one such aspect, the antibody is a multispecific antibody and the compound forms one portion of the multispecific antibody. In another such aspect, the multispecific antibody comprises a first antigen binding site which binds the BBB-R and a second antigen binding site which binds a brain antigen. In another such aspect, the brain antigen is selected from the group consisting of: beta-secretase 1 (BACE1), Abeta, epidermal growth factor receptor (EGFR), human epidermal growth factor receptor 2 (HER2), Tau, apolipoprotein E4 (ApoE4), alpha-synuclein, CD20, huntingtin, prion protein (PrP), leucine rich repeat kinase 2 (LRRK2), parkin, presenilin 1, presenilin 2, gamma secretase, death receptor 6 (DR6), amyloid precursor protein (APP), p75 neurotrophin receptor (p75NTR), interleukin 6 receptor (IL6R), TNF receptor 1 (TNFR1), interleukin 1 beta (IL1β), and caspase 6. In another such aspect, the multispecific antibody binds both TfR and BACE1. In another such aspect, the multispecific antibody binds both TfR and Abeta. In another such aspect, the multispecific antibody is labeled. In another aspect, the compound is reversibly coupled to the antibody such that the compound is released from the antibody concurrent with or after BBB transport.

It will be appreciated that any of the foregoing aspects may be applied singly or in combination with the foregoing embodiment.

In another embodiment, the invention provides an antibody which binds to a blood-brain barrier receptor (BBB-R), wherein the affinity of the antibody for the BBB-R is from about 5 nM to about 50 µM, and wherein one or more properties of the antibody have been modified to reduce at least one undesired side effect on red blood cells. In one aspect, the BBB-R is selected from the group consisting of transferrin receptor (TfR), insulin receptor, insulin-like growth factor receptor (IGF receptor), low density lipoprotein receptor-related protein 8 (LRP8), low density lipoprotein receptor-related protein 1 (LRP1), glucose transporter 1 (Glut1) and heparin-binding epidermal growth factor-like growth factor (HB-EGF). In another such aspect, the BBB-R is a human BBB-R. In one such aspect, the BBB-R is TfR. In another such aspect, the BBB-R is TfR, and the antibody does not inhibit TfR activity. In another such aspect, the BBB-R is TfR and the antibody does not inhibit the binding of TfR to transferrin.

In another aspect, the red blood cells are immature red blood cells. In another such aspect, the immature red blood cells are reticulocytes. In another aspect, reduction of reticulocyte levels is accompanied by acute clinical symptoms.

In another aspect, one or more properties of the antibody have been modified to reduce the impact of the antibody on reticulocyte levels and/or reduce the severity or presence of acute clinical symptoms in the subject. In one such aspect, the affinity of the antibody for the BBB-R is modified, i.e., decreased. In another such aspect, the modification of the affinity of the antibody is measured relative to a wild-type antibody of the same isotype not having modified (i.e., decreased) affinity for the BBB-R. In another such aspect, the effector function of the antibody Fc region is modified. In one such aspect, the effector function has been reduced or eliminated relative to the effector function of a wild-type antibody of the same isotype. In another such aspect, the effector function is reduced or eliminated by reduction of glycosylation of the antibody. In another such aspect, the glycosylation of the antibody is reduced by production of the antibody in an environment that does not permit wild-type glycosylation. In one such aspect, the antibody is produced in a non-mammalian cell production system. In another such aspect, the antibody is produced synthetically. In another such aspect, the glycosylation of the antibody is reduced by removal of carbohydrate groups already present on the antibody. In another such aspect, the glycosylation of the antibody is reduced by modification of the antibody such that wild-type glycosylation does not occur. In another such aspect, the Fc region of the antibody comprises a mutation at position 297 such that the wild-type asparagine residue at that position is replaced with another amino acid that interferes with glycosylation at that position. In another aspect, the effector function is reduced or eliminated by modification of the antibody isotype to an isotype that naturally has reduced or eliminated effector function.

In another aspect, the Fc region is modified to reduce or eliminate effector function. In one such aspect, the effector function is reduced or eliminated by at least one modification of the Fc region. In one such aspect, the modification is a point mutation of the Fc region to impair binding to one or more Fc receptors selected from the following positions: 238, 239, 248, 249, 252, 254, 265, 268, 269, 270, 272, 278, 289, 292, 293, 294, 295, 296, 297, 298, 301, 303, 322, 324, 327, 329, 333, 335, 338, 340, 373, 376, 382, 388, 389, 414, 416, 419, 434, 435, 437, 438, and 439. In another such aspect, the modification is elimination of some or all of the Fc region. In another such aspect, the effector function is reduced or eliminated by deletion of all or a portion of the Fc region, or by engineering the antibody such that it does not include an Fc region competent for effector function. In one such aspect, the antibody is selected from a Fab or a single chain antibody.

In another aspect, the Fc region and/or the non-Fc region of the antibody is modified to reduce or eliminate activation of the complement pathway by the antibody. In one such aspect, the modification is a point mutation of the Fc region to impair binding to C1q selected from the following positions: 270, 322, 329, and 321. In another such aspect, the modification is elimination of some or all of the Fc region. In another such aspect, complement-triggering function is reduced or eliminated by deletion of all or a portion of the Fc region, or by engineering the antibody such that it does not include an Fc region that engages the complement pathway. In one such aspect, the antibody is selected from a Fab or a single chain antibody. In another such aspect, the non-Fc region of the antibody is modified to reduce or eliminate activation of the complement pathway by the antibody. In one such aspect, the modification is a point mutation of the CH1 region to impair binding to C3. In one such aspect, the point mutation is at position 132 (see, e.g., Vidarte et al., (2001) J. Biol. Chem. 276(41): 38217-38223).

In another aspect, the antibody is coupled with a therapeutic compound. In another such aspect, the compound is a neurological disorder drug. In another aspect, the compound is an imaging agent. In another aspect, the compound is labeled. In another aspect, the antibody is labeled. In another aspect, the antibody does not impair the binding of the BBB-R to one or more of its native ligands. In another such aspect, the antibody specifically binds to TfR in such a manner that it does not inhibit binding of the TfR to transferrin. In another aspect, the BBB is in a mammal. In another such aspect, the mammal is a human. In another such aspect, the mammal has a neurological disorder. In another such aspect, the neurological disorder is selected from the group consisting of Alzheimer's disease (AD), stroke, dementia, muscular dystrophy (MD), multiple sclerosis (MS), amyotrophic lateral sclerosis (ALS), cystic fibrosis, Angelman's syndrome, Liddle syndrome, Parkinson's disease, Pick's disease, Paget's disease, cancer, and traumatic brain injury. In another aspect, the BBB is in a human.

In another aspect, the antibody has an IC50 for the BBB-R from about 30 nM to about 30 μM. In another such aspect, the antibody, when coupled to a compound, has an affinity for the BBB-R from about 30 nM to about 1 μM. In another such aspect, the compound-coupled antibody specifically binds to TfR and has an affinity for TfR between those affinities observed for the anti-TfR$^A$/BACE1 antibody and the anti-TfR$^E$/BACE1 antibody. In another such aspect, the compound-coupled antibody specifically binds to TfR and has an affinity for TfR between those affinities observed for the anti-TfR$^D$/BACE1 antibody and the anti-TfR$^E$/BACE1 antibody. In another such aspect, the compound-coupled antibody specifically binds to TfR and has an IC50 for TfR between those IC50s observed for the anti-TfR$^A$/BACE1 antibody and the anti-TfR$^E$/BACE1 antibody. In another such aspect, the compound-coupled antibody specifically binds to TfR and has an IC50 for TfR between those IC50s observed for the anti-TfR$^D$/BACE1 antibody and the anti-TfR$^E$/BACE1 antibody. In one aspect, the affinity of the anti-BBB-R or anti-BBB-R/compound for the BBB-R is measured using scatchard analysis. In another aspect, the affinity of the anti-BBB-R or anti-BBB-R/compound for the BBB-R is measured using BIACORE analysis. In another aspect, the affinity of the anti-BBB-R or anti-BBB-R/compound for the BBB-R is measured using a competition ELISA.

In another aspect, the dissociation half-life of the antibody from the BBB-R to which it specifically binds is from about 30 seconds to about 30 minutes. In another such aspect, the dissociation half-life is from about 30 seconds to about 20 minutes. In another such aspect, the dissociation half-life is from about 30 seconds to about 10 minutes. In another such aspect, the dissociation half-life is from about 30 seconds to about 5 minutes. In another such aspect, the dissociation half-life is from about 30 seconds to about 3 minutes. In another such aspect, the dissociation half-life is from about 30 seconds to about 2 minutes. In another such aspect, the dissociation half-life is about two minutes. In another such aspect, the dissociation half-life is one minute or less. In another such aspect, the compound-coupled antibody specifically binds to TfR and has a dissociation half-life for TfR between those dissociation half-lives observed for the anti-TfR$^A$/BACE1 antibody and the anti-TfR$^E$/BACE1 antibody from their respective binding to TfR. In another such aspect, the compound-coupled antibody specifically binds to TfR and has a dissociation half-life for TfR between those dissociation half-lives observed for the anti-TfR$^D$/BACE1 antibody and the anti-TfR$^E$/BACE1 antibody from their respective binding to TfR. In another aspect, the dissociation half-life of the anti-BBB-R or anti-BBB-R/compound for the BBB-R is measured using BIACORE analysis. In another aspect, the dissociation half-life of the anti-BBB-R or anti-BBB-R/compound for the BBB-R is measured using a competition binding assay, such as a competition ELISA.

In another aspect, the antibody is selected from a panel of antibodies based upon the affinity of the selected antibody. In another aspect, the antibody is engineered to have the desired affinity. In one such aspect, the antibody is generated using any art-known protein engineering methodology including, but not limited to, phage display, yeast display, random mutagenesis, and site-directed mutagenesis.

In another aspect, a compound is covalently coupled to the antibody. In one such aspect, the compound is joined to the antibody by a linker. In one such aspect, the linker is cleavable. In another such aspect, the linker is not cleavable. In another such aspect, the compound is directly linked to the antibody. In one such aspect, the antibody is a multispecific antibody and the compound forms one portion of the multispecific antibody. In another such aspect, the multispecific antibody comprises a first antigen binding site which binds the BBB-R and a second antigen binding site which binds a brain antigen. In another such aspect, the brain antigen is selected from the group consisting of: beta-secretase 1 (BACE1), Abeta, epidermal growth factor receptor (EGFR), human epidermal growth factor receptor 2 (HER2), Tau, apolipoprotein E4 (ApoE4), alpha-synuclein, CD20, huntingtin, prion protein (PrP), leucine rich repeat kinase 2 (LRRK2), parkin, presenilin 1, presenilin 2, gamma secretase, death receptor 6 (DR6), amyloid precursor protein (APP), p75 neurotrophin receptor (p75NTR), interleukin 6 receptor (IL6R), TNF receptor 1 (TNFR1), interleukin 1 beta (IL1β), and caspase 6. In another such aspect, the multispecific antibody binds both TfR and BACE1. In another such aspect, the multispecific antibody binds both TfR and Abeta. In another such aspect, the multispecific antibody is labeled. In another aspect, the compound is reversibly coupled to the antibody such that the compound is released from the antibody concurrent with or after BBB transport.

It will be appreciated that any of the foregoing aspects may be applied singly or in combination with the foregoing embodiment.

In another embodiment, the invention provides the use of an antibody that binds with low affinity to a BBB-R and that does not reduce red blood cell levels for the manufacture of a medicament for treating a neurological disorder. Any of the foregoing described low-affinity anti-BBB-R antibodies or any of the low-affinity anti-BBB-R antibodies described elsewhere herein may be used in the method.

In another embodiment, the invention provides an antibody that binds with low affinity to a BBB-R and that does not reduce red blood cell levels for use in treating a neurological disorder. Any of the foregoing described low-affinity anti-BBB-R antibodies or any of the low-affinity anti-BBB-R antibodies described elsewhere herein may be used in the method.

In another embodiment, the invention provides a method of transporting a therapeutic compound, such as a neurological disorder drug, across the blood-brain barrier comprising exposing the anti-BBB-R antibody coupled with a neurological disorder drug to the blood-brain barrier such that the antibody transports the neurological disorder drug coupled thereto across the blood-brain barrier, wherein the antibody does not reduce red blood cell levels.

The invention additionally provides a method of treating a neurological disorder in a mammal comprising treating the mammal with a multispecific antibody that binds both a blood-brain barrier receptor (BBB-R) and a brain antigen, wherein the anti-BBB-R antibody has been selected to have a low affinity for the BBB-R and thereby improves brain uptake of the anti-brain antigen antibody, and wherein administration of the antibody does not decrease red blood cell levels.

The invention additionally provides a method of treating a disease or disorder associated with or caused by elevated red blood cell levels in a subject comprising administering an anti-TfR antibody comprising at least partial effector function to the subject. In one aspect, the administering step is at a dose and/or dose frequency calibrated to minimize acute clinical symptoms of the antibody administration.

It will be understood that any of the foregoing methods and compositions of the invention may be combined with one another and/or with the further aspects of the invention described in the specification herein.

BRIEF DESCRIPTION OF THE FIGURES

FIGS. 1B and 1D show, respectively, mean serum and brain antibody concentrations in wild-type mice after a single 50 mg/kg intravenous injection of control IgG, anti-BACE1, or an anti-TfR/BACE1 variant (n=6 per group). FIGS. 1C and 1E show, respectively, plasma and brain concentrations of $A\beta_{1-40}$ in these same treated mice, as a marker of the activity of the injected antibody.

FIG. 2B depicts the results of experiments testing the impact of intravenously administered anti-TfR$^D$, anti-TfR$^D$/BACE1 or control IgG on the percent of the immature reticulocyte fraction from whole blood of wild-type mice at 1 hour post-dose (n=6 per group). FIG. 2C depicts the results of experiments testing the impact of intravenously administered anti-TfR$^A$/BACE1, anti-TfR$^D$/BACE1 or control IgG on total reticulocyte counts in whole blood of wild-type mice at 24 hours or 7 days post-dose (n=6 per group). All data are shown as mean±SEM. FIGS. 2D and 2E depict mean brain Abeta$_{1-40}$ concentrations in wild-type mice after a single 50 mg/kg intravenous injection of control IgG, or 5 mg/kg, 25 mg/kg or 50 mg/kg injections of anti-TfR$^D$/BACE1 (FIG. 2D) or anti-TfR$^A$/BACE1 (FIG. 2E) (n=6 per group). FIGS. 2F-2H depict the results of experiments assessing the pharmacokinetics of anti-TfR$^A$/BACE1 and anti-TfR$^D$/BACE1 in comparison with control at 5 mg/kg, 25 mg/kg or 50 mg/kg dose levels. FIG. 2F provides measurements of brain antibody concentration at the indicated time points. FIG. 2G provides measurements of plasma antibody concentration at the indicated time points. FIG. 2H provides measurements of plasma Abeta levels at the indicated time points.

FIG. 3E depicts the results of experiments assessing the effect of impairment of the complement system on the previously observed depletion of reticulocytes by anti-TfR. Wild-type or C3 knockout mice were intravenously administered 50 mg/kg of a control IgG or an anti-TfR$^D$/control IgG mixture (n=6 per group).

FIGS. 6A and 6B depict total reticulocyte counts in wild-type mice 24 hours after intravenous injection of the indicated anti-TfR/BACE1 variant antibody, compared to control IgG. FIG. 6C shows quantification of brain TfR expression level by Western blot from whole mouse brain lysates 4 days after an intravenous injection of control IgG, anti-TfR$^A$/BACE1, or anti-TfR$^D$/BACE1 at the indicated dose (n=3 per group). Quantification of TfR expression was normalized to actin and the data are shown as mean±SEM.

FIG. 7C shows a quantification of $A\beta_{1-40}$ concentrations in mouse brain after intravenous injection of control IgG or co-injection of antibodies (n=6 per group).

FIGS. 8A and 8B, respectively, depict observed plasma and brain antibody concentrations at 24 hours, 4 days and 7 days following two or four doses of antibody. It should be noted that the Y-axis scale in FIG. 8A is in µM while the Y-axis scale in FIG. 8B is in nM. The corresponding average Aβ$_{1-40}$ concentrations in plasma (FIG. 8C) and brain (FIG. 8D) were also measured. FIG. 8E shows the total reticulocyte count in mice 24 hours after the second and fourth dose, and 7 days after the fourth dose of control IgG or anti-TfR$^D$/BACE1. FIG. 8F shows a graph depicting the results of a quantification of brain TfR expression level by Western blot from whole mouse brain lysates after 4 weekly doses of control IgG or anti-TfR$^D$/BACE1. Quantification of TfR expression was normalized to actin and data are shown as mean±SEM.

FIGS. 10A to 10D provide graphs of the quantification of distinct erythrocyte subpopulations (EryA, EryB, EryC) in bone marrow following anti-TfR$^D$/BACE1 or control IgG dosing (n=6/group).

FIGS. 11A-11B show the quantification of total Ter119-positive erythrocyte populations (FIG. 11A) and TfR-positive reticulocyte populations (FIG. 11B) in blood following effectorless anti-TfR$^A$/BACE1 (Fc−) and anti-TfR$^D$/BACE1 (Fc−), full effector function anti-TfR$^D$/BACE1 (Fc+), or control IgG dosing (n=6/group). FIGS. 12A-12D provide the quantification of distinct erythrocyte subpopulations (total Ter119-positive erythrocyte lineage in FIG. 12A; EryA in FIG. 12B; EryB in FIG. 12C; and EryC in FIG. 12D) in bone marrow following dosing of effectorless anti-TfR$^A$/BACE1 (Fc−) and anti-TfR$^D$/BACE1 (Fc−), full effector function anti-TfR$^D$/BACE1 (Fc+), or control IgG dosing (n=6/group).

Figure 15B:
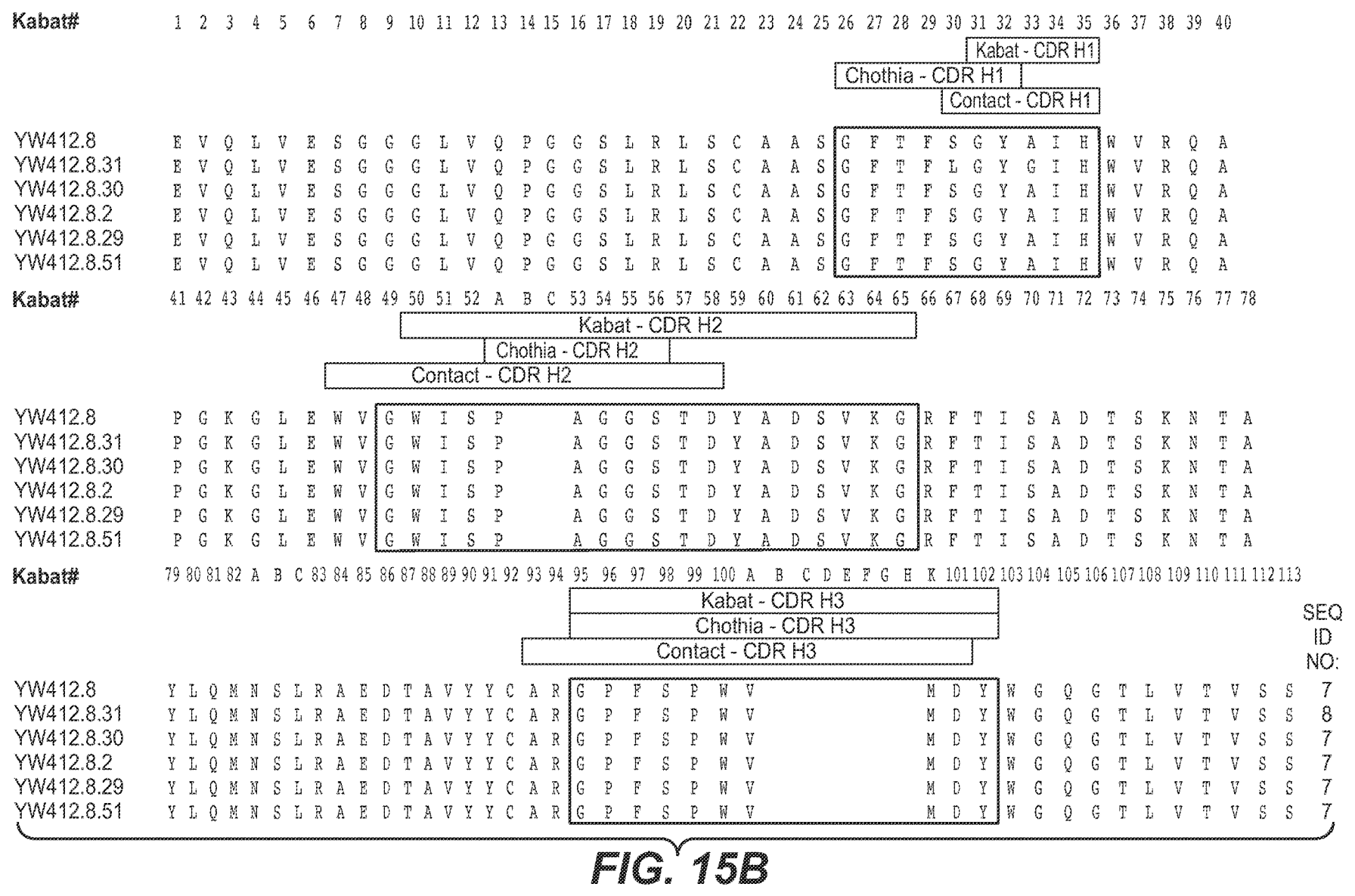

FIGS. 15A-B depict the light and heavy chain amino acid sequences of anti-BACE1 clone YW412.8 obtained from a naïve sort of the natural diversity phage display library and affinity-matured forms of YW412.8. FIG. 15A depicts the variable light (VL) sequence alignments (SEQ ID NOs. 1-6). FIG. 13B depicts the variable heavy (VH) sequence alignments (SEQ ID Nos. 7-8). In both figures, the HVR sequences for each clone are indicated by the boxed regions, with the first box indicating HVR-L1 (FIG. 15A) or HVR-H1 (FIG. 15B), the second box indicating HVR-L2 (FIG. 15A) or HVR-H2 (FIG. 15B), and the third box indicating HVR-L3 (FIG. 15A) or HVR-H3 (FIG. 15B).

FIGS. 16A-B depict the light and heavy chain amino acid sequences of anti-BACE1 antibody clone Fab 12 obtained from a naïve sort of a synthetic diversity phage display library and affinity-matured forms of Fab 12. FIG. 16A depicts the light chain sequence alignments (SEQ ID NOs. 9-12). FIG. 16B depicts the heavy chain sequence alignments (SEQ ID NO. 13). In both figures, the HVR sequences for each clone are indicated by the boxed regions, with the first box indicating HVR-L1 (FIG. 16A) or HVR-H1 (FIG. 16B), the second box indicating HVR-L2 (FIG. 16A) or HVR-H2 (FIG. 16B), and the third box indicating HVR-L3 (FIG. 16A) or HVR-H3 (FIG. 16B).

FIGS. 17A-B depict the heavy chain (FIG. 17A; SEQ ID NO. 14) and light chain (FIG. 17B; SEQ ID NO. 15) of an exemplary anti-Abeta antibody.

DETAILED DESCRIPTION OF EMBODIMENTS OF THE INVENTION

I. Definitions

Figure 1A:
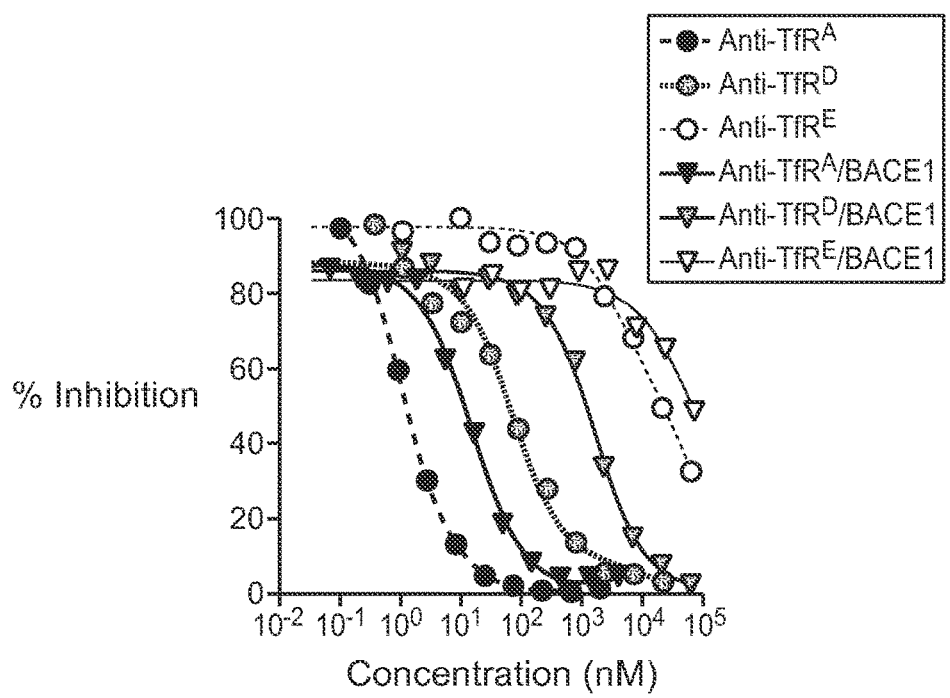
FIGS. 1A-1E depict the results of experiments assessing the affinities of anti-transferrin receptor ("TfR") and anti-TfR/beta-secretase ("BACE1") variants for TfR, as well as concentrations of the antibody and $A\beta_{1-40}$ after administration in mice, as described in Example 1. The competitive ELISA assay results in FIG. 1A show that anti-TfR/BACE1 variants and anti-TfR variants have distinct affinities for TfR.

The "blood-brain barrier" or "BBB" refers to the physiological barrier between the peripheral circulation and the brain and spinal cord (i.e., the CNS) which is formed by tight junctions within the brain capillary endothelial plasma membranes, creating a tight barrier that restricts the transport of molecules into the brain, even very small molecules such as urea (60 Daltons). The blood-brain barrier within the brain, the blood-spinal cord barrier within the spinal cord, and the blood-retinal barrier within the retina are contiguous capillary barriers within the CNS, and are herein collectively referred to a the blood-brain barrier or BBB. The BBB also encompasses the blood-CSF barrier (choroid plexus) where the barrier is comprised of ependymal cells rather than capillary endothelial cells.

The "central nervous system" or "CNS" refers to the complex of nerve tissues that control bodily function, and includes the brain and spinal cord.

A "blood-brain barrier receptor" (abbreviated "BBB-R" herein) is a transmembrane receptor protein expressed on brain endothelial cells which is capable of transporting molecules across the blood-brain barrier. Examples of BBB-R include, but are not limited to: transferrin receptor (TfR), insulin receptor, insulin-like growth factor receptor (IGF-R), low density lipoprotein receptors including without limitation low density lipoprotein receptor-related protein 1 (LRP1) and low density lipoprotein receptor-related protein 8 (LRP8), glucose transporter 1 (Glut1) and heparin-binding epidermal growth factor-like growth factor (HB-EGF). An exemplary BBB-R herein is transferrin receptor (TfR).

The "transferrin receptor" ("TfR") is a transmembrane glycoprotein (with a molecular weight of about 180,000) composed of two disulphide-bonded sub-units (each of apparent molecular weight of about 90,000) involved in iron uptake in vertebrates. In one embodiment, the TfR herein is human TfR comprising the amino acid sequence as set forth in Schneider et al. Nature 311: 675-678 (1984), for example.

A "neurological disorder" as used herein refers to a disease or disorder which affects the CNS and/or which has an etiology in the CNS. Exemplary CNS diseases or disorders include, but are not limited to, neuropathy, amyloidosis, cancer, an ocular disease or disorder, viral or microbial infection, inflammation, ischemia, neurodegenerative disease, seizure, behavioral disorders, and a lysosomal storage disease. For the purposes of this application, the CNS will be understood to include the eye, which is normally sequestered from the rest of the body by the blood-retina barrier. Specific examples of neurological disorders include, but are not limited to, neurodegenerative diseases (including, but not limited to, Lewy body disease, postpoliomyelitis syndrome, Shy-Draeger syndrome, olivopontocerebellar atrophy, Parkinson's disease, multiple system atrophy, striatonigral degeneration, tauopathies (including, but not limited to, Alzheimer disease and supranuclear palsy), prion diseases (including, but not limited to, bovine spongiform encephalopathy, scrapie, Creutzfeldt-Jakob syndrome, kuru, Gerstmann-Straussler-Scheinker disease, chronic wasting disease, and fatal familial insomnia), bulbar palsy, motor neuron disease, and nervous system heterodegenerative disorders (including, but not limited to, Canavan disease, Huntington's disease, neuronal ceroid-lipofuscinosis, Alexander's disease, Tourette's syndrome, Menkes kinky hair syndrome, Cockayne syndrome, Halervorden-Spatz syndrome, lafora disease, Rett syndrome, hepatolenticular degeneration, Lesch-Nyhan syndrome, and Unverricht-Lundborg syndrome), dementia (including, but not limited to, Pick's disease, and spinocerebellar ataxia), cancer (e.g. of the CNS, including brain metastases resulting from cancer elsewhere in the body).

A "neurological disorder drug" is a drug or therapeutic agent that treats one or more neurological disorder(s). Neurological disorder drugs of the invention include, but are not limited to, antibodies, peptides, proteins, natural ligands of one or more CNS target(s), modified versions of natural ligands of one or more CNS target(s), aptamers, inhibitory nucleic acids (i.e., small inhibitory RNAs (siRNA) and short hairpin RNAs (shRNA)), ribozymes, and small molecules, or active fragments of any of the foregoing. Exemplary neurological disorder drugs of the invention are described herein and include, but are not limited to: antibodies, aptamers, proteins, peptides, inhibitory nucleic acids and small molecules and active fragments of any of the foregoing that either are themselves or specifically recognize and/or act upon (i.e., inhibit, activate, or detect) a CNS antigen or target molecule such as, but not limited to, amyloid precursor protein or portions thereof, amyloid beta, beta-secretase, gamma-secretase, tau, alpha-synuclein, parkin, huntingtin, DR6, presenilin, ApoE, glioma or other CNS cancer markers, and neurotrophins. Non-limiting examples of neurological disorder drugs and the disorders they may be used to treat are provided in the following Table 1:

TABLE 1

Non-limiting examples of neurological disorder drugs and the corresponding disorders they may be used to treat

| Drug | Neurological disorder |
| --- | --- |
| Anti-BACE1 Antibody | Alzheimer's, acute and chronic brain injury, stroke |
| Anti-Abeta Antibody | Alzheimer's disease |
| Anti-Tau Antibody | Alzheimer's disease, tauopathies |
| Neurotrophin | Stroke, acute brain injury, spinal cord injury |
| Brain-derived neurotrophic factor (BDNF), Fibroblast growth factor 2 (FGF-2) | Chronic brain injury (Neurogenesis) |
| Anti-Epidermal Growth Factor Receptor (EGFR)-antibody | Brain cancer |
| Glial cell-line derived neural factor (GDNF) | Parkinson's disease |

TABLE 1-continued

Non-limiting examples of neurological disorder drugs and the corresponding disorders they may be used to treat

| Drug | Neurological disorder |
| --- | --- |
| Brain-derived neurotrophic factor (BDNF) | Amyotrophic lateral sclerosis, depression |
| Lysosomal enzyme | Lysosomal storage disorders of the brain |
| Ciliary neurotrophic factor (CNTF) | Amyotrophic lateral sclerosis |
| Neuregulin-1 | Schizophrenia |
| Anti-HER2 antibody (e.g. trastuzumab, pertuzumab, etc.) | Brain metastasis from HER2-positive cancer |
| Anti-VEGF antibody (e.g., bevacizumab) | Recurrent or newly diagnosed glioblastoma, recurrent malignant glioma, brain metastasis |

An "imaging agent" is a compound that has one or more properties that permit its presence and/or location to be detected directly or indirectly. Examples of such imaging agents include proteins and small molecule compounds incorporating a labeled moiety that permits detection.

A "CNS antigen" or "brain antigen" is an antigen expressed in the CNS, including the brain, which can be targeted with an antibody or small molecule. Examples of such antigens include, without limitation: beta-secretase 1 (BACE1), amyloid beta (Abeta), epidermal growth factor receptor (EGFR), human epidermal growth factor receptor 2 (HER2), tau, apolipoprotein E4 (ApoE4), alpha-synuclein, CD20, huntingtin, prion protein (PrP), leucine rich repeat kinase 2 (LRRK2), parkin, presenilin 1, presenilin 2, gamma secretase, death receptor 6 (DR6), amyloid precursor protein (APP), p75 neurotrophin receptor (p75NTR), interleukin 6 receptor (IL6R), TNF receptor 1 (TNFR1), interleukin 1 beta (IL1β), and caspase 6. In one embodiment, the antigen is BACE1.

The term "BACE1," as used herein, refers to any native beta-secretase 1 (also called β-site amyloid precursor protein cleaving enzyme 1, membrane-associated aspartic protease 2, memapsin 2, aspartyl protease 2 or Asp2) from any vertebrate source, including mammals such as primates (e.g. humans) and rodents (e.g., mice and rats), unless otherwise indicated. The term encompasses "full-length," unprocessed BACE1 as well as any form of BACE1 which results from processing in the cell. The term also encompasses naturally occurring variants of BACE1, e.g., splice variants or allelic variants. The amino acid sequence of an exemplary BACE1 polypeptide is the sequence for human BACE1, isoform A as reported in Vassar et al., *Science* 286:735-741 (1999), which is incorporated herein by reference in its entirety. Several other isoforms of human BACE1 exist including isoforms B, C and D. See UniProtKB/Swiss-Prot Entry P56817, which is incorporated herein by reference in its entirety.

The terms "anti-beta-secretase antibody", "anti-BACE1 antibody", "an antibody that binds to beta-secretase" and "an antibody that binds to BACE1" refer to an antibody that is capable of binding BACE1 with sufficient affinity such that the antibody is useful as a diagnostic and/or therapeutic agent in targeting BACE1. In one embodiment, the extent of binding of an anti-BACE1 antibody to an unrelated, non-BACE1 protein is less than about 10% of the binding of the antibody to BACE1 as measured, e.g., by a radioimmunoassay (RIA). In certain embodiments, an antibody that binds to BACE1 has a dissociation constant (Kd) of ≤1 µM, ≤100 nM, ≤10 nM, ≤1 nM, ≤0.1 nM, ≤0.01 nM, or ≤0.001 nM (e.g. $10^{-8}$M or less, e.g. from $10^{-8}$M to $10^{-13}$M, e.g., from $10^{-9}$ M to $10^{-13}$ M). In certain embodiments, an anti-BACE1 antibody binds to an epitope of BACE1 that is conserved among BACE1 from different species and isoforms. In one embodiment, an antibody is provided that binds to the epitope on BACE1 bound by anti-BACE1 antibody YW412.8.31. In other embodiments, an antibody is provided that binds to an exosite within BACE1 located in the catalytic domain of BACE1. In one embodiment an antibody is provided that competes with the peptides identified in Kornacker et al., *Biochem.* 44:11567-11573 (2005), which is incorporated herein by reference in its entirety, (i.e., Peptides 1, 2, 3, 1-11, 1-10, 1-9, 1-8, 1-7, 1-6, 2-12, 3-12, 4-12, 5-12, 6-12, 7-12, 8-12, 9-12, 10-12, 4, 5, 6, 5-10, 5-9, scrambled, YSA, P6A, Y7A, FBA, I9A, P10A and L11A) for binding to BACE1. Exemplary BACE1 antibody sequences are depicted in FIG. 15A-B and FIG. 16A-B. One exemplary antibody herein comprises the variable domains of the antibody YW412.8.31 (e.g. as in FIGS. 15A-B).

A "native sequence" protein herein refers to a protein comprising the amino acid sequence of a protein found in nature, including naturally occurring variants of the protein. The term as used herein includes the protein as isolated from a natural source thereof or as recombinantly produced.

The term "antibody" herein is used in the broadest sense and specifically covers monoclonal antibodies, polyclonal antibodies, multispecific antibodies (e.g. bispecific antibodies) formed from at least two intact antibodies, and antibody fragments so long as they exhibit the desired biological activity.

"Antibody fragments" herein comprise a portion of an intact antibody which retains the ability to bind antigen. Examples of antibody fragments are well known in the art (see, e.g., Nelson, MAbs (2010) 2(1): 77-83) and include but are not limited to Fab, Fab', F(ab')2, and Fv fragments; diabodies; linear antibodies; single-chain antibody molecules including but not limited to single-chain variable fragments (scFv), fusions of light and/or heavy-chain antigen-binding domains with or without a linker (and optionally in tandem); and monospecific or multispecific antigen-binding molecules formed from antibody fragments (including, but not limited to multispecific antibodies constructed from multiple variable domains which lack Fc regions).

The term "monoclonal antibody" as used herein refers to an antibody obtained from a population of substantially homogeneous antibodies, i.e., the individual antibodies comprising the population are identical and/or bind the same epitope, except for possible variants that may arise during production of the monoclonal antibody, such variants generally being present in minor amounts. In contrast to polyclonal antibody preparations that typically include different antibodies directed against different determinants (epitopes), each monoclonal antibody is directed against a single determinant on the antigen. In addition to their specificity, the monoclonal antibodies are advantageous in that they are uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature*, 256:495 (1975), or may be made by recombinant DNA methods (see, e.g., U.S. Pat. No. 4,816,567). The "monoclonal antibodies" may also be isolated from phage antibody libraries using the techniques described in Clackson et al., *Nature*, 352:624-628 (1991) and Marks et al., *J. Mol. Biol.*, 222:581-597 (1991), for example. Specific examples of monoclonal antibodies herein include chimeric antibodies, humanized antibodies, and human antibodies, including antigen-binding fragments thereof.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Natl. Acad. Sci. USA*, 81:6851-6855 (1984)). Chimeric antibodies of interest herein include "primatized" antibodies comprising variable domain antigen-binding sequences derived from a non-human primate (e.g. Old World Monkey, such as baboon, rhesus or cynomolgus monkey) and human constant region sequences (U.S. Pat. No. 5,693,780).

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable regions correspond to those of a non-human immunoglobulin and all or substantially all of the FRs are those of a human immunoglobulin sequence, except for FR substitution(s) as noted above. The humanized antibody optionally also will comprise at least a portion of an immunoglobulin constant region, typically that of a human immunoglobulin. For further details, see Jones et al., *Nature* 321:522-525 (1986); Riechmann et al., *Nature* 332: 323-329 (1988); and Presta, *Curr. Op. Struct. Biol.* 2:593-596 (1992).

A "human antibody" herein is one comprising an amino acid sequence structure that corresponds with the amino acid sequence structure of an antibody obtainable from a human B-cell, and includes antigen-binding fragments of human antibodies. Such antibodies can be identified or made by a variety of techniques, including, but not limited to: production by transgenic animals (e.g., mice) that are capable, upon immunization, of producing human antibodies in the absence of endogenous immunoglobulin production (see, e.g., Jakobovits et al., *Proc. Natl. Acad. Sci. USA*, 90:2551 (1993); Jakobovits et al., *Nature*, 362:255-258 (1993); Bruggermann et al., *Year in Immuno.*, 7:33 (1993); and U.S. Pat. Nos. 5,591,669, 5,589,369 and 5,545,807)); selection from phage display libraries expressing human antibodies or human antibody fragments (see, for example, McCafferty et al., *Nature* 348:552-553 (1990); Johnson et al., *Current Opinion in Structural Biology* 3:564-571 (1993); Clackson et al., *Nature*, 352:624-628 (1991); Marks et al., *J. Mol. Biol.*

222:581-597 (1991); Griffith et al., *EMBO J.* 12:725-734 (1993); U.S. Pat. Nos. 5,565,332 and 5,573,905); generation via in vitro activated B cells (see U.S. Pat. Nos. 5,567,610 and 5,229,275); and isolation from human antibody-producing hybridomas.

A "multispecific antibody" herein is an antibody having binding specificities for at least two different epitopes. Exemplary multispecific antibodies may bind both a BBB-R and a brain antigen. Multispecific antibodies can be prepared as full-length antibodies or antibody fragments (e.g. F(ab')2 bispecific antibodies). Engineered antibodies with two, three or more (e.g. four) functional antigen binding sites are also contemplated (see, e.g., US Appln No. US 2002/0004587 A1, Miller et al.). Multispecific antibodies can be prepared as full length antibodies or as antibody fragments.

Antibodies herein include "amino acid sequence variants" with altered antigen-binding or biological activity. Examples of such amino acid alterations include antibodies with enhanced affinity for antigen (e.g. "affinity matured" antibodies), and antibodies with altered Fc region, if present, e.g. with altered (increased or diminished) antibody dependent cellular cytotoxicity (ADCC) and/or complement dependent cytotoxicity (CDC) (see, for example, WO 00/42072, Presta, L. and WO 99/51642, Iduosogie et al.); and/or increased or diminished serum half-life (see, for example, WO00/42072, Presta, L.).

An "affinity modified variant" has one or more substituted hypervariable region or framework residues of a parent antibody (e.g. of a parent chimeric, humanized, or human antibody) that alter (increase or reduce) affinity. A convenient way for generating such substitutional variants uses phage display. Briefly, several hypervariable region sites (e.g. 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g. binding affinity). In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and its target. Such contact residues and neighboring residues are candidates for substitution according to the techniques elaborated herein. Once such variants are generated, the panel of variants is subjected to screening and antibodies with altered affinity may be selected for further development.

A "pH-sensitive antibody variant" is an antibody variant which has a different binding binding affinity for a target antigen at a first pH than it does for that target antigen at a different pH. As a nonlimiting example, an anti-TfR antibody of the invention may be selected for or engineered to have pH-sensitive binding to TfR such that it binds with desirably low affinity (as described herein) to cell surface TfR in the plasma at pH 7.4, but upon internalization into an endosomal compartment, rapidly dissociates from TfR at the relatively lower pH (pH 5.5-6.0); such dissociation may protect the antibody from antigen-mediated clearance, and increase the amount of antibody that is either delivered to the CNS or recycled back across the BBB—in either case, the effective concentration of the antibody is increased relative to an anti-TfR antibody that does not comprise such pH sensitivity (see, e.g., Chaparro-Riggers et al. J. Biol. Chem. 287(14): 11090-11097; Igawa et al., Nature Biotechnol. 28(11): 1203-1208). The desired combination of affinities at the serum pH and the endosomal compartment pH can be readily determined for a particular BBB-R and conjugated compound by one of ordinary skill in the art.

The antibody herein may be conjugated with a "heterologous molecule" for example to increase half-life or stability or otherwise improve the antibody. For example, the antibody may be linked to one of a variety of non-proteinaceous polymers, e.g., polyethylene glycol (PEG), polypropylene glycol, polyoxyalkylenes, or copolymers of polyethylene glycol and polypropylene glycol. Antibody fragments, such as Fab', linked to one or more PEG molecules are an exemplary embodiment of the invention. In another example, the heterologous molecule is a therapeutic compound or a visualization agent (ie., a detectable label), and the antibody is being used to transport such heterologous molecule across the BBB. Examples of heterologous molecules include, but are not limited to, a chemical compound, a peptide, a polymer, a lipid, a nucleic acid, and a protein.

The antibody herein may be a "glycosylation variant" such that any carbohydrate attached to the Fc region, if present, is altered, either modified in presence/absence, or modified in type. For example, antibodies with a mature carbohydrate structure that lacks fucose attached to an Fc region of the antibody are described in US Pat Appl No US 2003/0157108 (Presta, L.). See also US 2004/0093621 (Kyowa Hakko Kogyo Co., Ltd). Antibodies with a bisecting N-acetylglucosamine (GlcNAc) in the carbohydrate attached to an Fc region of the antibody are referenced in WO 2003/011878, Jean-Mairet et al. and U.S. Pat. No. 6,602,684, Umana et al. Antibodies with at least one galactose residue in the oligosaccharide attached to an Fc region of the antibody are reported in WO 1997/30087, Patel et al. See, also, WO 1998/58964 (Raju, S.) and WO 1999/22764 (Raju, S.) concerning antibodies with altered carbohydrate attached to the Fc region thereof. See also US 2005/0123546 (Umana et al.) describing antibodies with modified glycosylation. Mutation of the consensus glycosylation sequence in the Fc region (Asn-X-Ser/Thr at positions 297-299, where X cannot be proline), for example by mutating the Asn of this sequence to any other amino acid, by placing a Pro at position 298, or by modifying position 299 to any amino acid other than Ser or Thr should abrogate glycosylation at that position (see, e.g., Fares Al-Ejeh et al., Clin. Cancer Res. (2007) 13:5519s-5527s; Imperiali and Shannon, Biochemistry (1991) 30(18): 4374-4380; Katsuri, Biochem J. (1997) 323(Pt 2): 415-419; Shakin-Eshleman et al., J. Biol. Chem. (1996) 271: 6363-6366).

The term "hypervariable region" when used herein refers to the amino acid residues of an antibody that are responsible for antigen binding. The hypervariable region comprises amino acid residues from a "complementarity determining region" or "CDR" (e.g. residues 24-34 (L1), 50-56 (L2) and 89-97 (L3) in the light chain variable domain and 31-35 (H1), 50-65 (H2) and 95-102 (H3) in the heavy chain variable domain; Kabat et al., *Sequences of Proteins of Immunological Interest*, 5th Ed. Public Health Service, National Institutes of Health, Bethesda, Md. (1991)) and/or those residues from a "hypervariable loop" (e.g. residues 26-32 (L1), 50-52 (L2) and 91-96 (L3) in the light chain variable domain and 26-32 (H1), 53-55 (H2) and 96-101 (H3) in the heavy chain variable domain; Chothia and Lesk *J. Mol. Biol.* 196:901-917 (1987)). "Framework" or "FR" residues are those variable domain residues other than the hypervariable region residues as herein defined.

A "full length antibody" is one which comprises an antigen-binding variable region as well as a light chain constant domain (CL) and heavy chain constant domains, CH1, CH2 and CH3. The constant domains may be native sequence constant domains (e.g. human native sequence constant domains) or amino acid sequence variants thereof.

A "naked antibody" is an antibody (as herein defined) that is not conjugated to a heterologous molecule, such as a cytotoxic moiety, polymer, or radiolabel.

Antibody "effector functions" refer to those biological activities of an antibody that result in activation of the immune system other than activation of the complement pathway. Such activities are largely found in the Fc region (a native sequence Fc region or amino acid sequence variant Fc region) of an antibody. Examples of antibody effector functions include, for example, Fc receptor binding and antibody-dependent cell-mediated cytotoxicity (ADCC). In one embodiment, the antibody herein essentially lacks effector function. In another embodiment, the antibody herein retains minimal effector function. Methods of modifying or eliminating effector function are well-known in the art and include, but are not limited to, eliminating all or a portion of the Fc region responsible for the effector function (ie, using an antibody or antibody fragment in a format lacking all or a portion of the Fc region such as, but not limited to, a Fab fragment, a single-chain antibody, and the like as described herein and as known in the art; modifying the Fc region at one or more amino acid positions to eliminate effector function (Fc binding-impacting: positions 238, 239, 248, 249, 252, 254, 265, 268, 269, 270, 272, 278, 289, 292, 293, 294, 295, 296, 297, 298, 301, 303, 322, 324, 327, 329, 333, 335, 338, 340, 373, 376, 382, 388, 389, 414, 416, 419, 434, 435, 437, 438, and 439; and modifying the glycosylation of the antibody (including, but not limited to, producing the antibody in an environment that does not permit wild-type mammalian glycosylation, removing one or more carbohydrate groups from an already-glycosylated antibody, and modifying the antibody at one or more amino acid positions to eliminate the ability of the antibody to be glycosylated at those positions (including, but not limited to N297G and N297A).

Antibody "complement activation" functions, or properties of an antibody that enable or trigger "activation of the complement pathway" are used interchangeably, and refer to those biological activities of an antibody that engage or stimulate the complement pathway of the immune system in a subject. Such activities include, e.g., C1q binding and complement dependent cytotoxicity (CDC), and may be mediated by both the Fc portion and the non-Fc portion of the antibody. Methods of modifying or eliminating complement activation function are well-known in the art and include, but are not limited to, eliminating all or a portion of the Fc region responsible for complement activation (ie., using an antibody or antibody fragment in a format lacking all or a portion of the Fc region such as, but not limited to, a Fab fragment, a single-chain antibody, and the like as described herein and as known in the art, or modifying the Fc region at one or more amino acid positions to eliminate or lessen interactions with complement components or the ability to activate complement components, such as positions 270, 322, 329 and 321, known to be involved in C1q binding), and modifying or eliminating a portion of the non-Fc region responsible for complement activation (ie, modifying the CH1 region at position 132 (see, e.g., Vidarte et al., (2001) J. Biol. Chem. 276(41): 38217-38223)).

Depending on the amino acid sequence of the constant domain of their heavy chains, full length antibodies can be assigned to different "classes". There are five major classes of full length antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called alpha, delta, epsilon, gamma, and mu, respectively. The subunit structures and three-dimensional configurations of different classes of immunoglobulins are well known.

The term "recombinant antibody", as used herein, refers to an antibody (e.g. a chimeric, humanized, or human antibody or antigen-binding fragment thereof) that is expressed by a recombinant host cell comprising nucleic acid encoding the antibody. Examples of "host cells" for producing recombinant antibodies include: (1) mammalian cells, for example, Chinese Hamster Ovary (CHO), COS, myeloma cells (including Y0 and NS0 cells), baby hamster kidney (BHK), Hela and Vero cells; (2) insect cells, for example, sf9, sf21 and Tn5; (3) plant cells, for example plants belonging to the genus *Nicotiana* (e.g. *Nicotiana tabacum*); (4) yeast cells, for example, those belonging to the genus *Saccharomyces* (e.g. *Saccharomyces cerevisiae*) or the genus *Aspergillus* (e.g. *Aspergillus niger*); (5) bacterial cells, for example *Escherichia coli* cells or *Bacillus subtilis* cells, etc.

As used herein, "specifically binding" or "binds specifically to" refers to an antibody selectively or preferentially binding to an antigen. The binding affinity is generally determined using a standard assay, such as Scatchard analysis, or surface plasmon resonance technique (e.g. using BIACORE®).

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. In one embodiment, an anti-BACE1 antibody binds to the BACE1 epitope bound by YW412.8.31.

The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof.

An "effective amount" of an agent, e.g., a pharmaceutical formulation, refers to an amount effective, at dosages and for periods of time necessary, to achieve the desired therapeutic or prophylactic result.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest,* 5th Ed. Public Health Service, National Institutes of Health, Bethesda, Md., 1991.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

An "immunoconjugate" is an antibody conjugated to one or more heterologous molecule(s), including but not limited to a label or cytotoxic agent. Optionally such conjugation is via a linker.

A "linker" as used herein is a structure that covalently or non-covalently connects the anti-BBB-R antibody to heterologous molecule. In certain embodiments, a linker is a peptide. In other embodiments, a linker is a chemical linker.

A "label" is a marker coupled with the antibody herein and used for detection or imaging. Examples of such labels include: radiolabel, a fluorophore, a chromophore, or an affinity tag. In one embodiment, the label is a radiolabel used for medical imaging, for example tc99m or I123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese, iron, etc.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC) methods. For review of methods for assessment of antibody purity, see, e.g., Flatman et al., *J. Chromatogr. B* 848:79-87 (2007).

The term "package insert" is used to refer to instructions customarily included in commercial packages of therapeutic products, that contain information about the indications, usage, dosage, administration, combination therapy, contraindications and/or warnings concerning the use of such therapeutic products.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

II. Compositions and Methods

A. Production of Anti-BBB-R Antibodies and Conjugates Thereof

The methods and articles of manufacture of the present invention use, or incorporate, an antibody that binds to a BBB-R. The BBB-R antigen to be used for production of, or screening for, antibodies may be, e.g., a soluble form of or a portion thereof (e.g. the extracellular domain) of the BBB-R containing the desired epitope. Alternatively, or additionally, cells expressing BBB-R at their cell surface can be used to generate, or screen for, antibodies. Other forms and presentations of BBB-R useful for generating antibodies will be apparent to those skilled in the art. Examples of BBB-Rs herein include transferrin receptor (TfR), insulin receptor, insulin-like growth factor receptor (IGF-R), low density lipoprotein receptor-related protein 1 (LRP1) and LRP8 etc, glucose transporter 1 (Glut1) and heparin-binding epidermal growth factor-like growth factor (HB-EGF).

According to the present invention, a "low affinity" anti-BBB-R (e.g. anti-TfR) antibody is selected based on the data herein demonstrating that such antibodies display improved CNS (for example, brain) uptake. In order to identify such low affinity antibodies, various assays for measuring antibody affinity are available including, without limitation: Scatchard assay and surface plasmon resonance technique (e.g. using BIACORE®). According to one embodiment of the invention, the antibody has an affinity for the BBB-R antigen (e.g. for TfR) from about 5 nM, or from about 20 nM, or from about 100 nM, to about 50 μM, or to about 30 μM, or to about 10 μM, or to about 1 μM, or to about 500 nM. Thus, the affinity may be in the range from about 5 nM to about 50 μM, or in the range from about 20 nM to about 30 μM, or in the range from about 30 nM to about 30 μM, or in the range from about 50 nM to about 1 μM, or in the range from about 100 nM to about 500 nM, e.g. as measured by Scatchard analysis or BIACORE®. In another embodiment of the invention, the antibody has a dissociation half-life from the BBB-R antigen (e.g. for TfR) of less than 1 minute, less than 2 minutes, less than 3 minutes, less than four minutes, less than 5 minutes, or less than 10 minutes to about 20 minutes, or to about 30 minutes, as measured by competition binding analysis or BIACORE®.

Thus, the invention provides a method of making an antibody useful for transporting a neurological disorder drug across the blood-brain barrier comprising selecting an antibody from a panel of antibodies against a blood-brain barrier receptor (BBB-R) because it has an affinity for the BBB-R which is in the range from about 5 nM, or from about 20 nM, or from about 100 nM, to about 50 μM, or to about 30 μM, or to about 10 μM, or to about 1 μM, or to about 500 mM. Thus, the affinity may be in the range from about 5 nM to about 50 μM, or in the range from about 20 nM to about 30 μM, or in the range from about 30 nM to about 30 μM, or in the range from about 50 nM to about 1 μM, or in the range from about 100 nM to about 500 nM, e.g. as measured by Scatchard analysis or BIACORE®. As will be understood by one of ordinary skill in the art, conjugating a heterologous molecule/compound to an antibody will often decrease the affinity of the antibody for its target due, e.g., to steric hindrance or even to elimination of one binding arm if the antibody is made multispecific with one or more arms binding to a different antigen than the antibody's original target. In one embodiment, a low affinity antibody of the invention specific for TfR conjugated to BACE1 had a Kd for TfR as measured by BIACORE of about 30 nM. In another embodiment, a low affinity antibody of the invention specific for TfR conjugated to BACE1 had a Kd for TfR as measured by BIACORE of about 600 nM. In another embodiment, a low affinity antibody of the invention specific for TfR conjugated to BACE1 had a Kd for TfR as measured by BIACORE of about 20 µM. In another embodiment, a low affinity antibody of the invention specific for TfR conjugated to BACE1 had a Kd for TfR as measured by BIACORE of about 30 µM.

One exemplary assay for evaluating antibody affinity is by Scatchard analysis. For example, the anti-BBB-R antibody of interest can be iodinated using the lactoperoxidase method (Bennett and Horuk, *Methods in Enzymology* 288 pg. 134-148 (1997)). A radiolabeled anti-BBB-R antibody is purified from free $^{125}$I-Na by gel filtration using a NAP-5 column and its specific activity measured. Competition reaction mixtures of 50 µL containing a fixed concentration of iodinated antibody and decreasing concentrations of serially diluted unlabeled antibody are placed into 96-well plates. Cells transiently expressing BBB-R are cultured in growth media, consisting of Dulbecco's modified eagle's medium (DMEM) (Genentech) supplemented with 10% FBS, 2 mM L-glutamine and 1×penicillin-streptomycin at 37° C. in 5% $CO_2$. Cells are detached from the dishes using Sigma Cell Dissociation Solution and washed with binding buffer (DMEM with 1% bovine serum albumin, 50 mM HEPES, pH 7.2, and 0.2% sodium azide). The washed cells are added at an approximate density of 200,000 cells in 0.2 mL of binding buffer to the 96-well plates containing the 50-µL competition reaction mixtures. The final concentration of the unlabeled antibody in the competition reaction with cells is varied, starting at 1000 nM and then decreasing by 1:2 fold dilution for 10 concentrations and including a zero-added, buffer-only sample. Competition reactions with cells for each concentration of unlabeled antibody are assayed in triplicate. Competition reactions with cells are incubated for 2 hours at room temperature. After the 2-hour incubation, the competition reactions are transferred to a filter plate and washed four times with binding buffer to separate free from bound iodinated antibody. The filters are counted by gamma counter and the binding data are evaluated using the fitting algorithm of Munson and Rodbard (1980) to determine the binding affinity of the antibody.

An exemplary scatchard analysis using the compositions of the invention may be performed as follows. Anti-TFR$^A$ was iodinated using the lactoperoxidase method (Bennett and Horuk, *Methods in Enzymology* 288 pg. 134-148 (1997)). Radiolabeled anti-TFR$^A$ was purified from free $^{125}$I-Na by gel filtration using a NAP-5 column; purified anti-TFR$^A$ had a specific activity of 19.82 µCi/µg. Competition reaction mixtures of 50 µL containing a fixed concentration of iodinated antibody and decreasing concentrations of serially diluted unlabeled antibody were placed into 96-well plates. The 293 cells transiently expressing murine TfR were cultured in growth media, consisting of Dulbecco's modified eagle's medium (DMEM) (Genentech) supplemented with 10% FBS, 2 mM L-glutamine and 1×penicillin-streptomycin at 37° C. in 5% $CO_2$. Cells were detached from the dishes using Sigma Cell Dissociation Solution and washed with binding buffer (DMEM with 1% bovine serum albumin, 50 mM HEPES, pH 7.2, and 0.2% sodium azide). The washed cells were added at an approximate density of 200,000 cells in 0.2 mL of binding buffer to the 96-well plates containing the 50-µL competition reaction mixtures. The final concentration of the iodinated antibody in each competition reaction with cells was 100 pM (134,000 cpm per 0.25 mL). The final concentration of the unlabeled antibody in the competition reaction with cells varied, starting at 1000 nM and then decreasing by 1:2 fold dilution for 10 concentrations and including a zero-added, buffer-only sample. Competition reactions with cells for each concentration of unlabeled antibody were assayed in triplicate. Competition reactions with cells were incubated for 2 hours at room temperature. After the 2-hour incubation, the competition reactions were transferred to a Millipore Multiscreen filter plate and washed four times with binding buffer to separate free from bound iodinated antibody. The filters were counted on a Wallac Wizard 1470 gamma counter (PerkinElmer Life and Analytical Sciences; Waltham, Mass.). The binding data were evaluated using New Ligand software (Genentech), which uses the fitting algorithm of Munson and Rodbard (1980) to determine the binding affinity of the antibody.

An exemplary BIACORE® analysis using the compositions of the invention may be performed as follows. Kd was measured using surface plasmon resonance assays using a BIACORE®-2000 (BIAcore, Inc., Piscataway, N.J.) at 25° C. using anti-human Fc kit (BiAcore Inc., Piscataway, N.J.). Briefly, carboxymethylated dextran biosensor chips (CM5, BIACORE, Inc.) were activated with N-ethyl-N'-(3-dimethylaminopropyl)-carbodiimide hydrochloride (EDC) and N-hydroxysuccinimide (NHS) according to the supplier's instructions. Anti-human Fc antibody was diluted with 10 mM sodium acetate, pH 4.0, to 50 µg/ml before injection at a flow rate of 5 µl/minute to achieve approximately 10000 response units (RU) of coupled protein. Following the injection of antibody, 1 M ethanolamine was injected to block unreacted groups. For kinetics measurements, monospecific or multispecific anti-TfR antibody variants were injected in HBS-P to reach about 220 RU, then two-fold serial dilutions of MuTfR-His (0.61 nM to 157 nM) were injected in HBS-P at 25° C. at a flow rate of approximately 30 μl/min. Association rates (kon) and dissociation rates (koff) were calculated using a simple one-to-one Langmuir binding model (BIACORE® Evaluation Software version 3.2) by simultaneously fitting the association and dissociation sensorgrams. The equilibrium dissociation constant (Kd) was calculated as the ratio koff/kon. See, e.g., Chen et al., *J. Mol. Biol.* 293:865-881 (1999)

According to another embodiment, Kd is measured using surface plasmon resonance assays with a BIACORE®-2000 device (BIAcore, Inc., Piscataway, N.J.) at 25° C. using anti-human Fc kit (BiAcore Inc., Piscataway, N.J.). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Anti-human Fc antibody is diluted with 10 mM sodium acetate, pH 4.0, to 50 μg/ml before injection at a flow rate of 5 μl/minute to achieve approximately 10000 response units (RU) of coupled protein. Following the injection of antibody, 1 M ethanolamine is injected to block unreacted groups. For kinetics measurements, anti-BBB-R antibody variants are injected in HBS-P to reach about 220 RU, then two-fold serial dilutions of BBB-R-His (0.61 nM to 157 nM) are injected in HBS-P at 25° C. at a flow rate of approximately 30 μl/min. Association rates (kon) and dissociation rates (koff) are calculated using a simple one-to-one *Langmuir* binding model (BIACORE® Evaluation Software version 3.2) by simultaneously fitting the association and dissociation sensorgrams. The equilibrium dissociation constant (Kd) is calculated as the ratio koff/kon. See, e.g., Chen et al., *J. Mol. Biol.* 293:865-881 (1999).

A surrogate measurement for the affinity of one or more antibodies for the BBB-R is its half maximal inhibitory concentration (IC50), a measure of how much of the antibody is needed to inhibit the binding of a known BBB-R ligand to the BBB-R by 50%. Several methods of determining the IC50 for a given compound are art-known; a common approach is to perform a competition binding assay, such as that described herein in the examples, i.e. with regard to FIG. 1A. In general, a high IC50 indicates that more of the antibody is required to inhibit binding of the known ligand, and thus that the antibody's affinity for that ligand is relatively low. Conversely, a low IC50 indicates that less of the antibody is required to inhibit binding of the known ligand, and thus that the antibody's affinity for that ligand is relatively high.

An exemplary competitive ELISA assay to measure IC50 is one in which increasing concentrations of anti-TfR or anti-TfR/brain antigen (i.e., anti-TfR/BACE1, anti-TfR/Abeta and the like) variant antibodies are used to compete against biotinylated $TfR^A$ for binding to TfR. The anti-TfR competition ELISA was performed in Maxisorp plates (Neptune, N.J.) coated with 2.5 μg/ml of purified murine TfR extracellular domain in PBS at 4° C. overnight. Plates were washed with PBS/0.05% Tween 20 and blocked using Superblock blocking buffer in PBS (Thermo Scientific, Hudson, N.H.). A titration of each individual anti-TfR or anti-TfR/brain antigen (i.e., anti-TfR/BACE1 or anti-TfR/Abeta) (1:3 serial dilution) was combined with biotinylated anti-$TfR^A$ (0.5 nM final concentration) and added to the plate for 1 hour at room temperature. Plates were washed with PBS/0.05% Tween 20, and HRP-streptavidin (Southern Biotech, Birmingham) was added to the plate and incubated for 1 hour at room temperature. Plates were washed with PBS/0.05% Tween 20, and biotinylated anti-$TfR^A$ bound to the plate was detected using TMB substrate (BioFX Laboratories, Owings Mills).

In one embodiment, the low affinity anti-BBB-R antibody herein is coupled with a label and/or neurological disorder drug or imaging agent in order to more efficiently transport the label and/or drug or imaging agent across the BBB. Such coupling can be achieved by chemical cross-linkers or by generating fusion proteins, etc.

Covalent conjugation can either be direct or via a linker. In certain embodiments, direct conjugation is by construction of a protein fusion (i.e., by genetic fusion of the two genes encoding the BBB-R antibody and the neurological disorder drug and expression as a single protein). In certain embodiments, direct conjugation is by formation of a covalent bond between a reactive group on one of the two portions of the anti-BBB-R antibody and a corresponding group or acceptor on the neurological drug. In certain embodiments, direct conjugation is by modification (i.e., genetic modification) of one of the two molecules to be conjugated to include a reactive group (as nonlimiting examples, a sulfhydryl group or a carboxyl group) that forms a covalent attachment to the other molecule to be conjugated under appropriate conditions. As one nonlimiting example, a molecule (i.e., an amino acid) with a desired reactive group (i.e., a cysteine residue) may be introduced into, e.g., the anti-BBB-R antibody and a disulfide bond formed with the neurological drug. Methods for covalent conjugation of nucleic acids to proteins are also known in the art (i.e., photocrosslinking, see, e.g., Zatsepin et al. *Russ. Chem. Rev.* 74: 77-95 (2005)) Non-covalent conjugation can be by any nonconvalent attachment means, including hydrophobic bonds, ionic bonds, electrostatic interactions, and the like, as will be readily understood by one of ordinary skill in the art. Conjugation may also be performed using a variety of linkers. For example, an anti-BBB-R antibody and a neurological drug may be conjugated using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Peptide linkers, comprised of from one to twenty amino acids joined by peptide bonds, may also be used. In certain such embodiments, the amino acids are selected from the twenty naturally-occurring amino acids. In certain other such embodiments, one or more of the amino acids are selected from glycine, alanine, proline, asparagine, glutamine and lysine. The linker may be a "cleavable linker" facilitating release of the neurological drug upon delivery to the brain. For example, an acid-labile linker, peptidase-sensitive linker, photolabile linker, dimethyl linker or disulfide-containing linker (Chari et al., *Cancer Res.* 52:127-131 (1992); U.S. Pat. No. 5,208,020) may be used.

The invention herein expressly contemplates, but is not limited to, conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

For a neuropathy disorder, a neurological drug may be selected that is an analgesic including, but not limited to, a narcotic/opioid analgesic (i.e., morphine, fentanyl, hydrocodone, meperidine, methadone, oxymorphone, pentazocine, propoxyphene, tramadol, codeine and oxycodone), a nonsteroidal anti-inflammatory drug (NSAID) (i.e., ibuprofen, naproxen, diclofenac, diflunisal, etodolac, fenoprofen, flurbiprofen, indomethacin, ketorolac, mefenamic acid, meloxicam, nabumetone, oxaprozin, piroxicam, sulindac, and tolmetin), a corticosteroid (i.e., cortisone, prednisone, prednisolone, dexamethasone, methylprednisolone and triamcinolone), an anti-migraine agent (i.e., sumatriptin, almotriptan, frovatriptan, sumatriptan, rizatriptan, eletriptan, zolmitriptan, dihydroergotamine, eletriptan and ergotamine), acetaminophen, a salicylate (i.e., aspirin, choline salicylate, magnesium salicylate, diflunisal, and salsalate), a anti-convulsant (i.e., carbamazepine, clonazepam, gabapentin, lamotrigine, pregabalin, tiagabine, and topiramate), an anaesthetic (i.e., isoflurane, trichloroethylene, halothane, sevoflurane, benzocaine, chloroprocaine, cocaine, cyclomethycaine, dimethocaine, propoxycaine, procaine, novocaine, proparacaine, tetracaine, articaine, bupivacaine, carticaine, cinchocaine, etidocaine, levobupivacaine, lidocaine, mepivacaine, piperocaine, prilocaine, ropivacaine, trimecaine, saxitoxin and tetrodotoxin), and a cox-2-inhibitor (i.e., celecoxib, rofecoxib, and valdecoxib). For a neuropathy disorder with vertigo involvement, a neurological drug may be selected that is an anti-vertigo agent including, but not limited to, meclizine, diphenhydramine, promethazine and diazepam. For a neuropathy disorder with nausea involvement, a neurological drug may be selected that is an anti-nausea agent including, but not limited to, promethazine, chlorpromazine, prochlorperazine, trimethobenzamide, and metoclopramide. For a neurodegenerative disease, a neurological drug may be selected that is a growth hormone or neurotrophic factor; examples include but are not limited to brain-derived neurotrophic factor (BDNF), nerve growth factor (NGF), neurotrophin-4/5, fibroblast growth factor (FGF)-2 and other FGFs, neurotrophin (NT)-3, erythropoietin (EPO), hepatocyte growth factor (HGF), epidermal growth factor (EGF), transforming growth factor (TGF)-alpha, TGF-beta, vascular endothelial growth factor (VEGF), interleukin-1 receptor antagonist (IL-1ra), ciliary neurotrophic factor (CNTF), glial-derived neurotrophic factor (GDNF), neurturin, platelet-derived growth factor (PDGF), heregulin, neuregulin, artemin, persephin, interleukins, glial cell line derived neurotrophic factor (GFR), granulocyte-colony stimulating factor (CSF), granulocyte-macrophage-CSF, netrins, cardiotrophin-1, hedgehogs, leukemia inhibitory factor (LIF), midkine, pleiotrophin, bone morphogenetic proteins (BMPs), netrins, saposins, semaphorins, and stem cell factor (SCF).

For cancer, a neurological drug may be selected that is a chemotherapeutic agent. Examples of chemotherapeutic agents include alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphor-amide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e. g., calicheamicin, especially calicheamicin gamma1I and calicheamicin omega1I (see, e.g., Agnew, Chem Intl. Ed. Engl., 33: 183-186 (1994)); dynemicin, including dynemicin A; an esperamicin; as well as neocarzinostatin chromophore and related chromoprotein enediyne antiobiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; gemcitabine (GEMZAR®); 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovorin; vinorelbine (NAVELBINE®); novantrone; edatrexate; daunomycin; aminopterin; ibandronate; topoisomerase inhibitor RFS 2000; difluorometlhylornithine (DMFO); retinoids such as retinoic acid; capecitabine (XELODA®); pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

Also included in this definition of chemotherapeutic agents are anti-hormonal agents that act to regulate, reduce, block, or inhibit the effects of hormones that can promote the growth of cancer, and are often in the form of systemic, or whole-body treatment. They may be hormones themselves. Examples include anti-estrogens and selective estrogen receptor modulators (SERMs), including, for example, tamoxifen (including NOLVADEX® tamoxifen), EVISTA® raloxifene, droloxifene, 4-hydroxytamoxifen, trioxifene, keoxifene, LY117018, onapristone, and FARESTON® toremifene; anti-progesterones; estrogen receptor down-regulators (ERDs); agents that function to suppress or shut down the ovaries, for example, leutinizing hormone-releasing hormone (LHRH) agonists such as LUPRON® and ELIGARD® leuprolide acetate, goserelin acetate, buserelin acetate and tripterelin; other anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole. In addition, such definition of chemotherapeutic agents includes bisphosphonates such as clodronate (for example, BONEFOS® or OSTAC®), DIDROCAL® etidronate, NE-58095, ZOMETA® zoledronic acid/zoledronate, FOSAMAX® alendronate, AREDIA® pamidronate, SKELID® tiludronate, or ACTONEL® risedronate; as well as troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; LURTOTECAN® topoisomerase 1 inhibitor; ABARELIX® rmRH; lapatinib ditosylate (an ErbB-2 and EGFR dual tyrosine kinase small-molecule inhibitor also known as GW572016); and pharmaceutically acceptable salts, acids or derivatives of any of the above.

Another group of compounds that may be selected as neurological drugs for cancer treatment or prevention are anti-cancer immunoglobulins (including, but not limited to, trastuzumab, pertuzumab, bevacizumab, alemtuxumab, cetuximab, gemtuzumab ozogamicin, ibritumomab tiuxetan, panitumumab and rituximab). In some instances, antibodies in conjunction with a toxic label or conjugate may be used to target and kill desired cells (i.e., cancer cells), including, but not limited to, tositumomab with a $^{131}$I radiolabel, or trastuzumab emtansine.

For an ocular disease or disorder, a neurological drug may be selected that is an anti-angiogenic ophthalmic agent (i.e., bevacizumab, ranibizumab and pegaptanib), an ophthalmic glaucoma agent (i.e., carbachol, epinephrine, demecarium bromide, apraclonidine, brimonidine, brinzolamide, levobunolol, timolol, betaxolol, dorzolamide, bimatoprost, carteolol, metipranolol, dipivefrin, travoprost and latanoprost), a carbonic anhydrase inhibitor (i.e., methazolamide and acetazolamide), an ophthalmic antihistamine (i.e., naphazoline, phenylephrine and tetrahydrozoline), an ocular lubricant, an ophthalmic steroid (i.e., fluorometholone, prednisolone, loteprednol, dexamethasone, difluprednate, rimexolone, fluocinolone, medrysone and triamcinolone), an ophthalmic anesthetic (i.e., lidocaine, proparacaine and tetracaine), an ophthalmic anti-infective (i.e., levofloxacin, gatifloxacin, ciprofloxacin, moxifloxacin, chloramphenicol, bacitracin/polymyxin b, sulfacetamide, tobramycin, azithromycin, besifloxacin, norfloxacin, sulfisoxazole, gentamicin, idoxuridine, erythromycin, natamycin, gramicidin, neomycin, ofloxacin, trifluridine, ganciclovir, vidarabine), an ophthalmic anti-inflammatory agent (i.e., nepafenac, ketorolac, flurbiprofen, suprofen, cyclosporine, triamcinolone, diclofenac and bromfenac), and an ophthalmic antihistamine or decongestant (i.e., ketotifen, olopatadine, epinastine, naphazoline, cromolyn, tetrahydrozoline, pemirolast, bepotastine, naphazoline, phenylephrine, nedocromil, lodoxamide, phenylephrine, emedastine and azelastine).

For a seizure disorder, a neurological drug may be selected that is an anticonvulsant or antiepileptic including, but not limited to, barbiturate anticonvulsants (i.e., primidone, metharbital, mephobarbital, allobarbital, amobarbital, aprobarbital, alphenal, barbital, brallobarbital and phenobarbital), benzodiazepine anticonvulsants (i.e., diazepam, clonazepam, and lorazepam), carbamate anticonvulsants (i.e. felbamate), carbonic anhydrase inhibitor anticonvulsants (i.e., acetazolamide, topiramate and zonisamide), dibenzazepine anticonvulsants (i.e., rufinamide, carbamazepine, and oxcarbazepine), fatty acid derivative anticonvulsants (i.e., divalproex and valproic acid), gamma-aminobutyric acid analogs (i.e., pregabalin, gabapentin and vigabatrin), gamma-aminobutyric acid reuptake inhibitors (i.e., tiagabine), gamma-aminobutyric acid transaminase inhibitors (i.e., vigabatrin), hydantoin anticonvulsants (i.e. phenytoin, ethotoin, fosphenytoin and mephenytoin), miscellaneous anticonvulsants (i.e., lacosamide and magnesium sulfate), progestins (i.e., progesterone), oxazolidinedione anticonvulsants (i.e., paramethadione and trimethadione), pyrrolidine anticonvulsants (i.e., levetiracetam), succinimide anticonvulsants (i.e., ethosuximide and methsuximide), triazine anticonvulsants (i.e., lamotrigine), and urea anticonvulsants (i.e., phenacemide and pheneturide).

For a lysosomal storage disease, a neurological drug may be selected that is itself or otherwise mimics the activity of the enzyme that is impaired in the disease. Exemplary recombinant enzymes for the treatment of lysosomal storage disorders include, but are not limited to those set forth in e.g., U.S. Patent Application publication no. 2005/0142141 (i.e., alpha-L-iduronidase, iduronate-2-sulphatase, N-sulfatase, alpha-N-acetylglucosaminidase, N-acetyl-galactosamine-6-sulfatase, beta-galactosidase, arylsulphatase B, beta-glucuronidase, acid alpha-glucosidase, glucocerebrosidase, alpha-galactosidase A, hexosaminidase A, acid sphingomyelinase, beta-galactocerebrosidase, beta-galactosidase, arylsulfatase A, acid ceramidase, aspartoacylase, palmitoyl-protein thioesterase 1 and tripeptidyl amino peptidase 1).

For amyloidosis, a neurological drug may be selected that includes, but is not limited to, an antibody or other binding molecule (including, but not limited to a small molecule, a peptide, an aptamer, or other protein binder) that specifically binds to a target selected from: beta secretase, tau, presenilin, amyloid precursor protein or portions thereof, amyloid beta peptide or oligomers or fibrils thereof, death receptor 6 (DR6), receptor for advanced glycation endproducts (RAGE), parkin, and huntingtin; a cholinesterase inhibitor (i.e., galantamine, donepezil, rivastigmine and tacrine); an NMDA receptor antagonist (i.e., memantine), a monoamine depletor (i.e., tetrabenazine); an ergoloid mesylate; an anticholinergic antiparkinsonism agent (i.e., procyclidine, diphenhydramine, trihexylphenidyl, benztropine, biperiden and trihexyphenidyl); a dopaminergic antiparkinsonism agent (i.e., entacapone, selegiline, pramipexole, bromocriptine, rotigotine, selegiline, ropinirole, rasagiline, apomorphine, carbidopa, levodopa, pergolide, tolcapone and amantadine); a tetrabenazine; an anti-inflammatory (including, but not limited to, a nonsteroidal anti-inflammatory drug (i.e., indomethicin and other compounds listed above); a hormone (i.e., estrogen, progesterone and leuprolide); a vitamin (i.e., folate and nicotinamide); a dimebolin; a homotaurine (i.e., 3-aminopropanesulfonic acid; 3APS); a serotonin receptor activity modulator (i.e., xaliproden); an, an interferon, and a glucocorticoid.

For a viral or microbial disease, a neurological drug may be selected that includes, but is not limited to, an antiviral compound (including, but not limited to, an adamantane antiviral (i.e., rimantadine and amantadine), an antiviral interferon (i.e., peginterferon alfa-2b), a chemokine receptor antagonist (i.e., maraviroc), an integrase strand transfer inhibitor (i.e., raltegravir), a neuraminidase inhibitor (i.e., oseltamivir and zanamivir), a non-nucleoside reverse transcriptase inhibitor (i.e., efavirenz, etravirine, delavirdine and nevirapine), a nucleoside reverse transcriptase inhibitors (tenofovir, abacavir, lamivudine, zidovudine, stavudine, entecavir, emtricitabine, adefovir, zalcitabine, telbivudine and didanosine), a protease inhibitor (i.e., darunavir, atazanavir, fosamprenavir, tipranavir, ritonavir, nelfinavir, amprenavir, indinavir and saquinavir), a purine nucleoside (i.e., valacyclovir, famciclovir, acyclovir, ribavirin, ganciclovir, valganciclovir and cidofovir), and a miscellaneous antiviral (i.e., enfuvirtide, foscarnet, palivizumab and fomivirsen)), an antibiotic (including, but not limited to, an aminopenicillin (i.e., amoxicillin, ampicillin, oxacillin, nafcillin, cloxacillin, dicloxacillin, flucoxacillin, temocillin, azlocillin, carbenicillin, ticarcillin, mezlocillin, piperacillin and bacampicillin), a cephalosporin (i.e., cefazolin, cephalexin, cephalothin, cefamandole, ceftriaxone, cefotaxime, cefpodoxime, ceftazidime, cefadroxil, cephradine, loracarbef, cefotetan, cefuroxime, cefprozil, cefaclor, and cefoxitin), a carbapenem/penem (i.e., imipenem, meropenem, ertapenem, faropenem and doripenem), a monobactam (i.e., aztreonam, tigemonam, norcardicin A and tabtoxinine-beta-lactam, a beta-lactamase inhibitor (i.e., clavulanic acid, tazobactam and sulbactam) in conjunction with another beta-lactam antibiotic, an aminoglycoside (i.e., amikacin, gentamicin, kanamycin, neomycin, netilmicin, streptomycin, tobramycin, and paromomycin), an ansamycin (i.e., geldanamycin and herbimycin), a carbacephem (i.e., loracarbef), a glycopeptides (i.e., teicoplanin and vancomycin), a macrolide (i.e., azithromycin, clarithromycin, dirithromycin, erythromycin, roxithromycin, troleandomycin, telithromycin and spectinomycin), a monobactam (i.e., aztreonam), a quinolone (i.e., ciprofloxacin, enoxacin, gatifloxacin, levofloxacin, lomefloxacin, moxifloxacin, norfloxacin, ofloxacin, trovafloxacin, grepafloxacin, sparfloxacin and temafloxacin), a sulfonamide (i.e., mafenide, sulfonamidochrysoidine, sulfacetamide, sulfadiazine, sulfamethizole, sulfanilamide, sulfasalazine, sulfisoxazole, trimethoprim, trimethoprim and sulfamethoxazole), a tetracycline (i.e., tetracycline, demeclocycline, doxycycline, minocycline and oxytetracycline), an antineoplastic or cytotoxic antibiotic (i.e., doxorubicin, mitoxantrone, bleomycin, daunorubicin, dactinomycin, epirubicin, idarubicin, plicamycin, mitomycin, pentostatin and valrubicin) and a miscellaneous antibacterial compound (i.e., bacitracin, colistin and polymyxin B)), an antifungal (i.e., metronidazole, nitazoxanide, tinidazole, chloroquine, iodoquinol and paromomycin), and an antiparasitic (including, but not limited to, quinine, chloroquine, amodiaquine, pyrimethamine, sulphadoxine, proguanil, mefloquine, atovaquone, primaquine, artemesinin, halofantrine, doxycycline, clindamycin, mebendazole, pyrantel pamoate, thiabendazole, diethylcarbamazine, ivermectin, rifampin, amphotericin B, melarsoprol, eflornithine and albendazole).

For ischemia, a neurological drug may be selected that includes, but is not limited to, a thrombolytic (i.e., urokinase, alteplase, reteplase and tenecteplase), a platelet aggregation inhibitor (i.e., aspirin, cilostazol, clopidogrel, prasugrel and dipyridamole), a statin (i.e., lovastatin, pravastatin, fluvastatin, rosuvastatin, atorvastatin, simvastatin, cerivastatin and pitavastatin), and a compound to improve blood flow or vascular flexibility, including, e.g., blood pressure medications.

For a behavioral disorder, a neurological drug may be selected from a behavior-modifying compound including, but not limited to, an atypical antipsychotic (i.e., risperidone, olanzapine, apripiprazole, quetiapine, paliperidone, asenapine, clozapine, iloperidone and ziprasidone), a phenothiazine antipsychotic (i.e., prochlorperazine, chlorpromazine, fluphenazine, perphenazine, trifluoperazine, thioridazine and mesoridazine), a thioxanthene (i.e., thiothixene), a miscellaneous antipsychotic (i.e., pimozide, lithium, molindone, haloperidol and loxapine), a selective serotonin reuptake inhibitor (i.e., citalopram, escitalopram, paroxetine, fluoxetine and sertraline), a serotonin-norepinephrine reuptake inhibitor (i.e., duloxetine, venlafaxine, desvenlafaxine, a tricyclic antidepressant (i.e., doxepin, clomipramine, amoxapine, nortriptyline, amitriptyline, trimipramine, imipramine, protriptyline and desipramine), a tetracyclic antidepressant (i.e., mirtazapine and maprotiline), a phenylpiperazine antidepressant (i.e., trazodone and nefazodone), a monoamine oxidase inhibitor (i.e., isocarboxazid, phenelzine, selegiline and tranylcypromine), a benzodiazepine (i.e., alprazolam, estazolam, flurazeptam, clonazepam, lorazepam and diazepam), a norepinephrine-dopamine reuptake inhibitor (i.e., bupropion), a CNS stimulant (i.e., phentermine, diethylpropion, methamphetamine, dextroamphetamine, amphetamine, methylphenidate, dexmethylphenidate, lisdexamfetamine, modafinil, pemoline, phendimetrazine, benzphetamine, phendimetrazine, armodafinil, diethylpropion, caffeine, atomoxetine, doxapram, and mazindol), an anxiolytic/sedative/hypnotic (including, but not limited to, a barbiturate (i.e., secobarbital, phenobarbital and mephobarbital), a benzodiazepine (as described above), and a miscellaneous anxiolytic/sedative/hypnotic (i.e. diphenhydramine, sodium oxybate, zaleplon, hydroxyzine, chloral hydrate, aolpidem, buspirone, doxepin, eszopiclone, ramelteon, meprobamate and ethclorvynol)), a secretin (see, e.g., Ratliff-Schaub et al. *Autism* 9: 256-265 (2005)), an opioid peptide (see, e.g., Cowen et al., *J. Neurochem.* 89:273-285 (2004)), and a neuropeptide (see, e.g., Hethwa et al. *Am. J. Physiol.* 289: E301-305 (2005)).

For CNS inflammation, a neurological drug may be selected that addresses the inflammation itself (i.e., a nonsteroidal anti-inflammatory agent such as ibuprofen or naproxen), or one which treats the underlying cause of the inflammation (i.e., an anti-viral or anti-cancer agent).

According to one embodiment of the invention, the "coupling" is achieved by generating a multispecific antibody (e.g. a bispecific antibody). Multispecific antibodies are monoclonal antibodies that have binding specificities for at least two different antigens or epitopes. In one embodiment, the multispecific antibody comprises a first antigen binding site which binds the BBB-R and a second antigen binding site which binds a brain antigen, such as beta-secretase 1 (BACE1) or Abeta, and the other brain antigens disclosed herein.

Figure 9A:
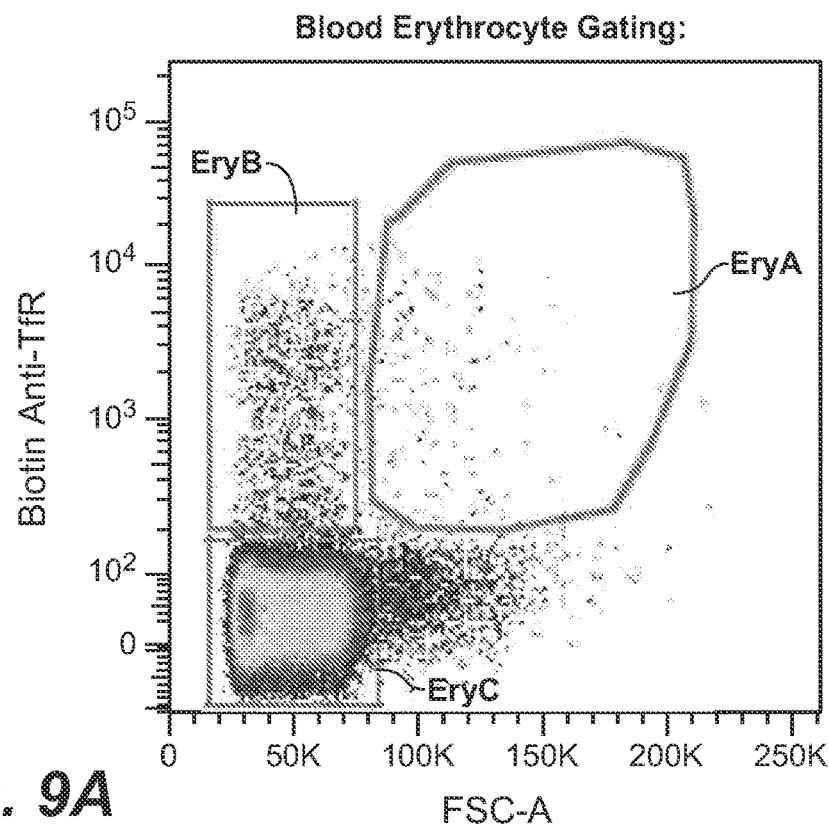
FIGS. 9A-9B and 10A-10D depict the results of experiments assessing the impact of an effectorless anti-TfR/BACE1 antibody on erythrocyte subpopulations in blood and bone marrow in mice. Distinct populations of Ter119-positive erythrocyte lineage in both (FIG. 9A) blood and (FIG. 9B) bone marrow are distinguished by their TfR expression and cell size (as determined by forward scatter profile) using flow cytometry (Paniga et al., PLoS One 6, 9 (2011)). Ter119-positive cell subsets in bone marrow were defined as EryA=large, TfR-positive early basophilic erythroblasts, EryB=small, TfR-positive polychromatic erythroblasts, and EryC=TfR-negative mature erythrocytes.
Figure 9B:
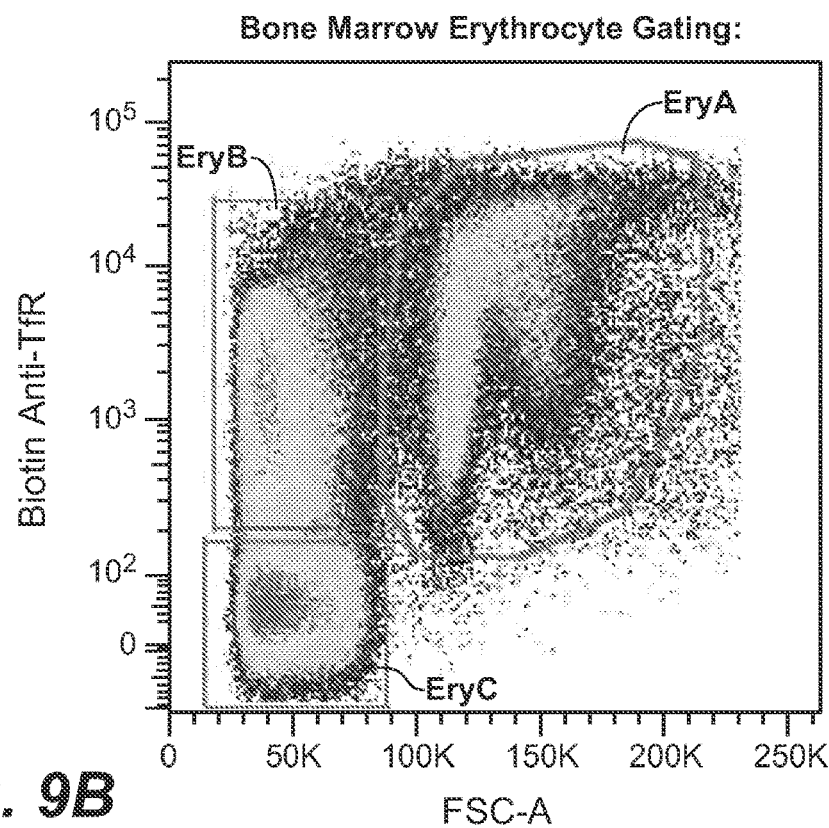

An exemplary brain antigen bound by such multispecific/bispecific antibody is BACE1, and an exemplary antibody binding thereto is the YW412.8.31 antibody in FIGS. 9A-B herein.

Figure 11A:
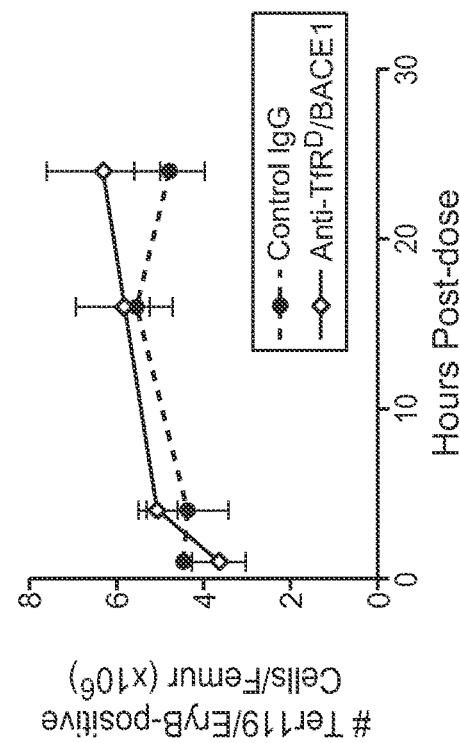
FIGS. 11A-11B and 12A-12D depict the results of experiments analyzing the impact of affinity and effector function of an anti-TfR/BACE1 antibody on erythrocyte populations in blood and bone marrow in mice.
Figure 11B:
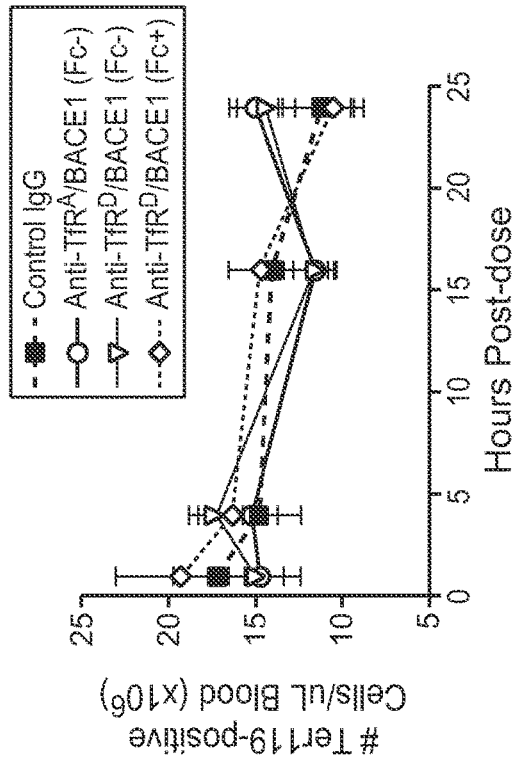

In another embodiment, the brain antigen is Abeta, exemplary such antibodies being described in WO2007068412, WO2008011348, WO20080156622, and WO2008156621, expressly incorporated herein by reference, with an exemplary Abeta antibody comprising the IgG4 MABT5102A antibody comprising the heavy and light chain amino acid sequences in FIGS. 11A and 11B, respectively.

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J.* 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al.,

*Science,* 229: 81 (1985)); using leucine zippers to produce bi-specific antibodies (see, e.g., Kostelny et al., *J. Immunol.,* 148(5):1547-1553 (1992)); using "diabody" technology for making bispecific antibody fragments (see, e.g., Hollinger et al., *Proc. Natl. Acad. Sci. USA,* 90:6444-6448 (1993)); and using single-chain Fv (sFv) dimers (see, e.g. Gruber et al., *J. Immunol.,* 152:5368 (1994)); and preparing trispecific antibodies as described, e.g., in Tutt et al. *J. Immunol.* 147: 60 (1991).

Engineered antibodies with three or more functional antigen binding sites, including "Octopus antibodies" or "dual-variable domain immunoglobulins" (DVDs) are also included herein (see, e.g. US 2006/0025576A1, and Wu et al. *Nature Biotechnology* (2007)).

The antibody or fragment herein also includes a "Dual Acting FAb" or "DAF" comprising an antigen binding site that binds to the BBB-R (e.g. TfR) as well as the brain antigen (e.g. BACE1) (see, US 2008/0069820, for example).

In one embodiment, the antibody is an antibody fragment, various such fragments being disclosed above. In another embodiment, the antibody is an intact or full-length antibody. Depending on the amino acid sequence of the constant domain of their heavy chains, intact antibodies can be assigned to different classes. There are five major classes of intact antibodies: IgA, IgD, IgE, IgG, and IgM, and several of these may be further divided into subclasses (isotypes), e.g., IgG1, IgG2, IgG3, IgG4, IgA, and IgA2. The heavy chain constant domains that correspond to the different classes of antibodies are called α, δ, ε, γ, and µ, respectively. The subunit structures and three-dimensional configurations of different classes of immunoglobulins are well known. In one embodiment, the intact antibody lacks effector function. In another embodiment, the inact antibody has reduced effector function.

Techniques for generating antibodies are known and examples provided above in the definitions section of this document. In one embodiment, the antibody is a chimeric, humanized, or human antibody or antigen-binding fragment thereof.

Various techniques are available for determining binding of the antibody to the BBB-R. One such assay is an enzyme linked immunosorbent assay (ELISA) for confirming an ability to bind to human BBB-R (and brain antigen). According to this assay, plates coated with antigen (e.g. recombinant BBB-R) are incubated with a sample comprising the anti-BBB-R antibody and binding of the antibody to the antigen of interest is determined.

In one aspect, an antibody of the invention is tested for its antigen binding activity, e.g., by known methods such as ELISA, Western blot, etc.

Assays for evaluating uptake of systemically administered antibody and other biological activity of the antibody can be performed as disclosed in the examples or as known for the anti-CNS antigen antibody of interest.

Exemplary assays where the multispecific antibody binds BACE1 shall now be described.

Competition assays may be used to identify an antibody that competes with any of the anti-BACE1 antibodies or Fabs descried herein, for example, YW412.8, YW412.8.31, YW412.8.30, YW412.8.2, YW412.8.29, YW412.8.51, Fab12, LC6, LC9, LC10 for binding to BACE1. In certain embodiments, such a competing antibody binds to the same epitope (e.g., a linear or a conformational epitope) that is bound by any of the anti-BACE1 antibodies or Fabs descried herein, for example, YW412.8, YW412.8.31, YW412.8.30, YW412.8.2, YW412.8.29, YW412.8.51, Fab12, LC6, LC9, LC10. Detailed exemplary methods for mapping an epitope to which an antibody binds are provided in Morris (1996) "Epitope Mapping Protocols," in *Methods in Molecular Biology* vol. 66 (Humana Press, Totowa, N.J.).

In an exemplary competition assay, immobilized BACE1 is incubated in a solution comprising a first labeled antibody that binds to BACE1 (e.g., YW412.8, YW412.8.31, YW412.8.30, YW412.8.2, YW412.8.29, YW412.8.51, Fab12, LC6, LC9, LC10) and a second unlabeled antibody that is being tested for its ability to compete with the first antibody for binding to BACE1. The second antibody may be present in a hybridoma supernatant. As a control, immobilized BACE1 is incubated in a solution comprising the first labeled antibody but not the second unlabeled antibody. After incubation under conditions permissive for binding of the first antibody to BACE1, excess unbound antibody is removed, and the amount of label associated with immobilized BACE1 is measured. If the amount of label associated with immobilized BACE1 is substantially reduced in the test sample relative to the control sample, then that indicates that the second antibody is competing with the first antibody for binding to BACE1. See Harlow and Lane (1988) *Antibodies: A Laboratory Manual* ch. 14 (Cold Spring Harbor Laboratory, Cold Spring Harbor, N.Y.).

In one aspect, assays are provided for identifying anti-BACE1 antibodies thereof having biological activity. Biological activity may include, e.g., inhibition of BACE1 aspartyl protease activity. Antibodies having such biological activity in vivo and/or in vitro are also provided, e.g. as evaluated by homogeneous time-resolved fluorescence HTRF assay or a microfluidic capillary electrophoretic (MCE) assay using synthetic substrate peptides, or in vivo in cell lines which express BACE1 substrates such as APP.

The antibody (including the multispecific antibody) herein is optionally recombinantly produced in a host cell transformed with nucleic acid sequences encoding its heavy and/or light chains (e.g. where the host cell or host cells have been transformed by one or more vectors with the nucleic acid therein). The host cell(s) is optionally a mammalian cell, for example a Chinese Hamster Ovary (CHO) cell.

B. Pharmaceutical Formulations

Therapeutic formulations of the antibodies used in accordance with the present invention are prepared for storage by mixing an antibody having the desired degree of purity with optional pharmaceutically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

The formulation herein may also contain more than one active compound as necessary, optionally those with complementary activities that do not adversely affect each other. The type and effective amounts of such medicaments depend, for example, on the amount of antibody present in the formulation, and clinical parameters of the subjects. Exemplary such medicaments are discussed below.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in, for example, Remington's Pharmaceutical Sciences 16th edition, Osol, A. Ed. (1980). One or more therapeutic agents may be encapsulated in liposomes that are coupled to anti-BBB-R (see e.g., U.S. Patent Application Publication No. 20020025313).

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

The formulations to be used for in vivo administration must be sterile. This is readily accomplished by filtration through sterile filtration membranes.

In one embodiment the formulation is isotonic.

C. Therapeutic Uses of Anti-BBB-R Antibodies

The anti-BBB-R antibodies (including multispecific antibodies comprising them) of the invention may be utilized in a variety of in vivo methods. For example, the invention provides a method of transporting a therapeutic compound across the blood-brain barrier with reduced or eliminated impact on red blood cell populations comprising exposing the anti-BBB-R antibody coupled to a therapeutic compound (e.g. a multispecific antibody which binds both the BBB-R and a brain antigen) to the BBB such that the antibody transports the therapeutic compound coupled thereto across the BBB. In another example, the invention provides a method of transporting a neurological disorder drug across the blood-brain barrier comprising exposing an anti-BBB-R antibody of the invention coupled to a brain disorder drug (e.g. a multispecific antibody which binds both the BBB-R and a brain antigen) to the BBB such that the antibody transports the neurological disorder drug coupled thereto across the BBB with reduced or eliminated impact on red blood cell populations. In one embodiment, the BBB here is in a mammal (e.g. a human), e.g. one which has a neurological disorder, including, without limitation: Alzheimer's disease (AD), stroke, dementia, muscular dystrophy (MD), multiple sclerosis (MS), amyotrophic lateral sclerosis (ALS), cystic fibrosis, Angelman's syndrome, Liddle syndrome, Parkinson's disease, Pick's disease, Paget's disease, cancer, traumatic brain injury, etc.

In one embodiment, neurological disorder is selected from: a neuropathy, an amyloidosis, cancer (e.g. involving the CNS or brain), an ocular disease or disorder, a viral or microbial infection, inflammation (e.g. of the CNS or brain), ischemia, neurodegenerative disease, seizure, behavioral disorder, lysosomal storage disease, etc.

Neuropathy disorders are diseases or abnormalities of the nervous system characterized by inappropriate or uncontrolled nerve signaling or lack thereof, and include, but are not limited to, chronic pain (including nociceptive pain), pain caused by an injury to body tissues, including cancer-related pain, neuropathic pain (pain caused by abnormalities in the nerves, spinal cord, or brain), and psychogenic pain (entirely or mostly related to a psychological disorder), headache, migraine, neuropathy, and symptoms and syndromes often accompanying such neuropathy disorders such as vertigo or nausea.

Amyloidoses are a group of diseases and disorders associated with extracellular proteinaceous deposits in the CNS, including, but not limited to, secondary amyloidosis, age-related amyloidosis, Alzheimer's Disease (AD), mild cognitive impairment (MCI), Lewy body dementia, Down's syndrome, hereditary cerebral hemorrhage with amyloidosis (Dutch type); the Guam Parkinson-Dementia complex, cerebral amyloid angiopathy, Huntington's disease, progressive supranuclear palsy, multiple sclerosis; Creutzfeld Jacob disease, Parkinson's disease, transmissible spongiform encephalopathy, HIV-related dementia, amyotropic lateral sclerosis (ALS), inclusion-body myositis (IBM), and ocular diseases relating to beta-amyloid deposition (i.e., macular degeneration, drusen-related optic neuropathy, and cataract).

Cancers of the CNS are characterized by aberrant proliferation of one or more CNS cell (i.e., a neural cell) and include, but are not limited to, glioma, glioblastoma multiforme, meningioma, astrocytoma, acoustic neuroma, chondroma, oligodendroglioma, medulloblastomas, ganglioglioma, Schwannoma, neurofibroma, neuroblastoma, and extradural, intramedullary or intradural tumors.

Ocular diseases or disorders are diseases or disorders of the eye, which for the purposes herein is considered a CNS organ segregated by the BBB. Ocular diseases or disorders include, but are not limited to, disorders of sclera, cornea, iris and ciliary body (i.e., scleritis, keratitis, corneal ulcer, corneal abrasion, snow blindness, arc eye, Thygeson's superficial punctate keratopathy, corneal neovascularisation, Fuchs' dystrophy, keratoconus, keratoconjunctivitis sicca, iritis and uveitis), disorders of the lens (i.e., cataract), disorders of choroid and retina (i.e., retinal detachment, retinoschisis, hypertensive retinopathy, diabetic retinopathy, retinopathy, retinopathy of prematurity, age-related macular degeneration, macular degeneration (wet or dry), epiretinal membrane, retinitis pigmentosa and macular edema), glaucoma, floaters, disorders of optic nerve and visual pathways (i.e., Leber's hereditary optic neuropathy and optic disc drusen), disorders of ocular muscles/binocular movement accommodation/refraction (i.e., strabismus, ophthalmoparesis, progressive external opthalmoplegia, esotropia, exotropia, hypermetropia, myopia, astigmatism, anisometropia, presbyopia and ophthalmoplegia), visual disturbances and blindness (i.e., amblyopia, Lever's congenital amaurosis, scotoma, color blindness, achromatopsia, nyctalopia, blindness, river blindness and micro-opthalmia/coloboma), red eye, Argyll Robertson pupil, keratomycosis, xerophthalmia and andaniridia.

Viral or microbial infections of the CNS include, but are not limited to, infections by viruses (i.e., influenza, HIV, poliovirus, rubella,), bacteria (i.e., *Neisseria* sp., *Streptococcus* sp., *Pseudomonas* sp., *Proteus* sp., *E. coli*, *S. aureus*, *Pneumococcus* sp., *Meningococcus* sp., *Haemophilus* sp., and *Mycobacterium tuberculosis*) and other microorganisms such as fungi (i.e., yeast, *Cryptococcus neoformans*), parasites (i.e., *Toxoplasma gondii*) or amoebas resulting in CNS pathophysiologies including, but not limited to, meningitis, encephalitis, myelitis, vasculitis and abscess, which can be acute or chronic.

Inflammation of the CNS includes, but is not limited to, inflammation that is caused by an injury to the CNS, which can be a physical injury (i.e., due to accident, surgery, brain trauma, spinal cord injury, concussion) and an injury due to or related to one or more other diseases or disorders of the CNS (i.e., abscess, cancer, viral or microbial infection).

Ischemia of the CNS, as used herein, refers to a group of disorders relating to aberrant blood flow or vascular behavior in the brain or the causes therefor, and includes, but is not limited to: focal brain ischemia, global brain ischemia, stroke (i.e., subarachnoid hemorrhage and intracerebral hemorrhage), and aneurysm.

Neurodegenerative diseases are a group of diseases and disorders associated with neural cell loss of function or death in the CNS, and include, but are not limited to: adrenoleukodystrophy, Alexander's disease, Alper's disease, amyotrophic lateral sclerosis, ataxia telangiectasia, Batten disease, cockayne syndrome, corticobasal degeneration, degeneration caused by or associated with an amyloidosis, Friedreich's ataxia, frontotemporal lobar degeneration, Kennedy's disease, multiple system atrophy, multiple sclerosis, primary lateral sclerosis, progressive supranuclear palsy, spinal muscular atrophy, transverse myelitis, Refsum's disease, and spinocerebellar ataxia.

Seizure diseases and disorders of the CNS involve inappropriate and/or abnormal electrical conduction in the CNS, and include, but are not limited to epilepsy (i.e., absence seizures, atonic seizures, benign Rolandic epilepsy, childhood absence, clonic seizures, complex partial seizures, frontal lobe epilepsy, febrile seizures, infantile spasms, juvenile myoclonic epilepsy, juvenile absence epilepsy, Lennox-Gastaut syndrome, Landau-Kleffner Syndrome, Dravet's syndrome, Otahara syndrome, West syndrome, myoclonic seizures, mitochondrial disorders, progressive myoclonic epilepsies, psychogenic seizures, reflex epilepsy, Rasmussen's Syndrome, simple partial seizures, secondarily generalized seizures, temporal lobe epilepsy, tonicclonic seizures, tonic seizures, psychomotor seizures, limbic epilepsy, partial-onset seizures, generalized-onset seizures, status epilepticus, abdominal epilepsy, akinetic seizures, autonomic seizures, massive bilateral myoclonus, catamenial epilepsy, drop seizures, emotional seizures, focal seizures, gelastic seizures, Jacksonian March, Lafora Disease, motor seizures, multifocal seizures, nocturnal seizures, photosensitive seizure, pseudo seizures, sensory seizures, subtle seizures, sylvan seizures, withdrawal seizures, and visual reflex seizures).

Behavioral disorders are disorders of the CNS characterized by aberrant behavior on the part of the afflicted subject and include, but are not limited to: sleep disorders (i.e., insomnia, parasomnias, night terrors, circadian rhythm sleep disorders, and narcolepsy), mood disorders (i.e., depression, suicidal depression, anxiety, chronic affective disorders, phobias, panic attacks, obsessive-compulsive disorder, attention deficit hyperactivity disorder (ADHD), attention deficit disorder (ADD), chronic fatigue syndrome, agoraphobia, post-traumatic stress disorder, bipolar disorder), eating disorders (i.e., anorexia or bulimia), psychoses, developmental behavioral disorders (i.e., autism, Rett's syndrome, Aspberger's syndrome), personality disorders and psychotic disorders (i.e., schizophrenia, delusional disorder, and the like).

Lysosomal storage disorders are metabolic disorders which are in some cases associated with the CNS or have CNS-specific symptoms; such disorders include, but are not limited to: Tay-Sachs disease, Gaucher's disease, Fabry disease, mucopolysaccharidosis (types I, II, III, IV, V, VI and VII), glycogen storage disease, GM1-gangliosidosis, metachromatic leukodystrophy, Farber's disease, Canavan's leukodystrophy, and neuronal ceroid lipofuscinoses types 1 and 2, Niemann-Pick disease, Pompe disease, and Krabbe's disease.

In another embodiment, diseases related to or caused by inappropriate overproduction of red blood cells, or wherein the overproduction of red blood cells is an effect of the disease, can be prevented or treated by the reticulocyte-depleting effect recognized herein of anti-TfR antibodies retaining at least partial effector function. For example, in congenital or neoplastic polycythemia vera, elevated red blood cell counts due to hyperproliferation of, e.g., reticulocytes, results in thickening of blood and concomitant physiological symptoms (d'Onofrio et al., Clin. Lab. Haematol. (1996) Suppl. 1: 29-34). Administration of an anti-TfR antibody of the invention wherein at least with at least partial effector function of the antibody was preserved would permit selective removal of immature reticulocyte populations without impacting normal transferrin transport into the CNS. Dosing of such an antibody could be modulated such that acute clinical symptoms could be minimized (ie, by dosing at a very low dose or at widely-spaced intervals), as well-understood in the art.

In one aspect, an antibody of the invention is used to detect a neurological disorder before the onset of symptoms and/or to assess the severity or duration of the disease or disorder. In one aspect, the antibody permits detection and/or imaging of the neurological disorder, including imaging by radiography, tomography, or magnetic resonance imaging (MRI).

In one aspect, a low affinity anti-BBB-R antibody of the invention for use as a medicament is provided. In further aspects, a low affinity anti-BBB-R antibody for use in treating a neurological disease or disorder (e.g., Alzheimer's disease) without depleting red blood cells (ie, reticulocytes) is provided. In certain embodiments, a modified low affinity anti-BBB-R antibody for use in a method of treatment as described herein is provided. In certain embodiments, the invention provides a low affinity anti-BBB-R antibody modified to improve its safety for use in a method of treating an individual having a neurological disease or disorder comprising administering to the individual an effective amount of the anti-BBB-R antibody (optionally coupled to a neurological disorder drug). In one such embodiment, the method further comprises administering to the individual an effective amount of at least one additional therapeutic agent. In further embodiments, the invention provides an anti-BBB-R antibody modified to improve its safety for use in reducing or inhibiting amlyoid plaque formation in a patient at risk or suffering from a neurological disease or disorder (e.g., Alzheimer's disease). An "individual" according to any of the above embodiments is optionally a human. In certain aspects, the anti-BBB-R antibody of the invention for use in the methods of the invention improves uptake of the neurological disorder drug with which it is coupled.

In a further aspect, the invention provides for the use of a low affinity anti-BBB-R antibody of the invention in the manufacture or preparation of a medicament. In one embodiment, the medicament is for treatment of neurological disease or disorder. In a further embodiment, the medicament is for use in a method of treating neurological disease or disorder comprising administering to an individual having neurological disease or disorder an effective amount of the medicament. In one such embodiment, the method further comprises administering to the individual an effective amount of at least one additional therapeutic agent.

In a further aspect, the invention provides a method for treating Alzheimer's disease. In one embodiment, the method comprises administering to an individual having Alzheimer's disease an effective amount of a multispecific antibody of the invention which binds both BACE1 and TfR or both Abeta and TfR. In one such embodiment, the method further comprises administering to the individual an effective amount of at least one additional therapeutic agent. An "individual" according to any of the above embodiments may be a human.

The anti-BBB-R antibodies of the invention can be used either alone or in combination with other agents in a therapy. For instance, the anti-BBB-R antibody of the invention may be co-administered with at least one additional therapeutic agent. In certain embodiments, an additional therapeutic agent is a therapeutic agent effective to treat the same or a different neurological disorder as the anti-BBB-R antibody is being employed to treat. Exemplary additional therapeutic agents include, but are not limited to: the various neurological drugs described above, cholinesterase inhibitors (such as donepezil, galantamine, rovastigmine, and tacrine), NMDA receptor antagonists (such as memantine), amyloid beta peptide aggregation inhibitors, antioxidants, γ-secretase modulators, nerve growth factor (NGF) mimics or NGF gene therapy, PPARγ agonists, HMS-CoA reductase inhibitors (statins), ampakines, calcium channel blockers, GABA receptor antagonists, glycogen synthase kinase inhibitors, intravenous immunoglobulin, muscarinic receptor agonists, nicotinic receptor modulators, active or passive amyloid beta peptide immunization, phosphodiesterase inhibitors, serotonin receptor antagonists and anti-amyloid beta peptide antibodies. In certain embodiments, the at least one additional therapeutic agent is selected for its ability to mitigate one or more side effects of the neurological drug.

As exemplified herein, certain anti-BBB-R antibodies may have side effects that negatively impact reticulocyte populations in a subject treated with the anti-BBB-R antibody. Thus, in certain embodiments, at least one further therapeutic agent selected for its ability to mitigate such negative side effect on reticulocyte populations is coadministered with an anti-BBB-R antibody of the invention. Examples of such therapeutic agents include, but are not limited to, agents to increase red blood cell (ie, reticulocyte) populations, agents to support growth and development of red blood cells (ie, reticulocytes), and agents to protect red blood cell populations from the effects of the anti-BBB-R antibody; such agents include, but are not limited to, erythropoietin (EPO), iron supplements, vitamin C, folic acid, and vitamin B12, as well as physical replacement of red blood cells (ie, reticulocytes) by, for example, transfusion with similar cells, which may be from another individual of similar blood type or may have been previously extracted from the subject to whom the anti-BBB-R antibody is administered. It will be understood by one of ordinary skill in the art that in some instances, agents intended to protect existing red blood cells (ie, reticulocytes) are preferably administered to the subject preceding or concurrent with the anti-BBB-R antibody therapy, while agents intended to support or initiate the regrowth/development of red blood cells or blood cell populations (ie, reticulocytes or reticulocyte populations) are preferably administered concurrent with or after the anti-BBB-R antibody therapy such that such blood cells can be replenished after the anti-BBB-R antibody treatment.

In certain other such embodiments, the at least one further therapeutic agent is selected for its ability to inhibit or prevent the activation of the complement pathway upon administration of the anti-BBB-R antibody. Examples of such therapeutic agents include, but are not limited to, agents that interfere with the ability of the anti-BBB-R antibody to bind to or activate the complement pathway and agents that inhibit one or more molecular interactions within the complement pathway, and are described generally in Mollnes and Kirschfink (2006) Molec. Immunol. 43:107-121, the contents of which are expressly incorporated herein by reference.

Such combination therapies noted above encompass combined administration (where two or more therapeutic agents are included in the same or separate formulations), and separate administration, in which case, administration of the antibody of the invention can occur prior to, simultaneously, and/or following, administration of the additional therapeutic agent and/or adjuvant. Antibodies of the invention can also be used in combination with other interventional therapies such as, but not limited to, radiation therapy, behavioral therapy, or other therapies known in the art and appropriate for the neurological disorder to be treated or prevented.

The anti-BBB-R antibody of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various timepoints, bolus administration, and pulse infusion are contemplated herein.

Antibodies of the invention are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question or to prevent, mitigate or ameliorate one or more side effects of antibody administration. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 µg/kg to 15 mg/kg (e.g. 0.1 mg/kg-10 mg/kg) of antibody can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. However, other dosage regimens may be useful. It will be appreciated that one method to reduce impact on reticulocyte populations by administration of anti-TfR antibodies is to modify the amount or timing of the doses such that overall lower quantities of circulating antibody are present in the bloodstream to interact with reticulocytes. In one nonlimiting example, a lower dose of the anti-TfR antibodies may be administered with greater frequency than a higher dose would be. The dosage used may be balanced between the amount of antibody necessary to be delivered to the CNS (itself related to the affinity of the CNS antigen-specific portion of the antibody), the affinity of that antibody for TfR, and whether or not red blood cell (ie, reticulocyte)-protecting, growth and development-stimulating, or complement pathway-inhibiting compound(s) are being co- or serially administered with the antibody. The progress of this therapy is easily monitored by conventional techniques and assays as described herein and as known in the art.

It is understood that any of the above formulations or therapeutic methods may be carried out using an immunoconjugate of the invention in place of or in addition to an anti-BBB-R antibody.

D. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate of the invention in place of or in addition to an anti-BBB-R antibody.

The article of manufacture optionally further comprises a package insert with instructions for treating a neurological disorder in a subject, wherein the instructions indicate that treatment with the antibody as disclosed herein treats the neurological disorder, and optionally indicates that the antibody has improved uptake across the BBB due to its low affinity for the BBB-R.

EXAMPLES

Example 1: Generation and Characterization of Low-Affinity Anti-TfR Antibodies

The field has recognized that the natural ability of the transferrin receptor (TfR) to transport transferrin across the blood-brain barrier (BBB) may be exploited to permit the transport of heterologous molecules into the brain from the bloodstream (see, e.g., WO9502421). Applicants previously developed an important modification to this system, (*Sci. Transl. Med.* 3, 84ra43 (2011)) namely that transport into the brain and retention in the brain of a heterologous molecule conjugated to an anti-transferrin receptor antibody (anti-TfR) was substantially enhanced by decreasing the affinity of the anti-TfR for transferrin receptor, within a certain range.

A panel of anti-TfR antibodies was generated with progressively lessening affinities for murine TfR, three of which (designated anti-TfR$^A$, anti-TfR$^D$, and anti-TfR$^E$) were further modified into a bispecific format with the other antibody arm being specific for BACE1. Each monospecific and bispecific antibody was assessed in a competition ELISA assay for its affinity for murine TfR. Briefly, the assay was performed in maxisorp plates (Neptune, N. J) coated with 2.5 µg/ml of purified muTfR tagged with a hexahistidine tag (muTfR-His) in PBS at 4° C. overnight. Plates were washed with PBS/0.05% Tween 20 and blocked using Superblock blocking buffer in PBS (Thermo Scientific, Hudson, N.H.). A 1:3 serial titrated bivalent IgG (anti-TfR$^A$, anti-TfR$^D$, anti-TfR$^E$) or bi-specific Ab (anti-TfR$^A$/BACE1, anti-TfR$^D$/BACE1, or anti-TfR$^E$/BACE1) was combined with 1 nM biotinylated anti-TfR$^A$ and added to the plate for 1 hour at room temperature. Plates were washed with PBS/0.05% Tween 20 and HRP-streptavidin (SouthernBiotech, Birmingham) was added the plate and incubated for 1 hour at room temperature. Plates were washed with PBS/0.05% Tween 20 and biotinylated anti-TfR$^A$ bound to the plate was detected using TMB substrate (BioFX Laboratories, Owings Mills). (FIG. 1A). The observed IC50 values for the binding of each monospecific or bispecific antibody to murine TfR in the assay are shown in Table 2.

TABLE 2

IC$_{50}$ values for antibody binding by competition ELISA

| Antibody | IC$_{50}$ |
|---|---|
| TfR$^A$ | 1 nM |
| TfR$^D$ | 66 nM |
| TfR$^E$ | 20 µM |
| TfR$^A$/BACE1 | 14 nM |
| TfR$^D$/BACE1 | 1.6 µM |
| TfR$^E$/BACE1 | 95 µM |

Antibody distribution post a single administration in mice was performed as follows. Wild type female C57B/6 mice ages 6-8 weeks were used for all studies. The animals' care was in accordance with institutional guidelines. Mice were intravenously injected with 50 mg/kg of either a control IgG, anti-BACE1 or an anti-TfR/BACE1 variant. Total injection volume did not exceed 250 uL and antibodies were diluted in D-PBS when necessary (Invitrogen). After the indicated time, mice were perfused with D-PBS at a rate of 2 mL/min for 8 minutes. Brains were extracted and the cortex and hippocampus was isolated, homogenized in 1% NP-40 (Cal-Biochem) in PBS containing Complete Mini EDTA-free protease inhibitor cocktail tablets (Roche Diagnostics). Homogenized brain samples were rotated at 4° C. for 1 hour before spinning at 14,000 rpm for 20 minutes. The supernatant was isolated for brain antibody measurement. Whole blood was collected prior to perfusion in EDTA microtainer tubes (BD Diagnostics), allowed to sit for 30 minutes at room temperature, and spun down at 5000×g for 10 minutes. The top layer of plasma was transferred to new tubes for antibody and mouse Aβ$_{1-40}$ measurements.

Total antibody concentrations in mouse plasma and brain samples were measured using an anti-huFc/anti-huFc ELISA. NUNC 384-well Maxisorp immunoplates (Neptune, N.J.) were coated with the F(ab')$_2$ fragment of donkey anti-human IgG, an Fc fragment-specific polyclonal antibody (Jackson ImmunoResearch, West Grove, Pa.), overnight at 4° C. Plates were blocked with PBS, 0.5% BSA for 1 hour at 25° C. Each antibody (control IgG, anti-BACE1, and anti-TfR/BACE1 bispecific variants) was used as a standard to quantify respective antibody concentrations. Plates were washed with PBS, 0.05% Tween-20 using a microplate washer (Bio-Tek Instruments, Inc., Winooski, Vt.), and standards and samples diluted in PBS containing 0.5% BSA, 0.35 M NaCl, 0.25% CHAPS, 5 mM EDTA, 0.05% Tween-20 and 15 ppm Proclin® (Sigma-Aldrich) were added for two hours at 25° C. Bound antibody was detected with horseradish peroxidase-conjugated F(ab')2 goat anti-human IgG, an Fc specific polyclonal antibody (Jackson ImmunoResearch). Samples were developed using 3,3',5,5'-tetramethyl benzidine (TMB) (KPL, Inc., Gaithersburg, Md.) and absorbance measured at 450 nm on a Multiskan Ascent reader (Thermo Scientific, Hudson, N.H.). Concentrations were determined from the standard curve using a four-parameter non-linear regression program. The assay had lower limit of quantification (LLOQ) values of 3.12 ng/ml in serum and 12.81 ng/g in brain. Statistical analysis of differences between experimental groups was performed using a two-tailed unpaired t-test.

Figure 1B:
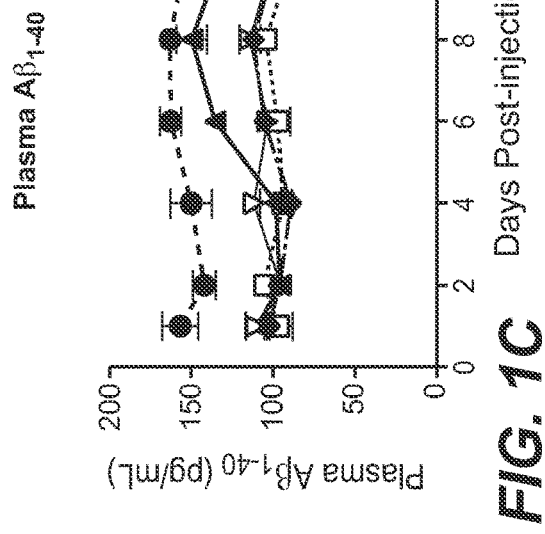
Figure 1C:
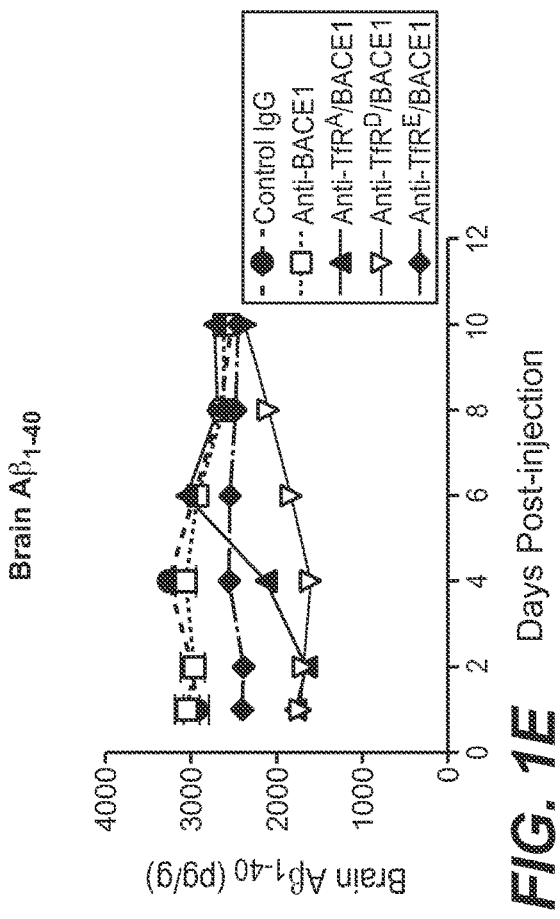
Figure 1D:
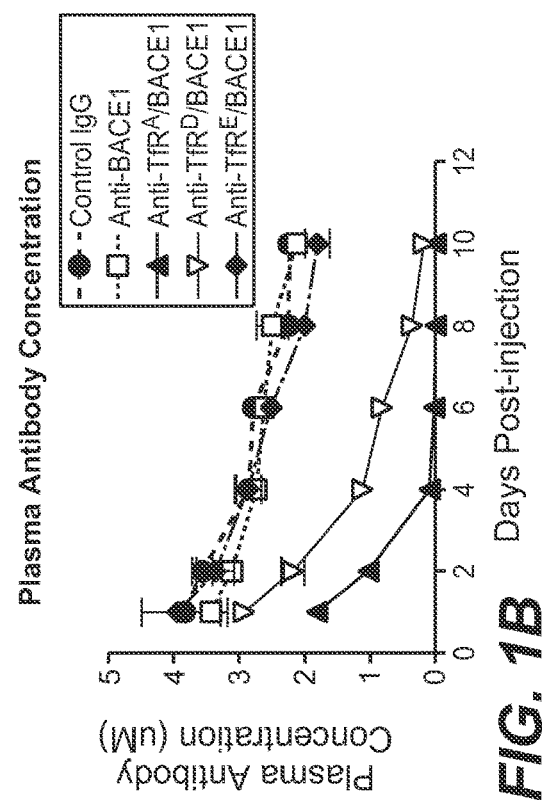

The results are shown in FIGS. 1B and 1D. Both the control IgG and the anti-BACE1 antibody had limited uptake into the brain that persisted over the 10-day measurement period, while their plasma concentrations were the highest of any of the tested molecules at all time points, despite gradual clearance over time. Of the three anti-TfR/BACE1 variants assessed, anti-TfR$^A$/BACE1 and anti-TfR$^D$/BACE1 both showed between 35 and 40 nM concentrations in the brain at 1 day post-dose (7-8-fold greater than the control IgG; FIG. 1D). However, the concentration of anti-TfR$^A$/BACE1 in the brain decreased rapidly after day 2 and returned to control levels by day 6. Anti-TfR$^D$/BACE1 persisted longer in the brain than anti-TfR$^A$/BACE1, with a more gradual decline in brain concentrations; however, by day 10 the concentration matched that of the control. Anti-TfR$^E$/BACE1 had a much more moderate entry into the brain (2-3-fold control), but the decline over subsequent days was much less than that of the other two antibody variants. Plasma levels of all three antibody variants (FIG. 1B) declined over time. Anti-TfR$^A$/BACE1 was completely cleared from the plasma by day 4, while anti-TfR$^D$/BACE1 was fully cleared by day 10, and anti-TfR$^E$/BACE1 still persisted in the plasma at a level comparable to that of the control IgG or anti-BACE1.

Taken together, these findings were consistent with the previous discovery that a reduction in the affinity of an antibody for TFR actually improves its retention in the brain, since the highest affinity antibody used (anti-TfR$^A$/BACE1) was the most rapidly cleared from the brain and the lowest affinity antibody used (anti-TfR$^E$/BACE1) persisted the longest in the brain. However, it was also clear from the data that the total amount of anti-TfR$^D$/BACE1 that was transported into the brain over time was much greater than that of anti-TfR$^E$/BACE1 suggesting that there is an optimum affinity between anti-TfR$^D$/BACE1 and anti-TfR$^E$/BACE1 to maximize both transport across the BBB and persistence in the brain.

The presence and persistence of the transported molecule in the brain and plasma is only one measure of potential efficacy; of further interest is the activity of the molecule in those compartments. Accordingly, the BACE1 enzyme activity was assessed in both compartments by measuring the amount of Aβ$_{1-40}$ (a cleavage byproduct of BACE1 enzymatic activity on amyloid precursor protein (APP)). Briefly, antibody treatment and perfusions were performed in wild type mice as stated above. For Aβ$_{1-40}$ measurements, hemi-brains were homogenized in 5M guanidine hydrochloride buffer and samples rotated for 3 hours at room temperature prior to diluting (1:10) in 0.25% casein, 5 mM EDTA (pH 8.0) in PBS containing freshly added aprotinin (20 mg/mL) and leupeptin (10 mg/mL). Diluted homogenates were spun at 14,000 rpm for 20 min. and supernatants were isolated for Aβ$_{1-40}$ measurement. Plasma was prepared as described above. The concentrations of total mouse Aβ$_{1-40}$ in plasma and brain were determined using a sandwich ELISA following similar procedures described above. Hemi-brains for Aβ$_{1-40}$ measurement were homogenized in 1% NP-40 (Cal-*Biochem*) and rotated for 1 hour at room temperature prior to spinning at 14,000 rpm for 20 minutes. Rabbit polyclonal antibody specific for the C-terminus of Aβ$_{1-40}$ (Millipore, Bedford, Mass.) was coated onto plates, and biotinylated anti-mouse Aβ monoclonal antibody M3.2 (Covance, Dedham, Mass.) was used for detection. The assay had LLOQ values of 1.96 pg/ml in plasma and 39.1 pg/g in brain. Statistical analysis of differences between experimental groups was performed using a two-tailed unpaired t-test.

Figure 1E:
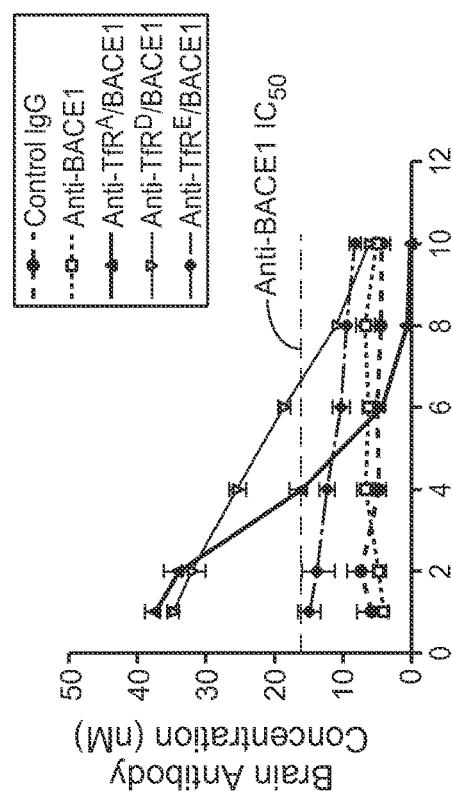

The results for plasma and brain are shown in FIGS. 1C and 1E, respectively, and are consistent with the amount of antibody present in each compartment at the indicated time (see FIGS. 1B and 1D). Importantly, the amount of Aβ$_{1-40}$ observed in the brain over time was lowest over the longest period in the mice treated with anti-TfR$^D$/BACE1.

Example 2a: Effect of Anti-TfR Dosing on Reticulocytes

Unexpectedly, upon treatment of mice with monospecific anti-TfR$^A$ or anti-TfR$^D$ at all dose levels of 1 mg/kg or higher, unusual and acute clinical signs were observed that were not observed in mice treated with bispecific anti-TfR$^A$/BACE1 or anti-TfR$^D$/BACE1 (see Table 3).

TABLE 3

SYMPTOMS OBSERVED IN MICE AFTER ANTIBODY ADMINISTRATION

| Antibody | Dose (mg/kg) | Acute Clinical Signs |
| --- | --- | --- |
| Control IgG (isotype matched) | 50* | None |
| Anti-TfR$^D$ (comprising effector function) | 0.01* | None |
| | 0.1 | |
| | 1 | Profound post-dose lethargy within 5 minutes |
| | 5 | Occasional spastic movements in few animals |
| | 25 | Scruffy, hunched appearance by 20-25 minutes post-dose |
| | 50 | Red urine observed from some mice Completely reversible within hours |
| Anti-TfR$^D$/Bace (not comprising effector function) | 1* | None |
| | 5* | |
| | 25 | |
| | 50 | |
| | 200 | |

*No reticulocyte decreases observed at these dose levels

Figure 2A:
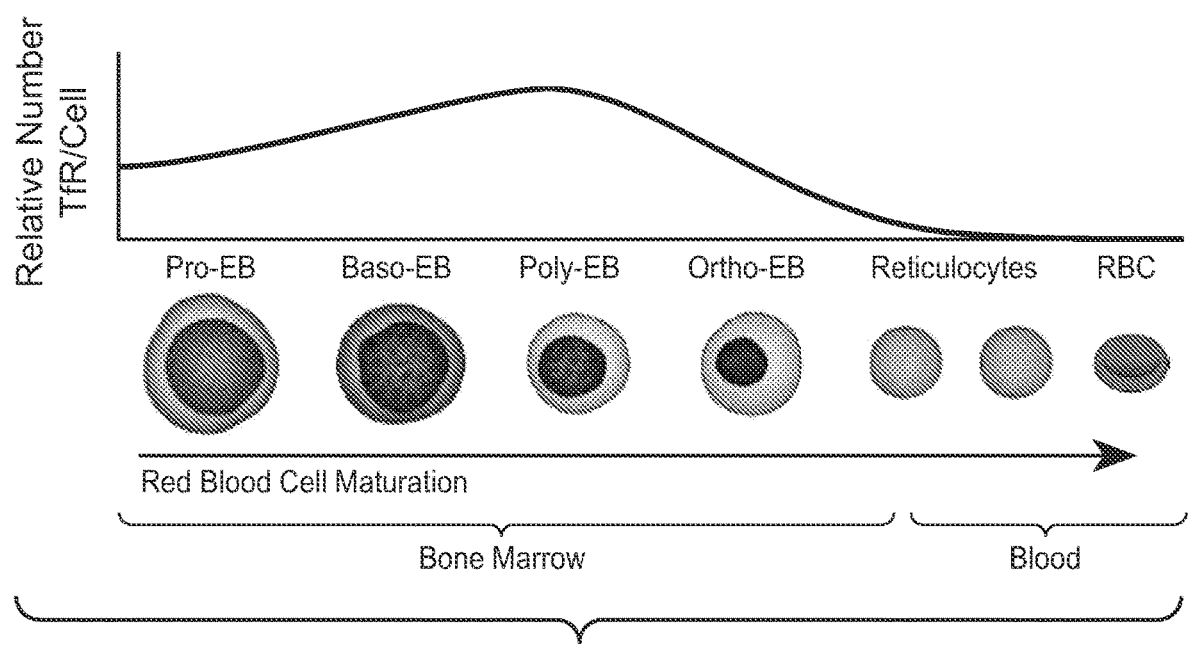
FIG. 2A is a schematic depiction of red blood cell (RBC) maturation in the bone marrow, showing progression from the pro-erythroblast (Pro-EB), to basophilic erythroblast (Baso-EB), to polychromatic erythroblast (Poly-EB), to orthochromatic erythroblast (Ortho-EB) and finally to the reticulocyte. Reticulocytes are released from the bone marrow to the circulation where they mature to RBCs. During the later stages of maturation in the bone marrow, erythroid precursors synthesize the iron-containing protein hemoglobin, which requires a concomitant increase in TfR expression. Transferrin receptors are shed with the cessation of hemoglobin synthesis and cell proliferation as cells mature through the reticulocyte stage, such that mature RBCs do not express TfR. The relative number of TfR present at each cell stage of RBC maturation is indicated in the graph at the top of the figure, based on data from Iacpetta et al., Biochim. Biophys. Acta 687: 204-210 (1982).

Specifically, the monospecific-treated mice displayed post-dose lethargy within 5 minutes of the treatment, where they became immobile and non-responsive (with occasional spastic movements in some animals), followed by development of a scruffy, hunched appearance by 20-25 minutes post-dose. All such observed effects vanished within hours after the treatment. Certain monospecific antibody-treated mice also appeared to present with occasional presence of blood in the urine, as well as apparent hypotension at 1 hour post-dose based on difficult with terminal cardiac blood collection compared to collection in bispecific-treated animals. Because mouse immature red blood cells are known to express TfR (see FIG. 2A), to exist in the peripheral bloodstream, and the observed effects in mice may be explained if such blood cells were injured, the impact of the antibody treatment on immature red blood cells (reticulocytes) was investigated in mice.

Mice were dosed intravenously with a single 1 mg/kg, 5 mg/kg, or 50 mg/kg anti-TfR$^D$ or anti-TfR$^D$/BACE1 injection, or with a single 50 mg/kg control IgG injection using the same procedure as described in Example 1, and whole blood samples were taken at 1 hour post-dose and placed into potassium-EDTA-containing collection tubes. Red cell and reticulocyte counts and indices were determined on these blood samples using the Sysmex XT2000iV (Sysmex, Kobe, Japan) according to the manufacturer's instructions. Briefly, the Sysmex detects and classifies total reticulocytes as well as the immature reticulocyte fraction (sum of high and middle/intermediate fluorescent reticulocytes) by flow cytometry using a fluorescent polymethine dye to bind cellular RNA and measure the resulting cell light scatter characteristics.

Figure 2B:
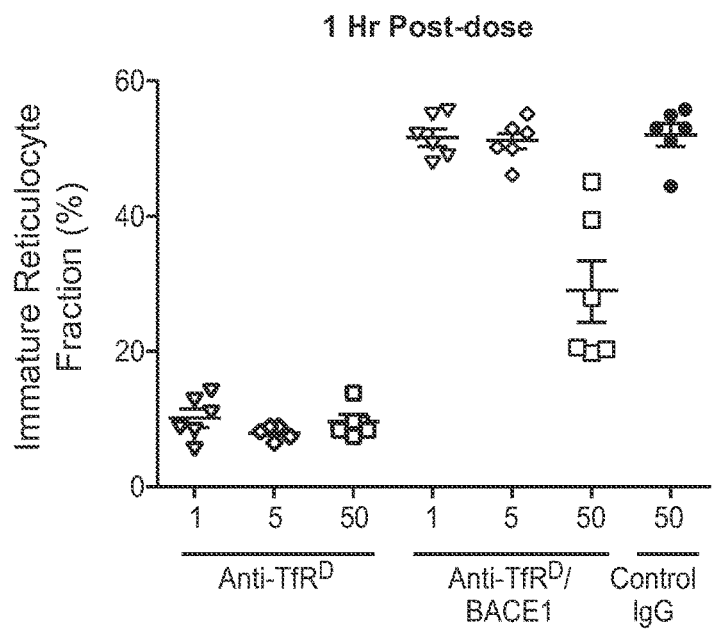
FIGS. 2B and 2C depict the results of experiments assessing the impact of anti-TfR and anti-TfR/BACE1 administration on reticulocytes in mice, as described in Example 2A.

At 1 hour post-dose, anti-TfR$^D$ reduced immature reticulocyte levels at all dose levels tested, to approximately the same extent regardless of dose. Treated mice in each anti-TfR$^D$ dosage group also showed acute clinical signs of similar severity and penetrance (see FIG. 2B). In contrast, blood samples from the 1 mg/kg and 5 mg/kg anti-TfR$^D$/BACE1-treated mice had similar fractions of immature reticulocytes as those from the control-IgG-treated samples. The 50 mg/kg anti-TfR$^D$/BACE1-treated mice showed a marked reduction in reticulocytes (to about 50% of control amounts) (FIG. 2B), but this reduction was not accompanied by any acute clinical signs. Thus, the bispecific anti-TfR$^D$-containing antibody had a lesser impact on reticulocyte levels than monospecific anti-TfR$^D$, and did not elicit acute adverse clinical signs.

Figure 2C:
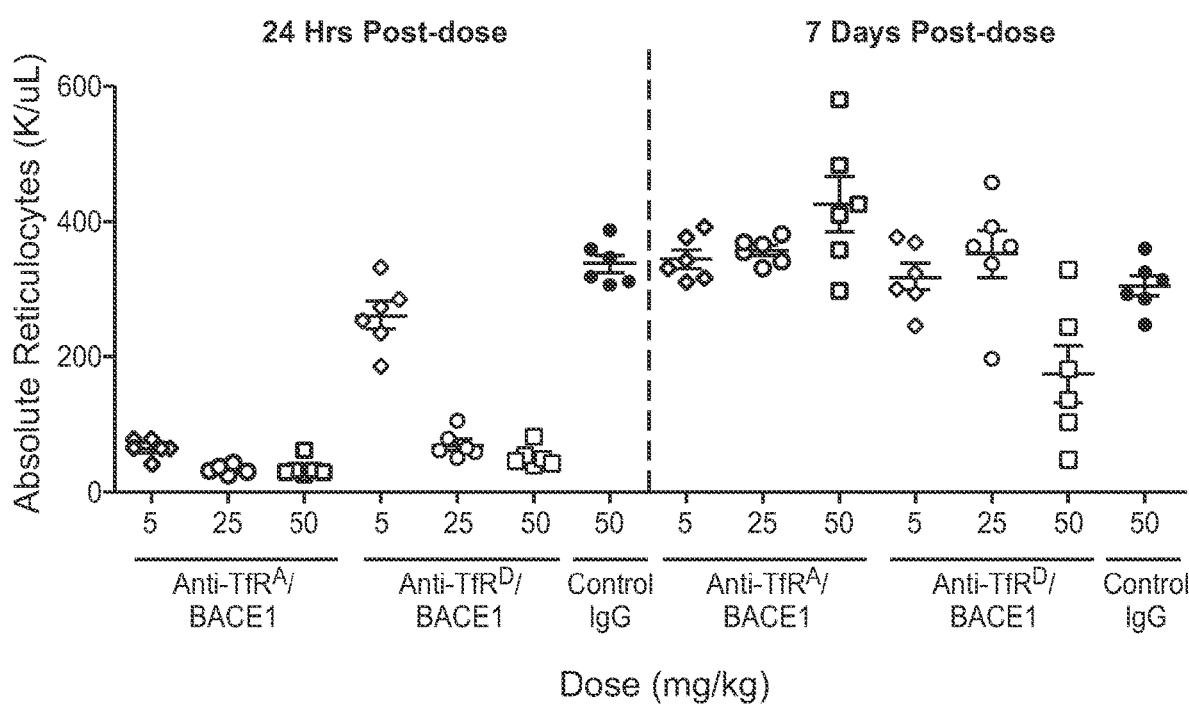

The experiment was repeated, further including a second bispecific antibody of a different affinity for TfR. Mice were dosed intravenously with a single 5 mg/kg, 25 mg/kg or 50 mg/kg anti-TfR$^A$/BACE1 or anti-TfR$^D$/BACE1 injection, or with a single 50 mg/kg control IgG injection using the same procedure as described in Example 1, and blood samples were taken at 24 hours and 7 days post-dose. Reticulocyte counts were measured in whole blood as described above. The results are shown in FIG. 2C. At 24 hours post-dose, all of the anti-TfR$^A$/BACE1-treated mouse samples showed similar marked reductions in total reticulocyte count. The 25 mg/kg and 50 mg/kg anti-TfR$^D$/BACE1-treated samples showed similarly low reticulocyte counts as the anti-TfR$^A$/BACE1-treated samples. However, the 5 mg/kg anti-TfR$^D$/BACE1-treated samples showed only a modest reduction in reticulocyte numbers relative to the IgG control sample at 24 hours post-dose. By 7 days post-dose, all groups showed normal levels of reticulocytes (FIG. 2C) suggesting recovery from the initial reticulocyte depletion, with the exception of the 50 mg/kg anti-TfR$^D$/BACE1 sample, which showed a sustained reduction in reticulocyte levels (approximately 50%) relative to the control amounts. Thus, only the lowest tested dose of anti-TfR$^D$/BACE1 had a moderate impact on reticulocytes, while all other tested doses led to an almost complete loss of reticulocytes at 24 hours post-dose, indicating that reducing antibody affinity (anti-TfR$^D$ relative to anti-TfR$^A$) and dose attenuates safety concerns related to reticulocyte loss. By 7 days post-dose, however, only the highest dose of anti-TfR$^D$/BACE1 had any measurable impact on reticulocyte levels, whereas all other doses tested showed a recovery of reticulocyte counts to levels similar to those of the IgG control mice. Notably, the absolute affinity of the antibody for TfR at 7 days post-dose was not as important as the persistence of the antibody in the bloodstream for the longer timepoints. Despite the much higher affinity of anti-TfR$^A$/BACE1 for TfR (Table A), mice treated with high-dose anti-TfR$^A$/BACE1 showed a recovery of reticulocyte numbers by 7 days that corresponded with the faster clearance of this antibody from circulation relative to anti-TfR$^D$/BACE1 (as seen in Example 1, FIG. 1B).

Since a dose response was observed in reticulocyte depletion, experiments were performed to determine whether it was possible to correlate various dose levels with an associated ability to reduce Abeta in brain. Briefly, wild type female C57B/6 mice ages 6-8 weeks were used for all studies. Mice were intravenously injected with 50 mg/kg of either control IgG, or anti-TfR/BACE1. Total injection volume did not exceed 250 μL and antibodies were diluted in D-PBS (Invitrogen) when necessary. After the indicated time, mice were perfused with D-PBS at a rate of 2 mL/min for 8 minutes. Brains were extracted and the cortex and hippocampus was isolated, homogenized in 1% NP-40 (Cal-Biochem) in PBS containing Complete Mini EDTA-free protease inhibitor cocktail tablets (Roche Doagnostics). Homogenized brain samples were rotated at 4° C. for 1 hour before spinning at 14,000 rpm for 20 minutes. The supernatant was isolated for brain antibody measurement. Whole blood was collected prior to perfusion in EDTA microtainer tubes (BD Diagnostics), allowed to site for 30 minutes at room temperature, and spun down at 5000×g for 10 minutes. The top layer of plasma was transferred to new tubes for antibody and mouse Abeta$_{1-40}$ measurements.

Total antibody concentrations in mouse plasma and brain samples were measurements using an anti-Fc/anti-huFc ELISA. NUNC 384 well Maxisorp immunoplates (Neptune, N.J.) were coated with F(ab')$_2$ fragment of donkey anti-human IgG, Fc fragment specific polyclonal antibody (Jackson ImmunoResearch, West Grove, Pa.) overnight at 4° C. Plates were blocked with PBS, 0.5% BSA for 1 hour at 25° C. Each antibody was used as a standard to quantify respective antibody concentrations. Plates were washed with PBS, 0.05% Tween-20 using a microplate washer (Bio-Tek Instruments Inc., Winooski, Vt.), standards and samples filuted in PBS containing 0.5% BSA, 0.35M NaCl, 0.25% CHAPS, 5 mM EDTA, 0.05% Tween-20 and 15 ppm Proclin were added for two hours at 25° C. Bound antibody was detected with horseradish peroxidase-conjugated F(ab')$_2$ goat anti-human IgG, Fc specific polyclonal antibody (Jackson ImmunoResearch), developed using 3,3',5,5'-tetramethyl benzidine (TMB) (KPL, Inc., Gaithersburg, Md.) and absorbance measured at 450 nm on a Multiskan Ascent reader (Thermo Scientific, Hudson, N.H.). Concentrations were determined from the standard curve using a four-parameter non-linear regression program. The assay had a lower limit of quantification (LLOQ) values of 3.12 ng/ml in serum and 12.81 ng/g in brain. Statistical analysis of differences between experimental groups was performed using two-tailed unpaired t-test.

Abeta$_{1-40}$ was also detected in brain and plasma. Briefly, mice were treated with antibody and perfused according to the method described above. For Abeta$_{1-40}$ measurements, hemi-brains were homogenized in 5 M guanidine hydrochloride buffer and samples rotated for 3 hours at room temperature prior to diluting (1:10) in 0.25% casein, 5 mM EDTA (pH 8.0) in PBS containing freshly added aprotinin (20 mg/mL) and leupeptin (10 mg/ml). Diluted homogenates were spun at 14,000 rpm for 20 min and supernatants were isolated for Abeta$_{1-40}$ measurement. Plasma was prepared as described above. The concentrations of total mouse Abeta$_{1-40}$ in plasma and brain were determined using a sandwich ELISA following similar procedures described above. Rabbit polyclonal antibody specific for the C-terminus of Abeta$_{1-40}$ (Millipore, Bedford, Mass.) was coated onto plates, and biotinylated anti-mouse Abeta monoclonal antibody M3.2 (Covance, Dedham, Mass.) was used for detection. The assay had LLOQ values of 1.96 pg/ml in plasma and 39.1 pg/g in brain. Statistical analysis of differences between experimental groups was performed using two-tailed unpaired t-test.

A robust and sustained reduction in brain Abeta at both 25 and 50 mg/kg dose levels for anti-TfR$^D$/BACE1 was observed (FIG. 2D), while anti-TfR$^A$/BACE1 showed a robust, but acute reduction in brain Abeta at all three dose levels (FIG. 2E). These data were consistent with the observed pharmacokinetics of the compounds in both the periphery and the brain (FIGS. 2F-2H). From these data, it was apparent that a dosage level of 25 mg/kg of anti-TfR$^D$/BACE1 is sufficient to significantly reduce brain Abeta levels in these studies.

Reticulocyte depletion by anti-TfR antibody species could be due to a variety of different natural processes, including effector function/antibody-dependent cell-mediated cytotoxicity (ADCC), complement-dependent cytotoxicity (CDC), direct target-mediated lysis/apoptosis, and/or phagocytosis of opsonized reticulocytes by macrophages. A series of experiments was undertaken to better understand the mechanisms responsible for the observed reticulocyte depletion following anti-TfR antibody administration.

Example 2B. Impact of Modulating Effector Function

In addition to differing in affinity and valency for TfR, the monospecific and bispecific anti-TfR antibodies used the preceding experiments also differed in the degree of their effector functions. The monospecific anti-TfR antibodies were produced in CHO cells, and had mammalian-type glycosylation and wild-type effector function. The bispecific anti-TfR/BACE1 antibodies had a severely reduced or eliminated capacity to interact with Fcγ-receptors using one or more of the following methods well-known in the art: abrogating glycosylation due to the presence of the mutation N297G or N297A in the Fc region (Atwal et al., Sci. Transl. Med. 3, 84ra43 (2011); Fares Al-Ejeh et al., Clin. Cancer Res. (2007) 13:5519s-5527s), modifying the antibody Fc region to contain an aspartic acid to alanine mutation at position 265 (D265A) known to completely abrogate effector function (see, e.g., U.S. Pat. No. 7,332,581), or producing the antibody in a manner that prevented wild-type mammalian glycosylation, such as by producing it in E. coli.

Figure 3A:
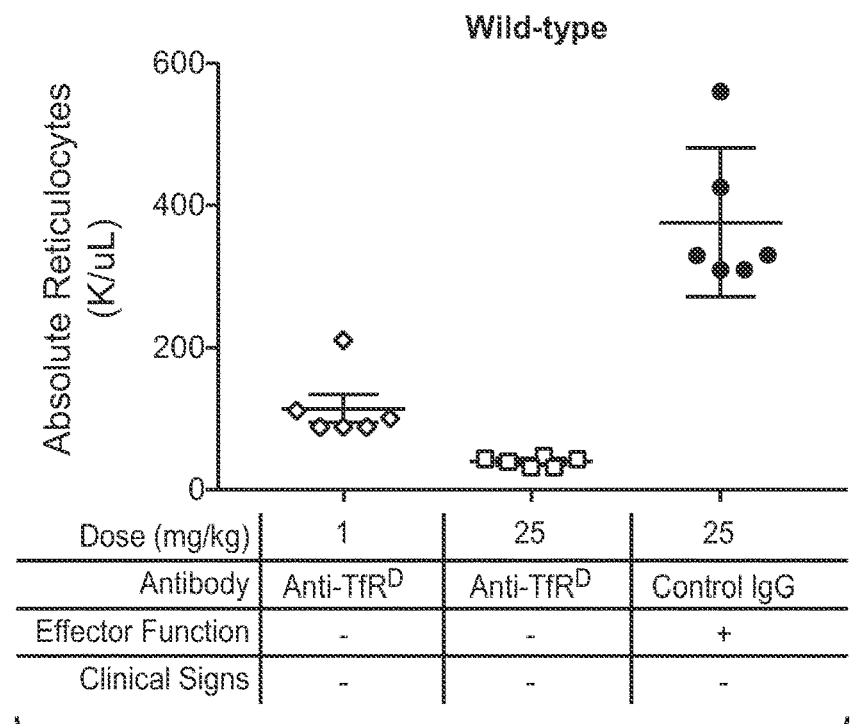
FIGS. 3A-3E depict the results of experiments assessing the impact of elimination of effector function (FIGS. 3A-3C) or elimination of complement function (FIGS. 3D and 3E) on reticulocyte depletion by various anti-TfR antibodies, as described in Example 2B. Total reticulocyte counts in whole blood are shown from wild-type mice (FIGS. 3A and 3C), Fcγ$^{-/-}$ (B6.129P2-Fcer1gtm1Rav N12) mice (FIG. 3B), or C3$^{-/-}$ mice (FIG. 3D) 24 hours after intravenous injection of antibody at the indicated dose, as compared to control IgG (n=6 per group).

The mouse studies performed in Example 2A were repeated with these Fc-modified antibodies and also in different mouse strains lacking either Fcγ receptors or complement C3, to evaluate potential mechanisms of reticulocyte depletion including effector-driven ADCC or CDC respectively; whole blood samples were assessed for total reticulocyte counts 24 hours after intravenous injection of the antibody. In a first experiment, administration of monospecific 1 mg/kg or 25 mg/kg anti-TfR$^D$ lacking effector function to wild-type mice had the same depletive effect on reticulocyte counts as an anti-TfR$^D$ antibody with full effector function (compare FIG. 3A with FIG. 2B). However, acute clinical signs were not observed in mice treated with the effectorless anti-TfR$^D$ antibody, in sharp contrast to those treated with an effector-positive anti-TfR$^D$ antibody (Example 2A). Similarly, when effector-positive anti-TfR$^D$ was administered to mice lacking Fcγ receptor (to eliminate ADCC mechanisms that may be triggered by effector function), reticulocyte levels were reduced to near zero following a dose of 25 mg/kg, but no acute clinical signs were observed (FIG. 3B).

Figure 3B:
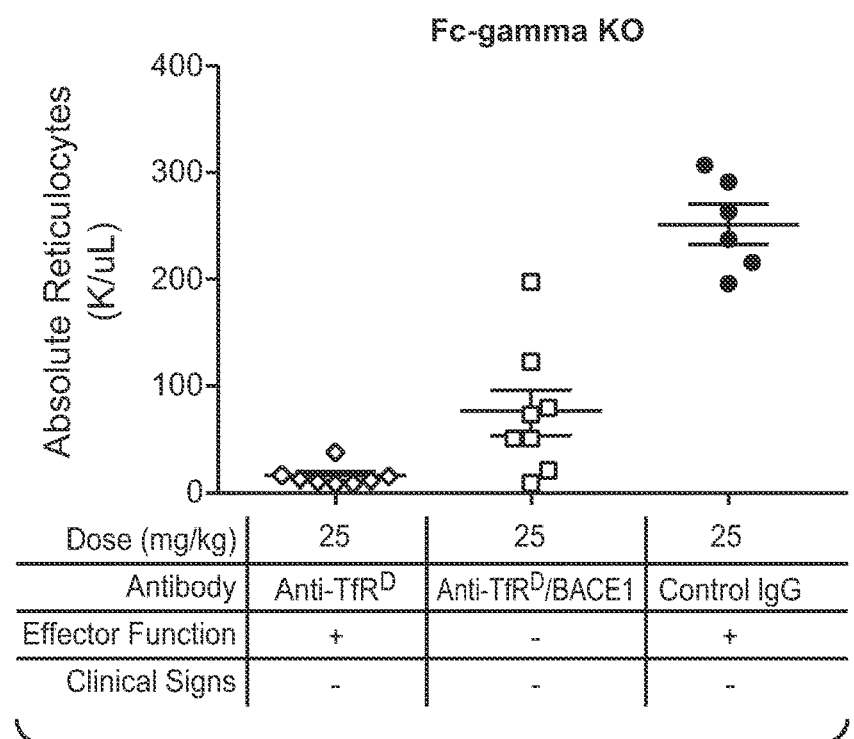

The impact of the bispecific anti-TfR$^D$/BACE1 D265A antibodies lacking effector function on reticulocyte levels was also assessed in the Fcγ knockout mice (FIG. 3B). Even the full abrogation of antibody effector function and the absence of the Fcγ receptor in the mice did not mitigate reticulocyte depletion when administered at a dose level of 25 mg/kg. Consistent with other experiments using bispecific anti-TfR/BACE1 effectorless antibodies in wild-type mice, adverse clinical signs were not observed in treated Fcγ knockout mice.

Figure 3C:
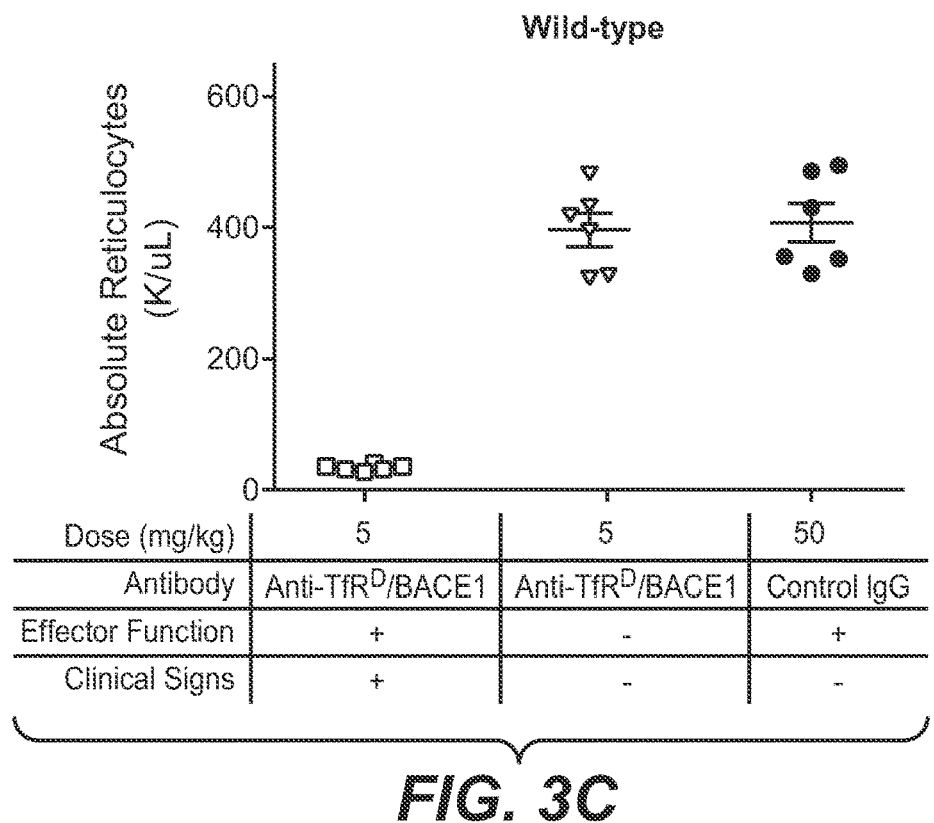

To determine whether the presence of effector function is sufficient to drive acute clinical symptoms, and to further characterize the contribution of effector function to reticulocyte depletion, the experiments were repeated in wild-type mice comparing a low dose (5 mg/kg) of effectorless anti-TfR$^D$/BACE1 D265A with an equivalent dose of full effector-positive anti-TfR$^D$/BACE1 (FIG. 3C). Acute clinical signs were observed upon introduction of effector function into the bispecific antibody. Furthermore, robust reticulocyte depletion was observed with the effector-positive antibodies at a lower dose level relative to the effectorless version of the antibody (FIGS. 3C and 2C). From this combined data, effector function is not necessary to drive reticulocyte depletion, but clearly contributes to this depletion, particularly at lower dose levels. Importantly, the acute clinical symptoms observed in mice are linked to the effector status of the antibody, such that effectorless antibodies or Fcγ-knockout mice both completely mitigate these symptoms.

Figure 3D:
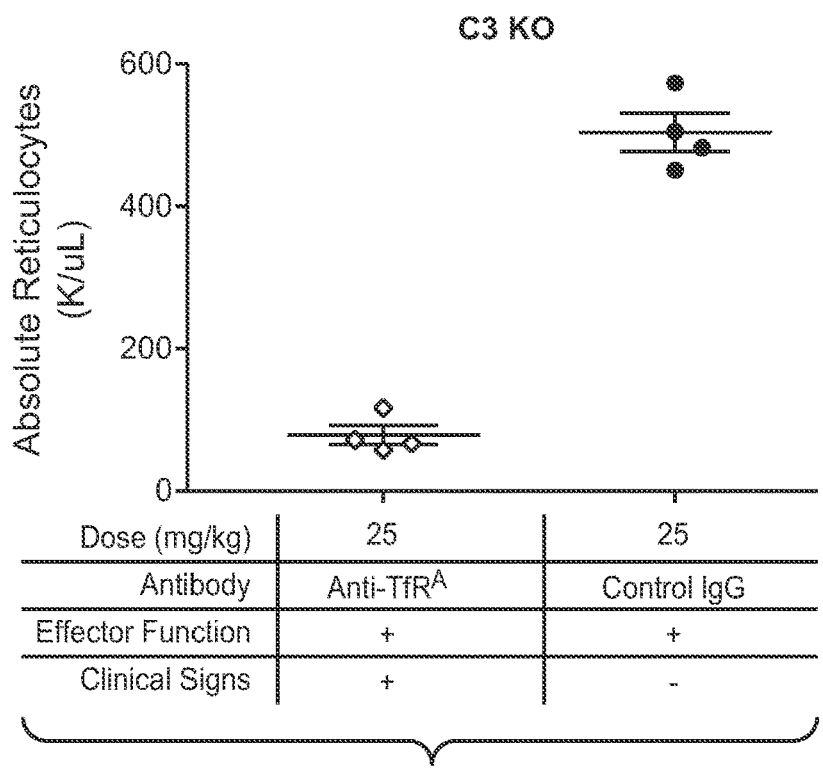
Figure 3E:
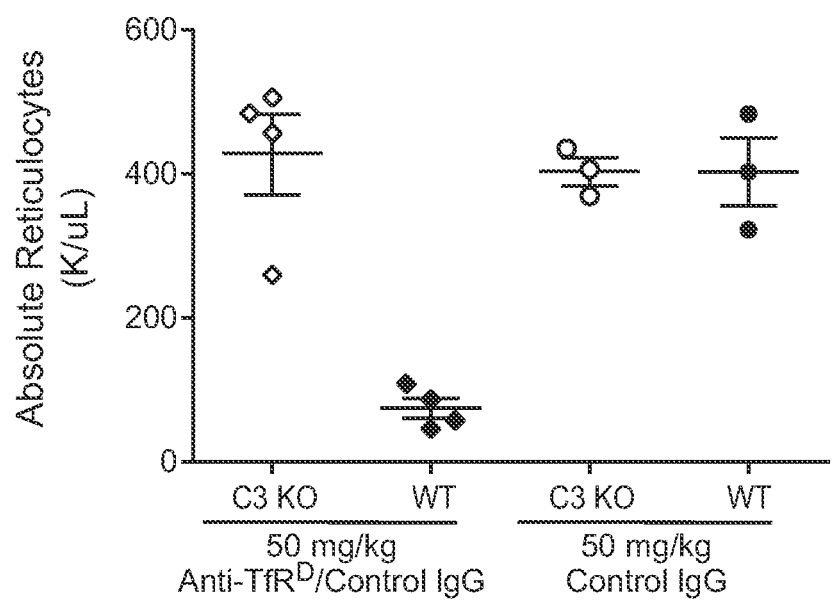

To determine whether the complement cascade was involved in either the clinical symptoms or the loss of reticulocytes, the experiments were performed again in mice deficient in complement C3 (ie, mice lacking the normal complement cascade). As shown in FIG. 3D, effector-positive anti-TfR$^A$ caused both profound reticulocyte depletion and robust acute clinical symptoms in these mice, indicating that complement C3 and the associated complement cascade do not play a major role in driving either of the observed effects when the administered antibody possesses full effector function. To test whether the same result would be obtained in the absence of full effector function, C3 knockout mice were dosed with effectorless anti-TfRD/BACE1 antibodies to determine if complement mediates the residual reticulocyte depletion. The results are shown in FIG. 3E. Indeed, residual reticulocyte depletion is rescued when both effector function and the complement cascade are eliminated by dosing C3 knockout mice with effectorless anti-TfR bispecific antibodies at high therapeutic dose levels (50 mg/kg). Thus, complement appears to act as a mechanism of reticulocyte depletion following administration of effectorless anti-TfR antibodies in mice.

An in vitro complement-dependent cytotoxicity (CDC) assay was also performed. Briefly, CDC assays were performed using primary mouse bone marrow cells or mouse erythroleukemic lymphoblasts (HPA Cultures, UK) as target cells and complement derived from rabbit serum (EMD Chemicals, Gibbstown N.J.). Cells were counted and viability determined by Vi-Cell™ (Beckman Coulter, Fullerton, Calif.). Anti-TfR$^A$/BACE1, anti-TfR$^A$ or negative or positive control antibody (IgG or anti-H2 Kb, respectively) were serially diluted 1:4 in assay medium (RPMI-1640 medium supplemented with 20 mM HEPES, pH 7.2 and 1% FBS), and distributed into a white, flat-bottom 96-well tissue culture plate (Costar; Corning, Acton Mass.). Following the addition of serum complement diluted 1:3 in assay medium and the target cells ($2 \times 10^5$ cells/well), the plate was incubated with 5% $CO_2$ for 2 hours at 37° C. The plates were then left at room temperature for 10 minutes with constant shaking. The extent of cell lysis was quantified by measuring luminescence intensity with a SpectroMax™ M5 plate reader. Luminescence values of sample dilutions were plotted against the antibody concentration, and the dose-response curves were fitted to a four-parameter model using GraphPad™ (GraphPad Software Inc.).

Figure 4A:
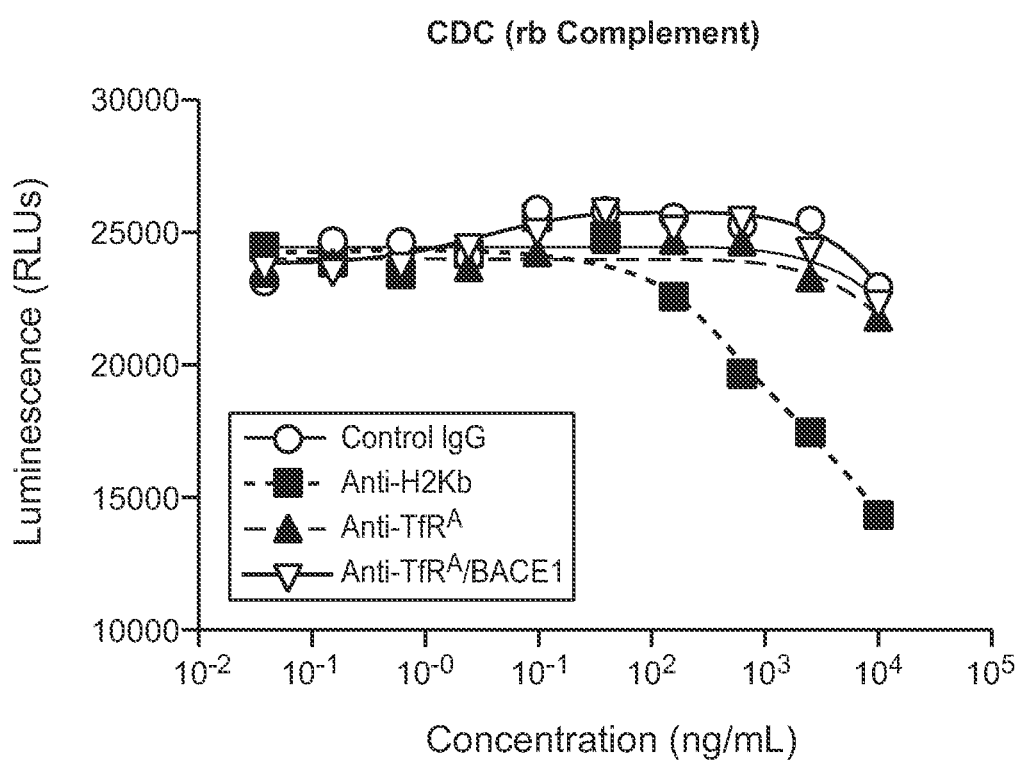
FIGS. 4A and 4B depict the results of in vitro experiments assessing the induction of antibody-dependent cell-mediated cytotoxicity (ADCC) (FIG. 4A) or complement-dependent cytotoxicity (CDC) (FIG. 4B) by anti-TfR$^A$, anti-TfR$^A$/BACE1, or control IgG in mouse erythroleukemic blasts at a range of antibody concentrations, as described in Example 2B.

Interestingly, neither monospecific effector-function-competent anti-TfR$^A$ nor effectorless bispecific anti-TfR$^A$/BACE1 treatment of mouse cells in the presence of serum complement resulted in complement-mediated lysis of the cells, while the anti-H2 Kb positive control showed significant cell lysis (FIG. 4A). Notably, the differing effector activity of the antibodies did not appear to influence their ability to elicit CDC activity. One nonlimiting explanation is that complement may mediate reticulocyte depletion in vivo via opsonization of circulating reticulocytes by splenic and liver macrophages (Garratty (2008), Transfusion Med. 18(6): 321-334; Mantovani et al, (1972) J. Exp. Med. 135: 780-792; Molina et al., (2002) Blood 100 (13): 4544-4549), a mechanism that must be intact with anti-TfR F(ab')2 fragments.

Similar in vitro experiments were also undertaken to confirm the previously-described in vivo results supporting a link between effector function-mediated antibody-dependent cell-mediated cytotoxicity (ADCC), acute clinical symptoms, and reticulocyte depletion. ADCC assays were carried out using freshly isolated PBMCs from healthy donors as effector cells, and primary mouse bone marrow cells or mouse erythroleukemic lymphoblasts (HPA Cultures, UK) as target cells. To minimize donor variations derived from allotypic differences at residue 158 position of FcγRIIIA, blood donors were limited to those carrying the heterozygous FcγRIIIA genotype (F/V158). Briefly, PBMCs were isolated by density gradient centrifugation using a Uni-Sep blood separation tube (Accurate Chemical & Scientific; Westbury, N.Y.). Target cells were prelabled with 1.4 mM solution of calcein AM (Molecule Probes) and were seeded in a 96-well, round-bottom plate (BD Biosciences; Mississauga, Ontario; Canada) at $4 \times 10^4$/well. Serial dilutions of anti-TfR/BACE1, anti-TfR and control antibody were added to the plates containing the target cells, followed by incubation at 37° C. with 5% carbon dioxide for 30 minutes to allow opsonization. The final concentrations of antibodies ranged from 1,000 to 0.004 ng/mL following 4-fold serial dilutions. After the incubation, $1 \times 10^6$ PBMC effector cells in 100 μL assay medium were added to each well to give a ratio of 25:1 effector to target cells, and the plates were incubated for an additional 3 hours. The plates were centrifuged at the end of incubation, and fluorescent signals in supernatants were measured using a SpectraMax™ M5 microplate reader, with excitation at 485 nm and emission at 520 nm. Signals of wells containing only the target cells represented spontaneous release of the calcein AM from labeled cells (spontaneous release), whereas wells containing target cells lysed with Triton™ X-100 provided the maximum signal available (maximum lysis). Antibody-independent cellular cytotoxicity (AICC) was measured in wells containing target and effector cells without the addition of antibody. The extent of specific ADCC was calculated as follows:

$$\% \text{ ADCC} = 100 \times (\text{Sample signal} - \text{AICC}) \div (\text{maximum lysis} - \text{spontaneous release})$$

The ADCC values of sample dilutions were plotted against the antibody concentration and the dose response curve fitted with a four-parameter model using GraphPad™ (GraphPad Software Inc.).

Figure 4B:
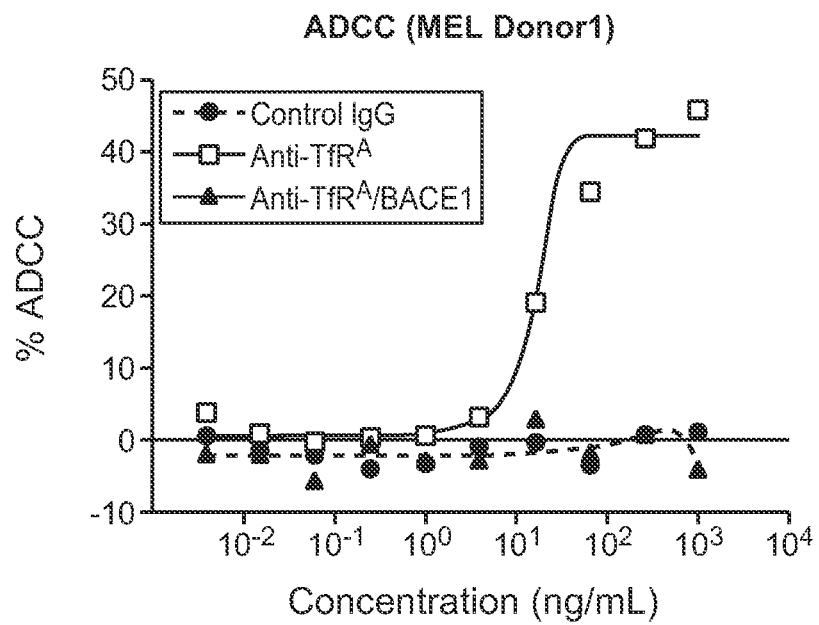

The anti-TfR$^A$ used in this assay had effector function, while the anti-TfR$^A$/BACE1 used in the assay had no effector function. As shown in FIG. 4B, the antibody with effector function induced ADCC while the anti-TfR$^A$/BACE1 antibody lacking effector function did not, correlating with the prior mouse experiment results. These data further support the idea that acute clinical signs in treated mice are due to ADCC actively elicited by the effector-positive antibodies binding circulating reticulocytes, and that effector-driven ADCC can also contribute to reticulocyte depletion following antibody administration (FIG. 3C).

Example 2C: Impact of Modulating Fc or BACE1 Binding

Figure 5A:
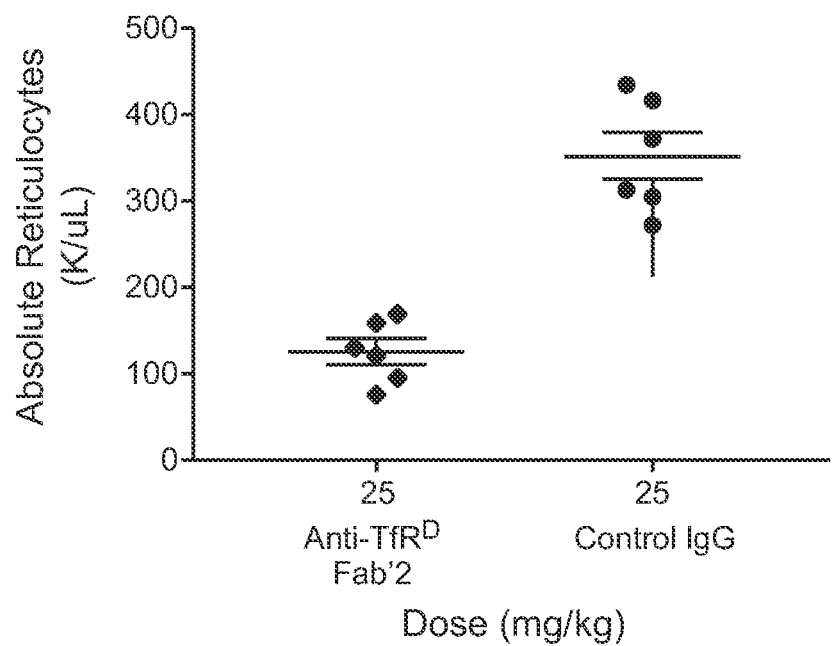
FIGS. 5A-5C depict the results of experiments assessing whether elimination of Fc binding or BACE1 binding impacts reticulocyte depletion by monospecific or bispecific anti-TfR antibodies, as described in Example 2C. Total reticulocyte counts are shown for wild-type mice (n=6 per group) 24 hours after intravenous injection of the indicated F(ab')2 or control IgG (FIGS. 5A and 5B) or bispecific antibody (FIG. 5C).
Figure 5B:
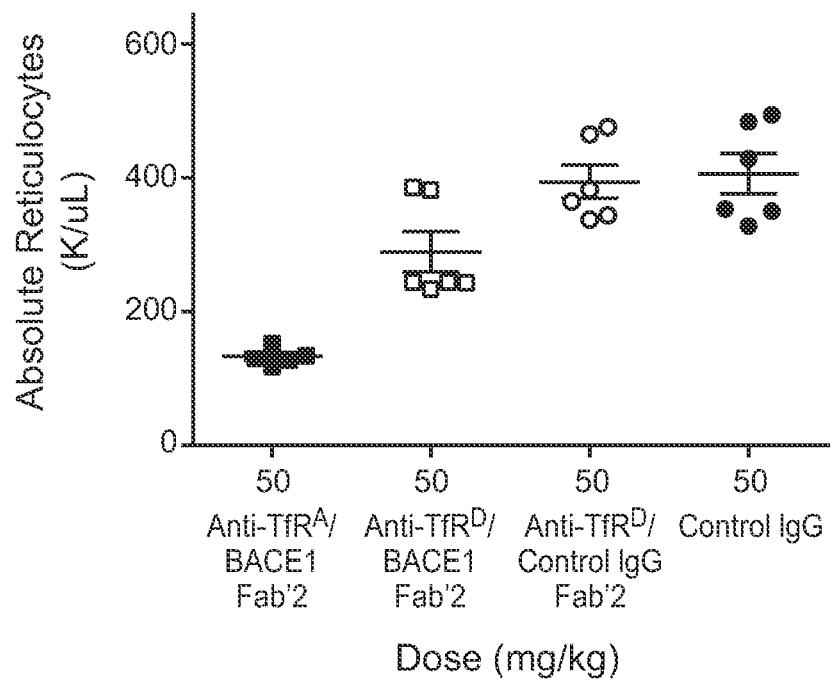
Figure 5C:
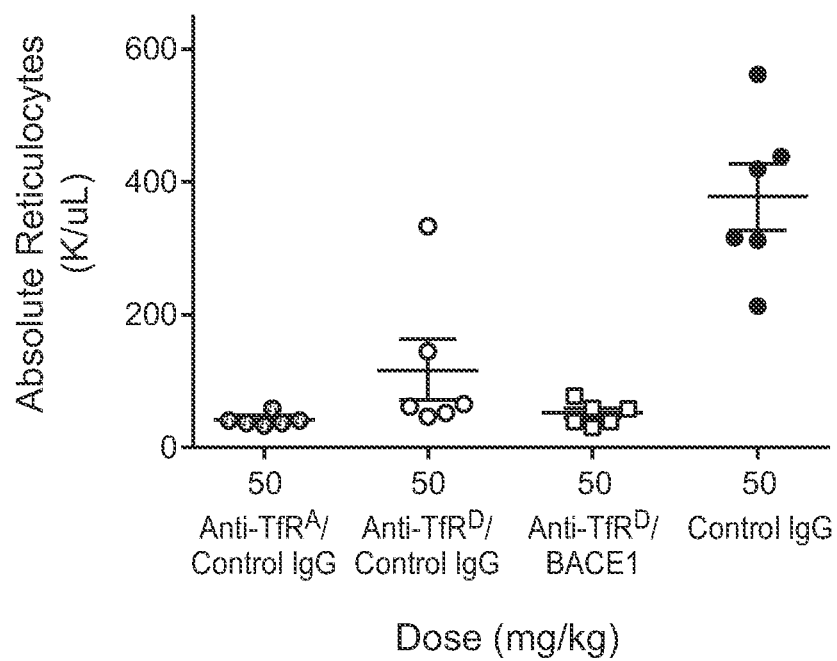

The role of the Fc arm and the BACE1 arm were each separately examined for their potential involvement in mediating reticulocyte depletion. Monospecific and bispecific anti-TfR with wild-type IgG1 Fc regions having full effector function and normal glycosylation were generated. Briefly, TfR (hole) and IgG (knob) half antibodies were expressed separately in CHO and annealed in vitro as described (Carter, P. (2001) J. Immunol. Methods 248, 7-15; Ridgway, J. B., Presta, L. G., and Carter, P. (1996) Protein Eng. 9, 617-621; Merchant, A. M., Zhu, Z., Yuan, J. Q., Goddard, A., Adams, C. W., Presta, L. G., and Carter, P. (1998) Nat. Biotechnol. 16, 677-681; Atwell, S., Ridgway, J. B., Wells, J. A., and Carter, P. (1997) J. Mol. Biol. 270, 26-35). F(ab')2 fragments were generated from anti-TfR IgG, anti-TfR/IgG or anti-TfR/BACE1 antibodies by digestion with immobilized pepsin. The antibody was reconstituted in 100 mM sodium acetate, pH 4.2 and incubated with immobilized pepsin resin (0.3 mL settled gel/mg IgG) overnight at 37° C. with rotation. After incubation, the sample was centrifuged to separate the immobilized pepsin from the F(ab)$_2$-digested mixture. The F(ab')$_2$ fragment was then purified using an SP sepharose, strong cation-exchange resin (1 mL HiTrap™ column (Supelco)). The sample was loaded in 50 mM NaOAc pH 5.0 and eluted with a 0-0.5 M NaCl gradient over 20 column volumes after which the sample was dialyzed against PBS, pH 7.4. Mouse experiments were performed with these antibodies and F(ab')$_2$ using the same procedures as above and an intravenous 25 mg/kg dose of monospecific F(ab')$_2$ or an intravenous 50 mg/kg dose of bispecific or control F(ab')2 or antibody; whole blood samples were assessed for total reticulocyte counts 24 hours after intravenous injection of the antibody/F(ab')2. The results are shown in FIGS. 5A-5C.

Administration of the anti-TfR$^D$ F(ab')2 had a very similar reticulocyte depleting effect to administration of anti-TfR$^D$ antibody (compare FIG. 5A to FIGS. 3A and 3B), indicating that the Fc portion of the antibody is not necessary for the observed reticulocyte depletion at the dose levels evaluated. Although bispecific F(ab')2 molecules showed a slight attenuation of reticulocyte depletion relative to full-length bispecific IgG antibodies (compare FIG. 5B to FIG. 2C), it should be noted that this is most likely due to the general faster clearance of F(ab')$_2$ relative to IgG (Covell et al., (1986) Cancer Res. 46:3969-3978), leading to overall reduced antibody exposure over the 24 hour post-dose interval. Nonetheless, the reticulocyte depletion observed following administration of bispecific F(ab')2 antibodies further underscores the conclusion that the Fc region is not necessary for reticulocyte depletion to occur. Bispecific antibodies lacking the BACE1 arm (anti-TfR$^D$/control IgG) depleted reticulocytes to the same degree as anti-TfR$^D$/BACE1 (FIG. 5C), demonstrating that the BACE1 arm also does not contribute to reticulocyte elimination.

Example 3: Further Engineering Binding Affinity

Figure 6A:
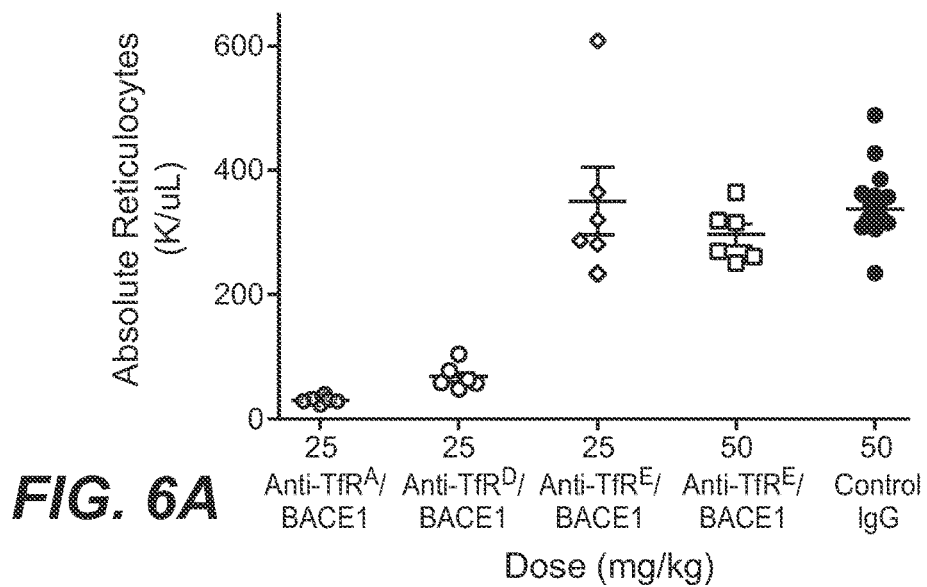
FIGS. 6A-6C depict the results of experiments assessing the impact of reducing affinity to TfR on reticulocyte depletion and brain TfR expression, as described in Example 3.

Certain of the above results suggested that there was an affinity and dose component to the observed degree of reticulocyte depletion (FIG. 2C). To better understand how affinity and dose impact reticulocyte depletion, the mouse dosing experiments performed in Example 2 were repeated with additional lower-affinity anti-TfR antibodies, specifically anti-TfR$^E$/BACE1 at two different dose levels (25 mg/kg and 50 mg/kg). Anti-TfR$^E$ at either of the tested doses had essentially no impact on reticulocytes (FIG. 6A), while similar doses of anti-TfR$^A$/BACE1 or anti-TfR$^D$/BACE1 depleted reticulocytes. From the results discussed in Example 1 it had been observed that anti-TfR$^E$/BACE1 had better sustained plasma exposure and persistence in the brain, but less robust transport across the blood-brain barrier than anti-TfR$^D$/BACE1. Given that the anti-TfR$^D$/BACE1 administration resulted in reticulocyte depletion but anti-TfR$^E$/BACE1 administration did not, variant anti-TfRs with affinities between that of anti-TfR$^D$ and anti-TfR$^E$ for TfR were generated to see if the safety profile of the antibody could be improved without sacrificing BBB transport and persistence in brain.

Figure 6B:
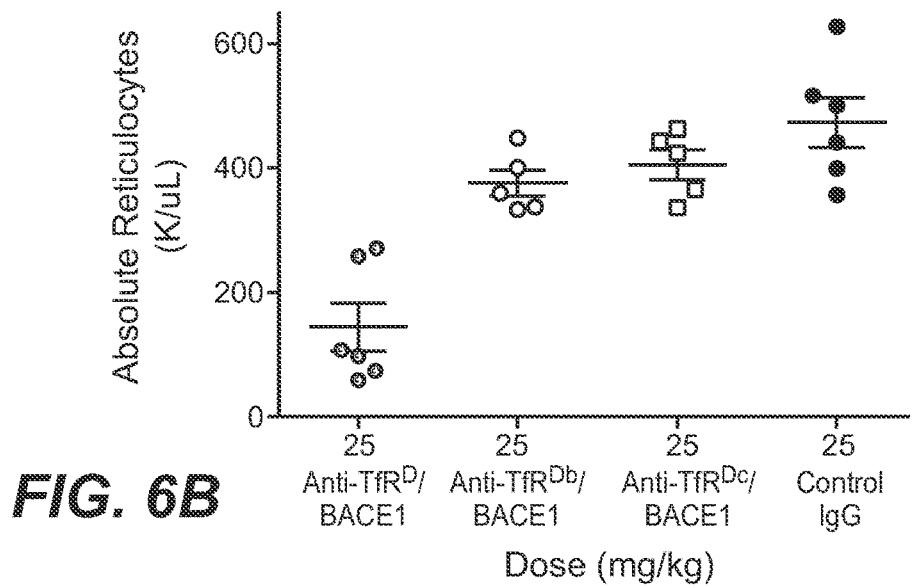

Briefly, site-directed mutagenesis was employed to combine the two point mutations representing the anti-TfR$^D$ and anti-TfR$^B$ variants respectively into a single antibody designated anti-TfR$^{Db}$ using standard mutagenesis techniques. Similarly, the two point mutations representing the anti-TfR$^D$ and anti-TfR$^c$ variants respectively into a single antibody designated anti-TfR$^{Dc}$. Both antibodies were made into a bispecific format with anti-BACE1 using knob and hole technology as described in Example 2C. The affinities of both antibodies were between those of the anti-TfR$^D$ and anti-TfR$^E$ antibodies for TfR, and anti-TfR$^{Db}$/BACE1 antibody had approximately three-fold greater affinity for TfR than did the anti-TfR$^{Dc}$/BACE1 antibody. The mouse administration/reticulocyte depletion experiment was repeated with these new variants, and the results are shown in FIG. 6B. Both variants demonstrated markedly improved (ie, less) reticulocyte depletion than that observed with the anti-TfR$^D$/BACE1 antibody at the same dose level, and reticulocyte levels approximated those of control-treated mice at 24 hours post-dose. As expected, the plasma antibody concentration of both new variant antibodies over time, the brain antibody concentration (both the maximum value and the decrease over time), and the reduction in Aβ$_{1-40}$ was between that of anti-TfR$^D$/BACE1 and anti-TfR$^E$/BACE1 when administered at the same dose level.

Figure 6C:
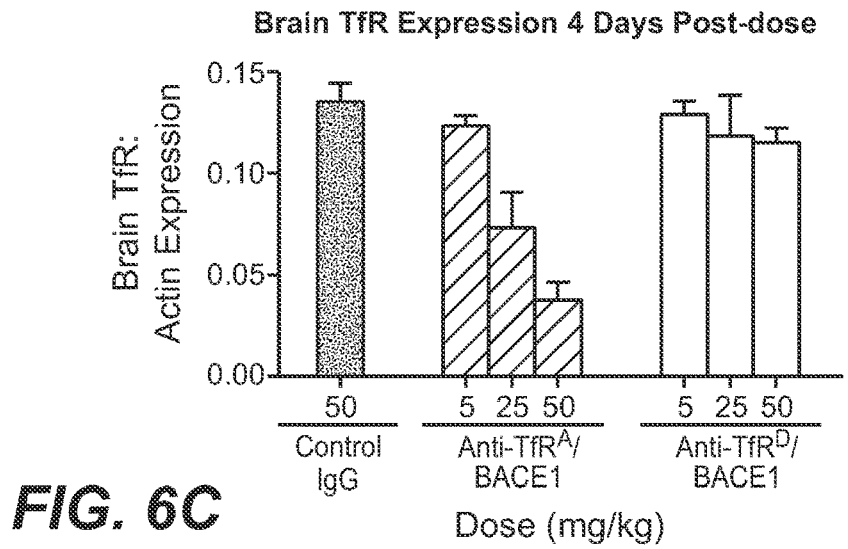

The impact of affinity and dose on expression of TfR at the blood-brain barrier was also examined. Mice were treated with a single dose of anti-TfR$^A$/BACE1 or anti-TfR$^D$/BACE1 at 5, 25 or 50 mg/kg, and TfR expression in brain was evaluated at 4 days post-dose via Western blot. Brains from antibody-treated mice were PBS perfused before extraction, and isolated cortex and hippocampus were homogenized in 1% NP-40 (Calbiochem) in PBS containing Complete Mini EDTA-free protease inhibitor tables (Roche Diagnostics). Homogenized brains were rotated at 4° C. for 1 hour before spinning at 14,000 rpm for 20 minutes. Supernatant was isolated and equal concentrations of protein were separated by 4-12% Novex Bis-Tris gels (Invitrogen). Membranes were incubated with anti-TfR (Invitrogen) and anti-actin (Abcam) antibodies overnight at 4° C. followed by IRDye® (Li-Cor Biosciences) secondary antibodies at room temperature for 2 hours. Immunoblots were imaged and bands were quantified by densitometry using Odyssey Infrared Imaging System™ software (Li-Cor Biosciences, Lincoln, Nebr.). Four days post-dose, TfR expression in all three of the anti-TfR$^D$/BACE1 treated samples was similar, although slightly depressed from control levels at higher dose levels (FIG. 6C). In contrast, increasing doses of anti-TfR$^A$/BACE1 antibody resulted in a marked decrease in expression of TfR at the blood-brain barrier 4 days post-dose. Thus, reducing the affinity of the anti-TfR antibody also improves the observed dose-dependent reduction in brain TfR expression, potentially further contributing to improvement in the overall safety profile of the antibody.

Example 4: Assessment of BBB Permeability

A concern of exploiting a blood-brain barrier transport receptor for transport of heterologous molecules into the brain is that the BBB itself might be impaired. Accordingly, the permeability of the BBB to antibodies upon dosing with anti-TfR was investigated. Wild-type mice were intravenously administered 50 mg/kg of control IgG, or 25 mg/kg of each of the indicated co-injected antibody combinations. Mean antibody uptake in brain 24 hours after intravenous injection was assessed using a generic human-Fc ELISA according to Example 1 or using an anti-BACE1 specific ELISA following similar procedures to those described in Example 1. The BACE1 extracellular domain was used as the coat protein and detection was performed with horseradish peroxidase-conjugated F(ab')2 goat anti-human IgG, Fc-specific polyclonal antibody. This assay had LLOQ values of approximately 2.56 ng/g for anti-BACE1 and 12.8 ng/g for anti-TfR$^D$/BACE1. Brain A$\beta_{1-40}$ levels were measured after administration using the same procedure set forth in Example 1.

Figure 7A:
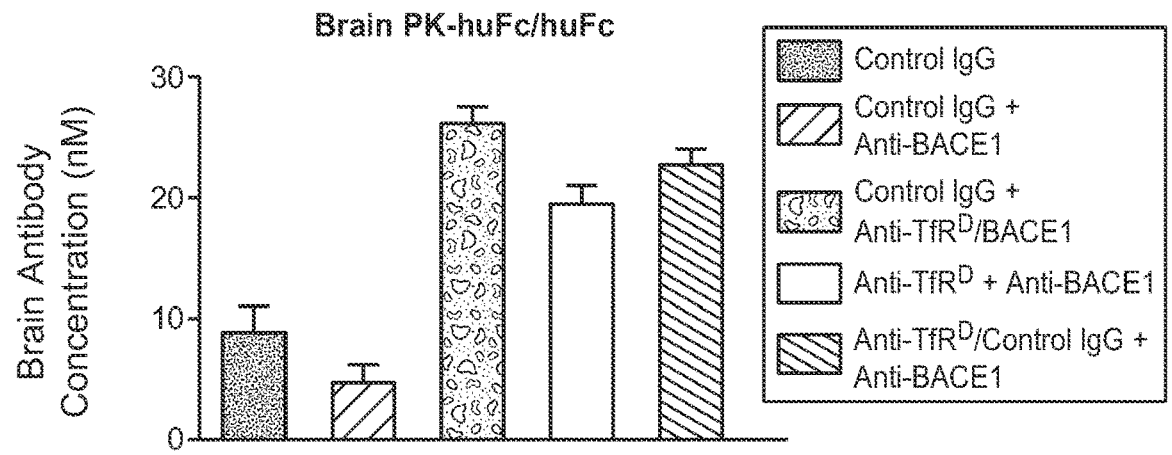
FIGS. 7A-7C depict the results of experiments assessing whether TfR antibody treatment affected blood-brain barrier permeability, as described in Example 4. Wild-type mice were intravenously administered 50 mg/kg of control IgG or 25 mg/kg of each of the co-injected antibody combinations. Mean antibody uptake in brain 24 hours after intravenous injection was measured using a generic human-Fc ELISA (FIG. 7A) or a BACE1-ectodomain ELISA (FIG. 7B).
Figure 7B:
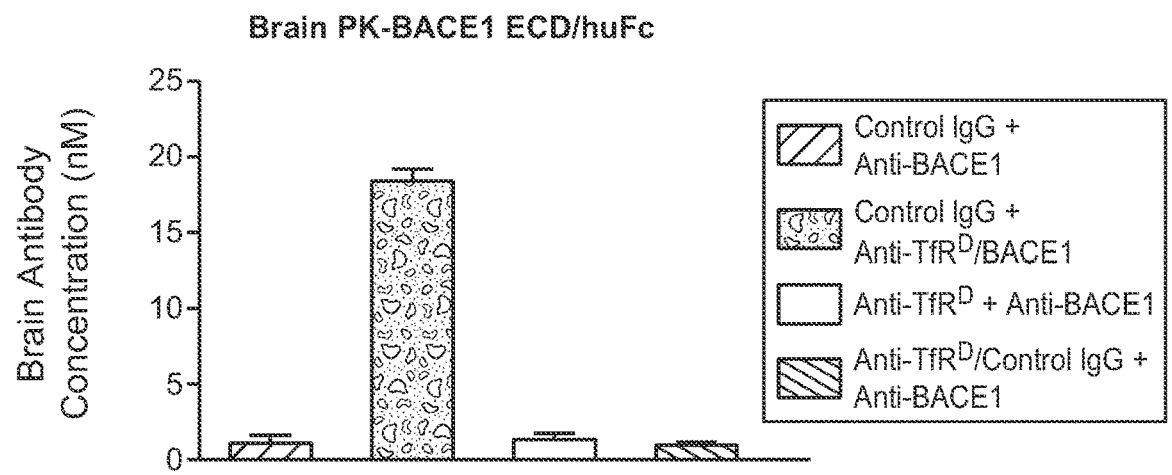
Figure 7C:
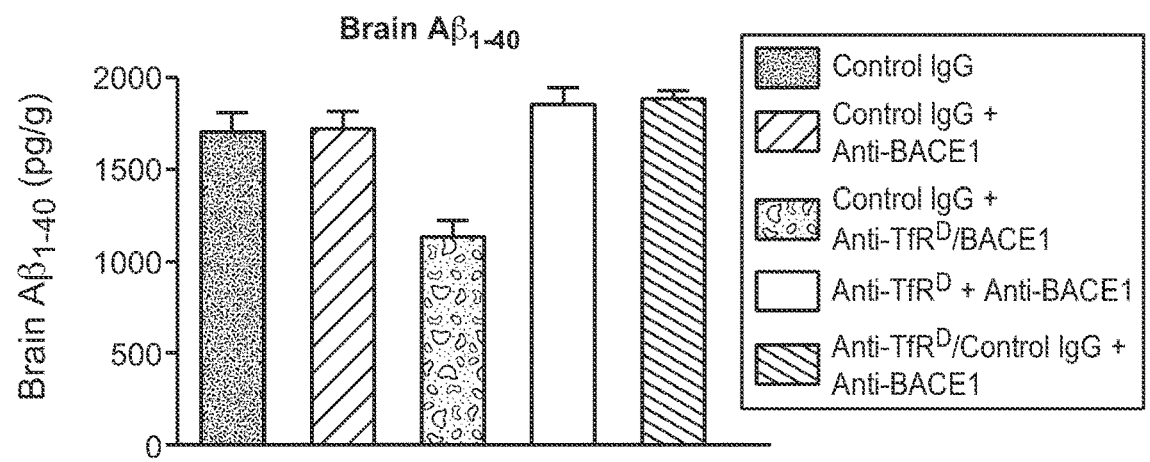

The results are shown in FIGS. 7A-7C. Brain antibody exposure was highest in the control IgG+anti-TfR$^D$/BACE1-treated mice, but also substantial in the mice treated with anti-TfR$^D$-containing antibody combinations (FIG. 7A). This correlates with the results in Example 1 in that the lower-affinity bispecific form of anti-TfR$^D$ is taken up and persists in the brain longer than the higher-affinity monospecific form of anti-TfR$^D$. Antibodies coadministered with the anti-TfR antibody were not taken up into the brain in substantial quantities; the only anti-BACE1 observed in substantial quantity in the brain was that directly conjugated to anti-TfR$^D$ (FIG. 7B). Similarly, the only anti-BACE1 activity observed in the brain was in the anti-TfR$^D$/BACE1-treated mice (FIG. 7C). Taken together, these data indicate that the blood-brain barrier permeability to antibodies was not affected by anti-TfR treatment.

Example 5: Impact of Multiple Dosing on Reticulocyte Levels

The foregoing studies focused on a single dose of anti-TfR antibody and the resulting impact on reticulocyte levels and concomitant acute clinical symptoms. To ascertain whether different effects were observed following multiple doses over a longer time period, further studies were undertaken. The same protocols as described in the preceding examples were used, with the exception that instead of a single intravenous dose, mice were dosed intravenously once per week with 25 mg/kg anti-TfR$^D$/BACE1 or an IgG control, for a total of four weeks. Tissue/blood was collected at 1, 4 or 7 days post the second injection and post the fourth injection, and processed using the above-described protocols. In addition, direct bilirubin, serum iron, and total and unsaturated iron binding capacity were determined for serum samples by colorimetric assays using the Integra™ 400 (Roche, Indianapolis, Ind.) according to the manufacturer's instructions. Six mice were used for each time point and treatment group.

Figure 8B:
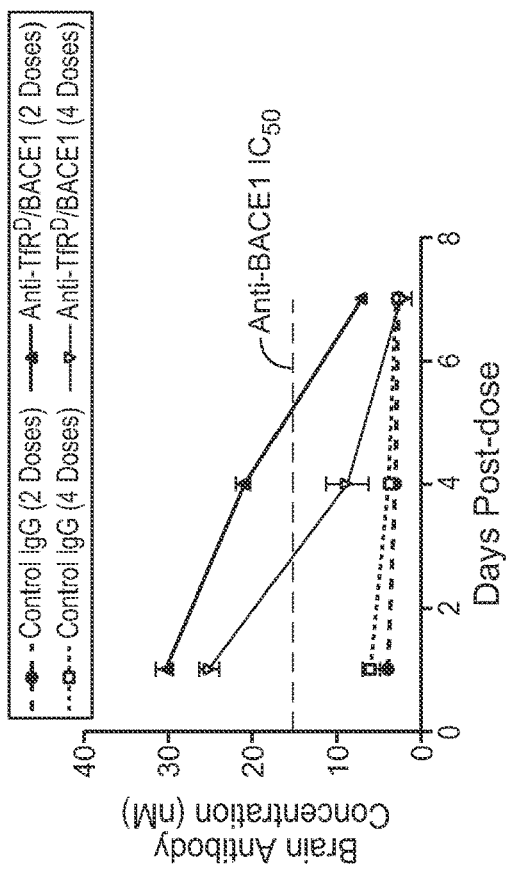
FIGS. 8A-8F depict the results of experiments assessing the impact of multiple doses of anti-TfR$^D$/BACE1 on reticulocyte levels in treated mice, as described in Example 5. Wild-type mice were intravenously dosed once weekly with 25 mg/kg of control IgG or anti-TfR$^D$/BACE1.
Figure 8D:
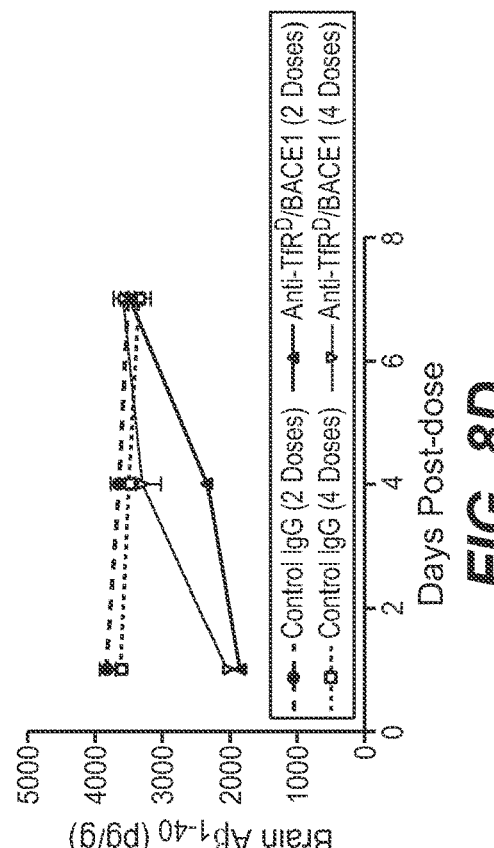
Figure 8A:
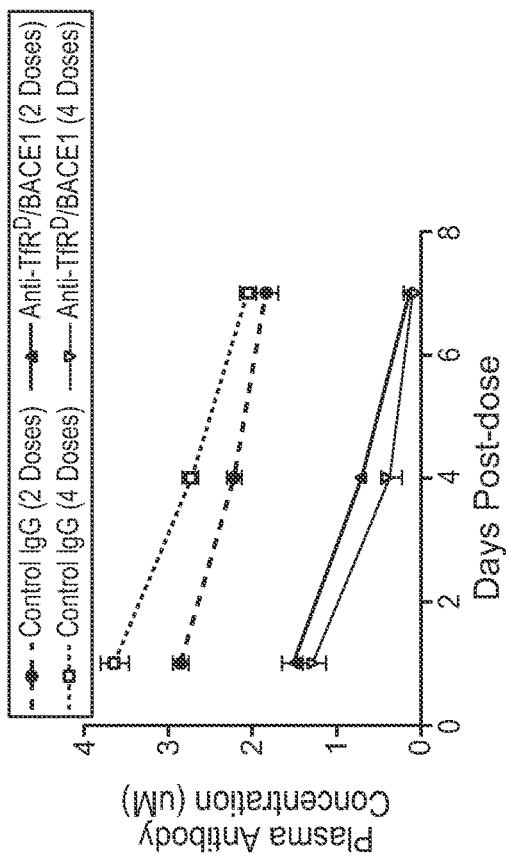
Figure 8C:
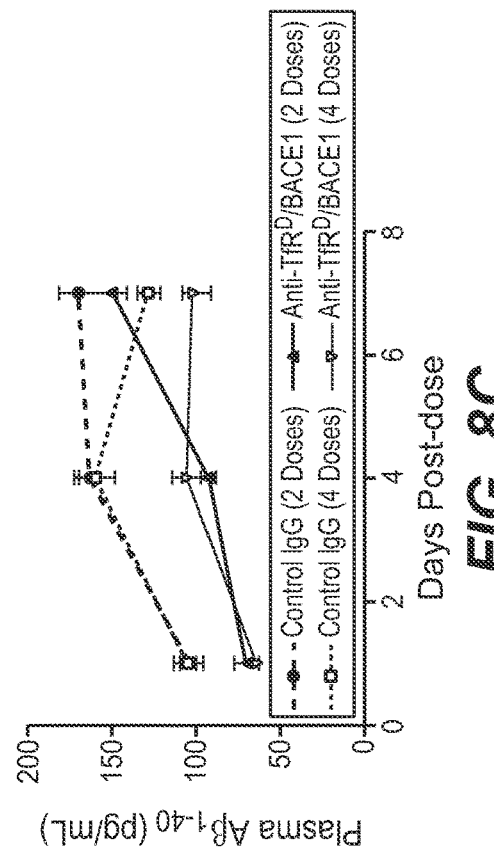

The serum antibody concentration for anti-TfR$^D$/BACE1 was similar over time after 2 or 4 doses, suggesting that clearance in the mouse bloodstream does not substantially differ after repeated dosing (FIG. 8A). However, a slight decrease in overall antibody exposure was apparent 4 days after the fourth dose relative to the same time after the second dose, suggestive of the occurrence of mouse anti-drug antibodies (ADAs) to the administered human IgG antibodies. Similar to the serum antibody concentrations, brain antibody concentrations were decreased by 4 days after the fourth dose, although the persistence of the antibodies present in the brain over time mirrored that observed after the second dose (FIG. 8B). Plasma (FIG. 8C) and brain (FIG. 8D) levels of Abeta1-40 correlated well with the observed amounts of anti-TfR$^D$/BACE1 present in the serum and brain after 2 or 4 doses.

Figure 8E:
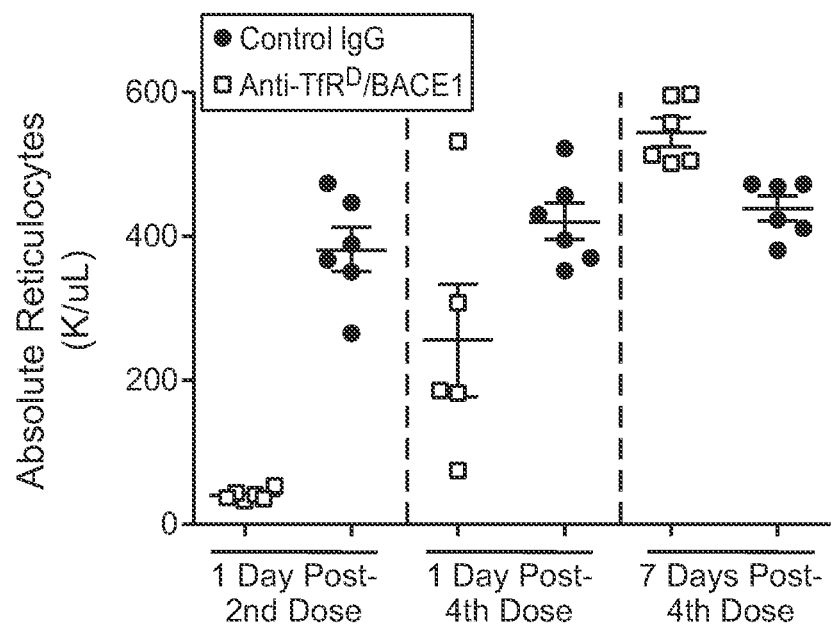
Figure 8F:
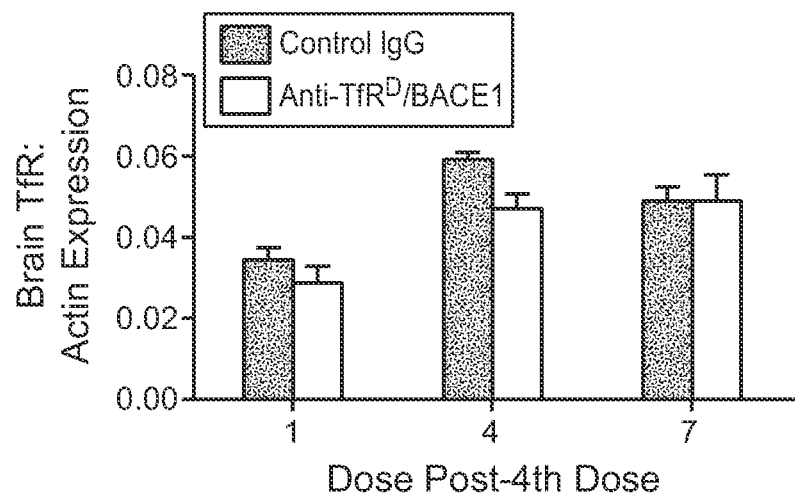

Importantly, no exacerbation of reticulocyte toxicity was observed in the multi-dose context. As shown in FIG. 8E, absolute reticulocyte numbers improved dramatically from 1 day post-second dose to 7 days post-fourth dose (where the values returned to or exceeded control levels). There was no evidence of decreased red cell mass or changes in serum iron and total iron binding capacity (a surrogate parameter for serum transferrin) at four weeks. There was also no evidence of histopathology changes or altered stainable iron levels in any tissues evaluated. Without being bound by theory, it is proposed that an enhanced bone marrow regenerative response elicited by the initial dose administration and sustained throughout the dosing period may be responsible for ameliorating the overall reticulocyte decrease observed after the fourth dose. Additionally, the suspected presence of ADAs further reduced overall circulating antibody levels with repeated dosing, also contributing to the mitigation of reticulocyte depletion observed at week 4. Finally, brain expression of TfR did not differ between anti-TfR$^D$/BACE1 and control IgG treated mice at 1, 4, or 7 days post the fourth dose (FIG. 8F).

Example 6: Impact of Effector-Containing and Effectorless Bispecifics on Erythroid Progenitor Cells in Blood and Bone Marrow Additional experiments were performed to elucidate the impact of antibody dosing on erythroid progenitor cell populations in bone marrow. First, to examine the time course of reticulocyte loss after anti-TfR/BACE1 dosing, blood and bone marrow were isolated at 1, 4, 16, and 24 hours after wild-type mice were intravenously injected with 50 mg/kg of control IgG or anti-TfR$^D$/BACE1 lacking effector function as a single bolus in 200 µL in sterile PBS (n=6/group). Blood and bone marrow were harvested from animals at the indicated time points post-dose. Orbital bleeds were used for blood extraction after isofluorane anesthesia, and bone marrow from one femur was harvested and single cell suspensions were prepared. Cells were then filtered through a 70-micron cell strainer. Cells were washed and resuspended in a set volume of PBS. A fixed volume of cell suspension was added to a fixed concentration of FITC-labeled fluorescent beads and analyzed on a flow cytometer, collecting 5000 bead events per sample to obtain cell counts. Quantitative analysis of erythroid populations was determined by flow cytometry. In both blood and bone marrow, distinct populations of erythroid cells were gated by their expression of the Ter119 marker (a marker that has been determined to be expressed only on murine mature erythrocytes and erythroid precursor cells), TfR expression, and side scatter profile (as previously described in Paniga et al., "Expression of Prion Protein in Mouse Erythroid Progenitors and Differentiating Murine Erythroleukemia Cells." PLoS One 6, 9 (2011); FIGS. 9A and 9B). Briefly, samples were incubated for 20 minutes on ice with anti-mouse Ter119-PE (eBioscience) and biotinylated anti-mouse TfR, followed by streptavidin-eFluor450 (eBioscience). Samples were washed with PBS containing 0.5% BSA, 2 mM EDTA and run on a BD LSR Fortessa multi-color flow cytometer and analyzed using FlowJo software (Ashland, Oreg.).

Figure 9C:
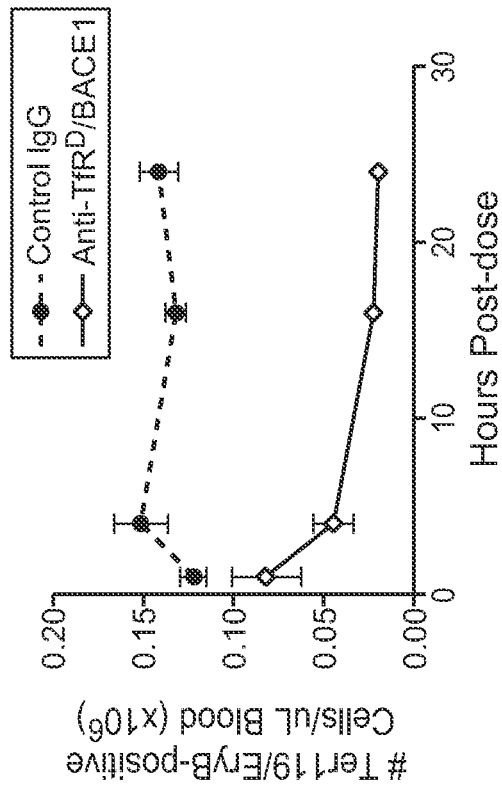
FIGS. 9C and 9D show a time-course of the total Ter119-positive erythroid population (reticulocytes and red blood cells; 9C) and TfR-positive reticulocytes (9D) in blood after dosing with anti-TfR$^D$/BACE1 compared to control IgG (n=6/group).
Figure 9D:
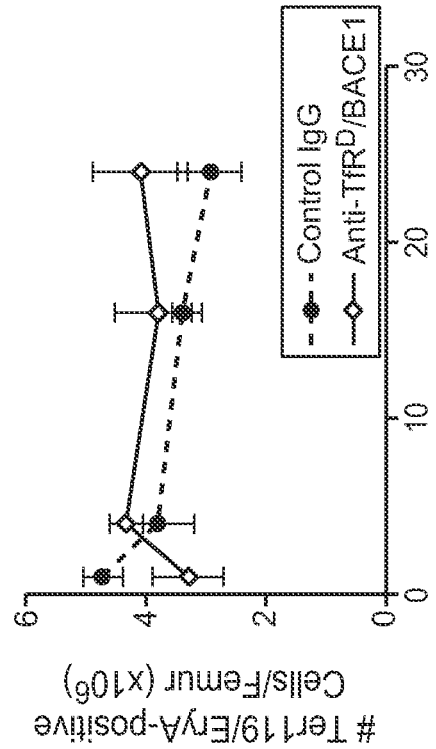
Figure 10A:
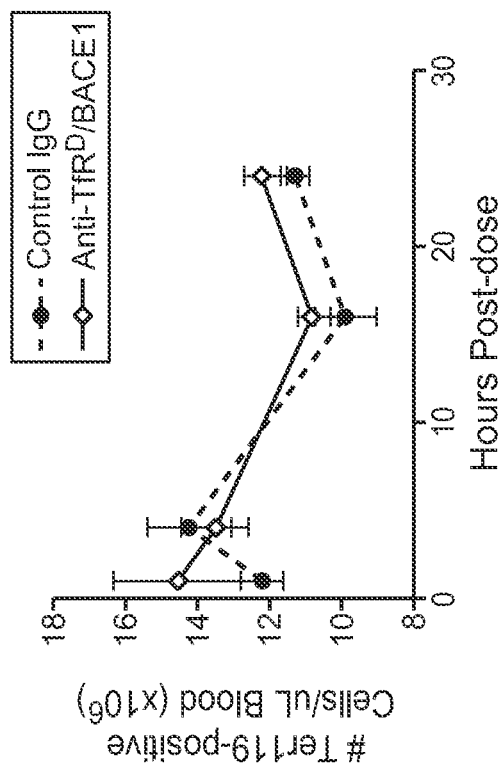
Figure 10B:
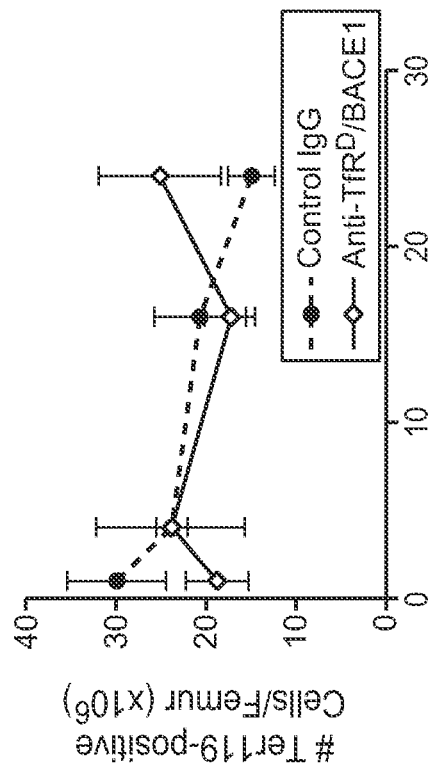
Figure 10C:
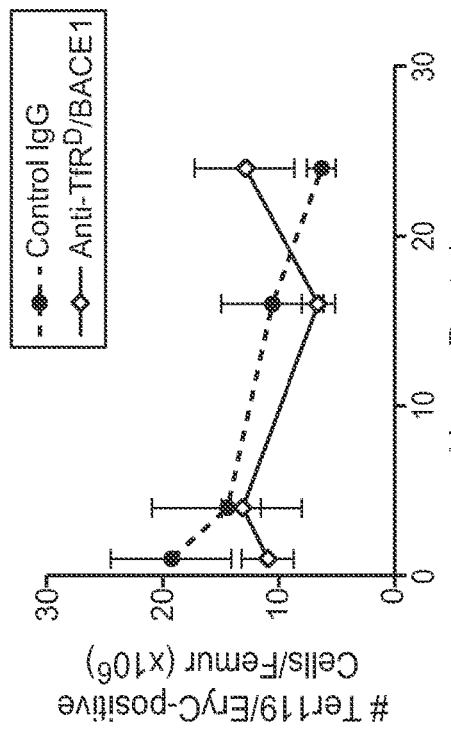
Figure 10D:
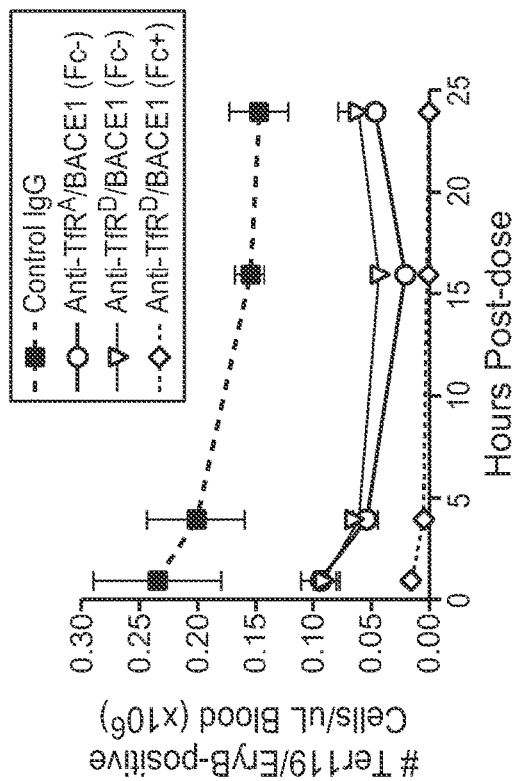

Treatment with anti-TfR$^D$/BACE1 lacking effector function did not alter the total number of erythrocytes in blood compared to control IgG (FIG. 9C), but nonetheless rapidly and significantly reduced circulating TfR-expressing reticulocytes in the blood (FIG. 9D). In contrast to the findings in blood, effectorless anti-TfR$^D$/BACE1 had no effect on any of the erythroid progenitor populations in bone marrow (FIG. 10A-C), including high TfR-expressing populations (EryA and EryB populations) (FIG. 10B-C), and TfR-negative mature erythrocytes (EryC population) (FIG. 10D). Together, these results demonstrated that the effectorless anti-TfR$^D$/BACE1 only depletes TfR-expressing reticulocytes in blood in mice, without impacting other subpopulations of erythroid cells in bone marrow after a single dose.

To investigate the impact of full effector function antibodies on erythrocyte subpopulations in both blood and bone marrow, and to determine whether affinity plays a role in erythroid cell depletion, wild-type mice were given a single IV dose of 25 mg/kg of anti-TfR$^A$/BACE1 (Fc−), anti-TfR$^D$/BACE1 (Fc−), anti-TfR$^D$/BACE1 (Fc+), or control IgG (where "Fc−" indicates an effectorless antibody due to the presence of mutations D265A and N297G or to lack of glycosylation and "Fc+" indicates an antibody with wild-type effector function), following the same injection and sample collection process as above. Neither presence of effector function nor affinity for TfR affected the total number of mature erythrocytes in circulating blood after antibody dosing, compared to control IgG (FIG. 11A). Confirming the previous observation, dosing with effectorless anti-TfR/BACE1 antibodies resulted in a rapid and prolonged decrease in TfR-expressing reticulocytes in blood (FIG. 11B, compare to FIG. 9D). Furthermore, affinity for TfR did not alter the extent to which the bispecific antibodies drove reticulocyte loss, as there were no significant differences in the time course nor magnitude of reticulocyte decrease between animals dosed with anti-TfR$^A$/BACE1 (Fc−) or anti-TfR$^D$/BACE1 (Fc−) (FIG. 11B). However, dosing with full effector function anti-TfR$^D$/BACE1 (Fc+) resulted in a significant exacerbation of reticulocyte loss, as compared with the effectorless bispecific antibodies (FIG. 11B), suggesting that effector function plays an important role in the severity of reticulocyte depletion after antibody dosing.

Figure 12A:
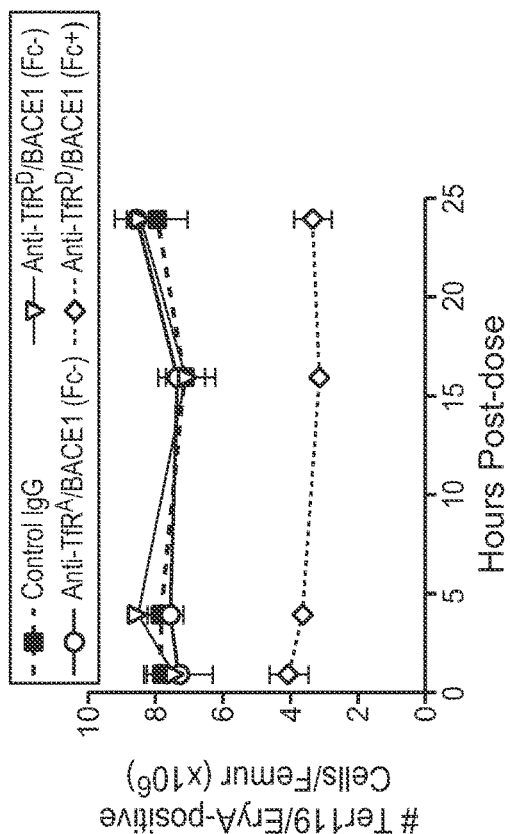
Figure 12B:
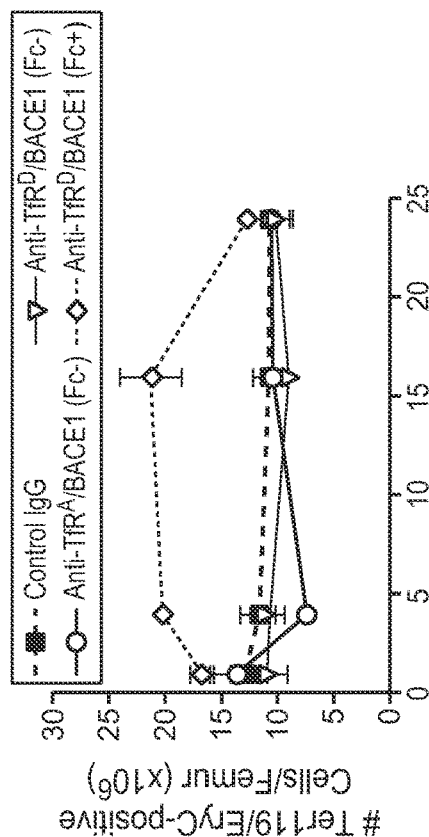
Figure 12C:
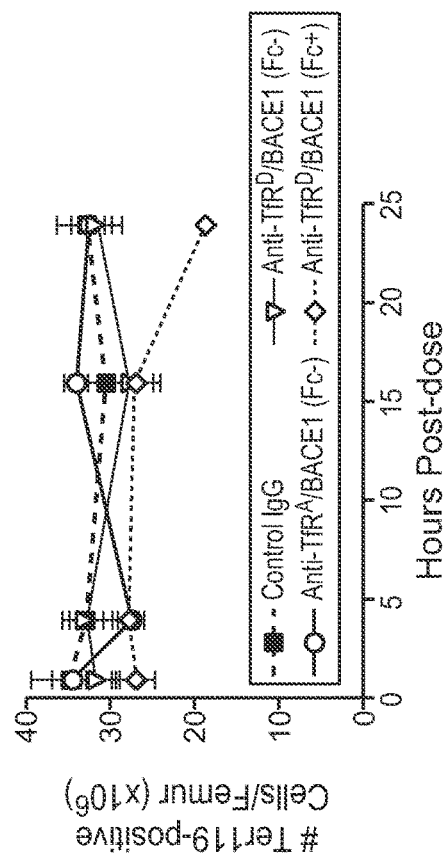
Figure 12D:
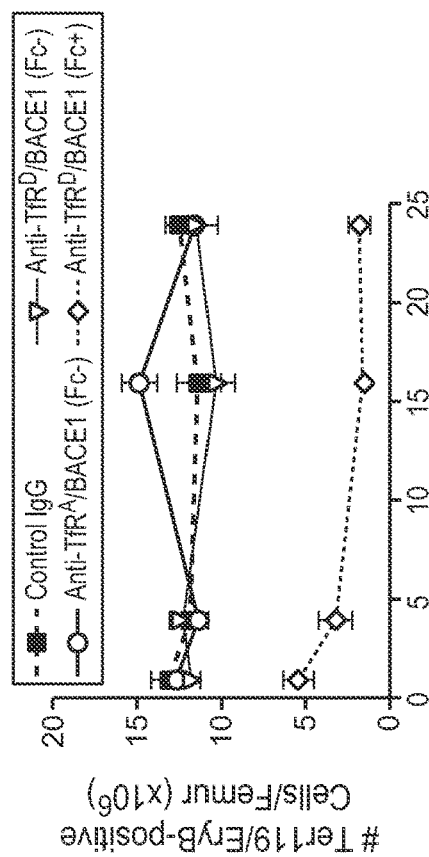

In bone marrow, neither effectorless (Fc−) anti-TfR bispecific antibody altered the total number of erythroid cells, compared to control IgG (FIG. 11A). However, full effector function anti-TfR$^D$/BACE1 (Fc+) reduced the total number of erythroid cells at 24 hrs post dose (FIG. 12A). Specifically, TfR positive erythroid precursor cells (EryA and EryB populations) were significantly and robustly reduced in the presence of a full effector function, while effectorless anti-TfR/BACE1 antibodies had no effect on TfR positive erythroid cell subpopulations compared to control IgG (FIG. 12B-C). Interestingly, the number of mature erythrocytes was transiently increased after dosing with full effector function anti-TfR$^D$/BACE1 (Fc+) at 4 and 16 hours post-dose compared to the effectorless anti-TfR/BACE1 (Fc−) antibodies and control IgG (FIG. 12D). In one nonlimiting interpretation, this transient increase may be due to a secondary compensatory mechanism driving accelerated erythrocyte maturation in response to erythroid precursor cell depletion. Together, these data suggest that an effectorless anti-TfR/BACE1 antibody mitigates TfR-positive erythroid cell loss in bone marrow.

Example 7: Impact of Effector-Containing and Effectorless Monospecific and Bispecific Antibodies on a Human Erythroleukemia Cell Line and Primary Bone Marrow Mononuclear Cells The foregoing examples used anti-murine TfR antibodies, which do not specifically recognize human TfR. To ascertain whether the reticulocyte depletion observed in the mouse studies was unique to a murine system, further experiments were performed utilizing anti-TfR that bind to human TfR.

Figure 13A:
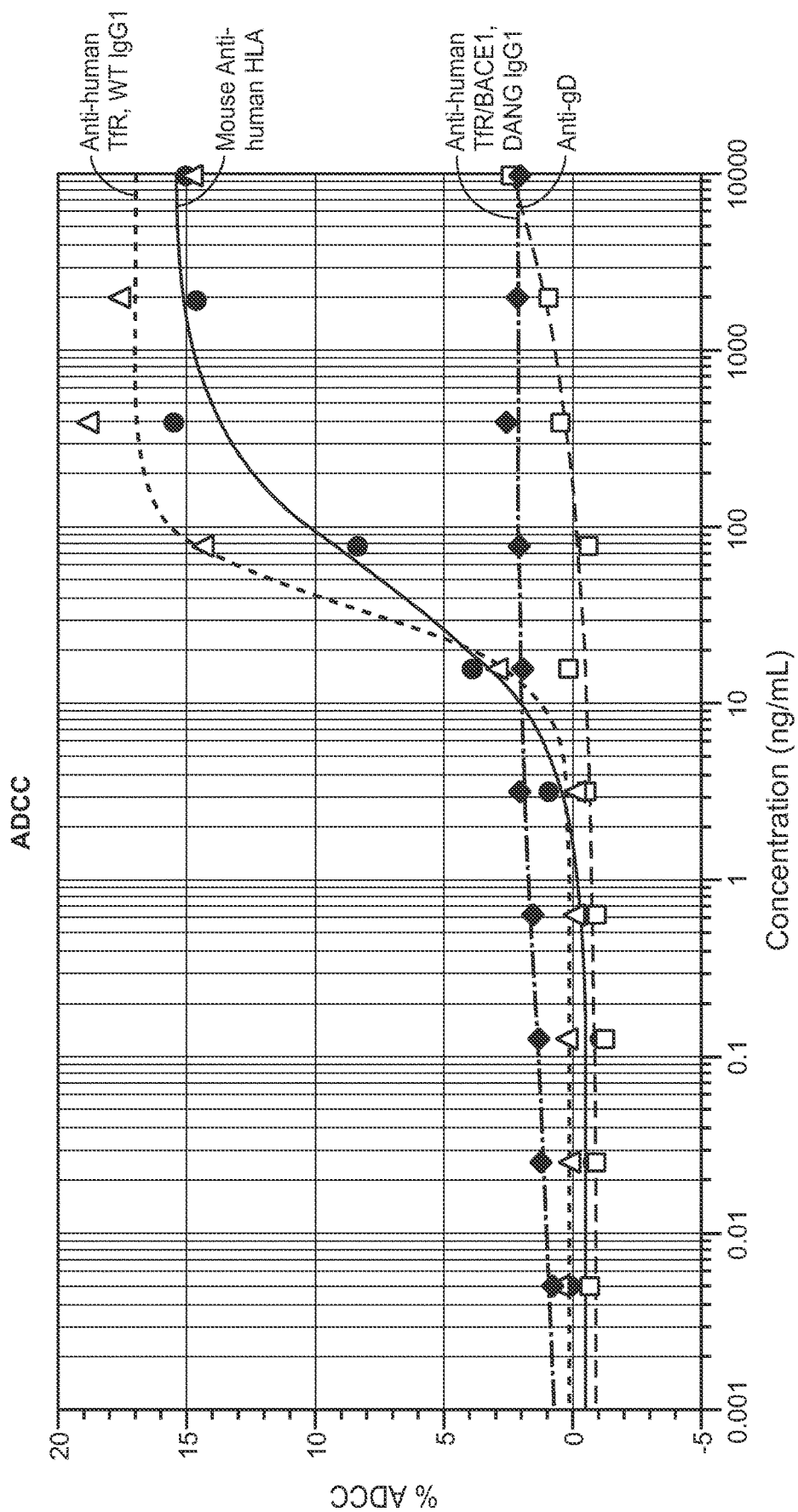
FIGS. 13A-B and FIGS. 14A-B depict the results of experiments assessing the impact of effector function status on ADCC activity of anti-human TfR ("anti-hTFR") antibodies in a human erythroblast cell line or primary human bone marrow mononuclear cells, as described in Example 7.
Figure 13B:
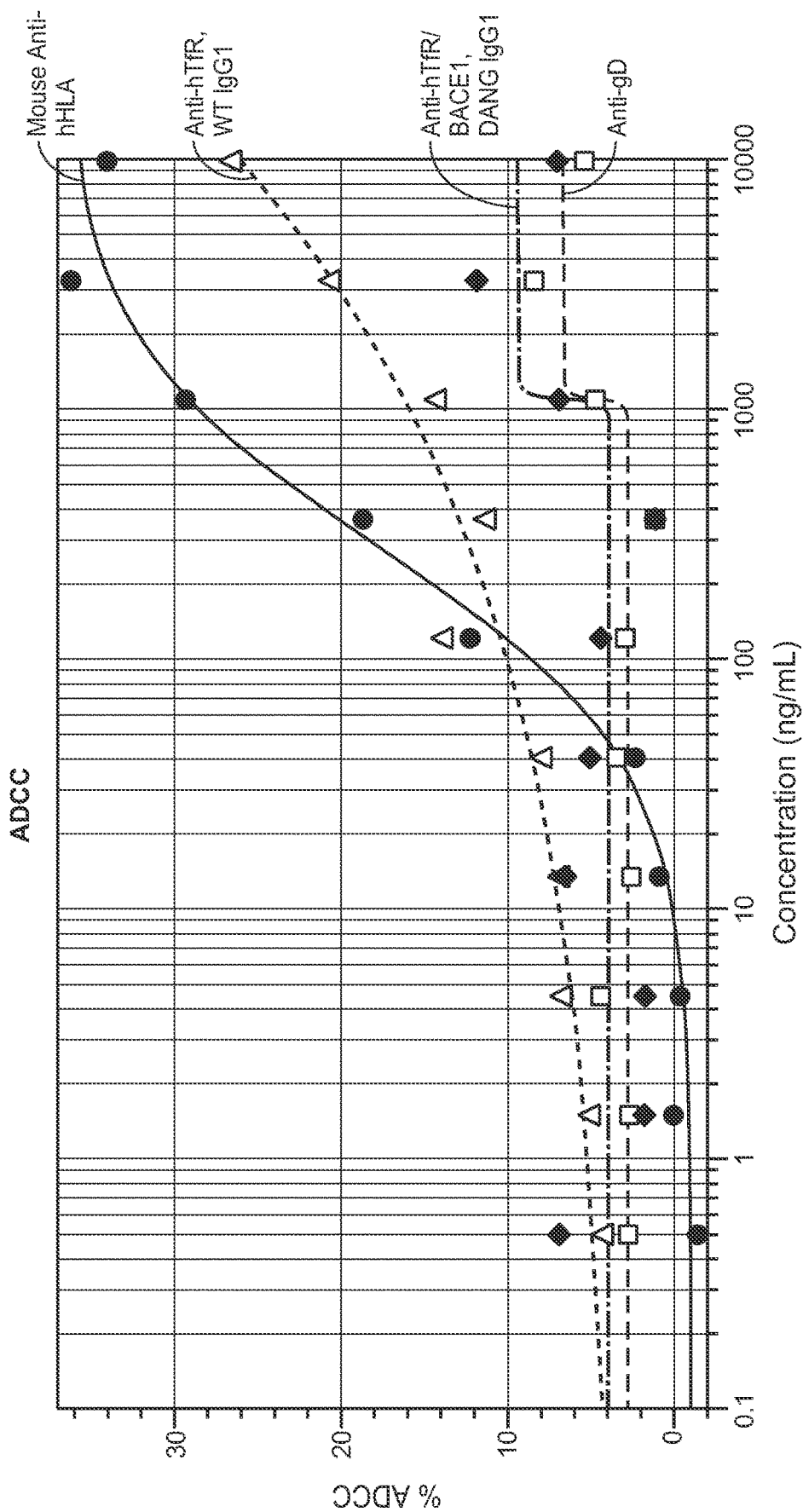

ADCC assays were carried out using peripheral blood mononuclear cells (PBMCs) from healthy human donors as effector cells. A human erythroleukemia cell line (HEL, ATCC) and primary human bone marrow mononuclear cells (AllCells, Inc.) were used as target cells. To minimize inter-donor variability which could potentially arise from allotypic differences at the residue 158 position in FcγRIIIA, blood donors were limited to those carrying the heterozygous RcγRIIIA genotype (FN 158) in the first set of experiments (FIG. 13A-B). For the second set of experiments (FIG. 14A-B), only HEL cells were used as the target cells, with PBMCs from healthy human donors carrying either the FN 158 genotype or the FcγRIIIA V/V158 genotype. The V/V158 genotype was also included in this assay due to the known association with increased NK cell-mediated ADCC activity as well as ability to bind IgG4 antibodies (Bowles and Weiner, 2005; Bruhns et al. 2008). Cells were counted and viability was determined by Vi-CELL® (Beckman Coulter; Fullerton, Calif.) following the manufacturer's instructions.

PBMCs were isolated by density gradient centrifugation using Uni-Sep™ blood separation tubes (Accurate Chemical & Scientific Corp.; Westbury, N.Y.). Target cells in 50 µL of assay medium (RPMI-1640 with 1% BSA and 100 units/mL penicillin and streptomycin) were seeded in a 96-well, round-bottom plate at 4×10$^4$/well. Serial dilutions of test and control antibodies (50 µL/well) were added to the plates containing the target cells, followed by incubation at 37° C. with 5% CO$_2$ for 30 minutes to allow opsonization. The final concentrations of antibodies ranged from 0.0051 to 10,000 ng/mL following 5-fold serial dilutions for a total of 10 data points. After the incubation, 1.0×10$^6$ PBMC effector cells in 100 µL of assay medium were added to each well to give a ratio of 25:1 effector: target cells, and the plates were incubated for an additional 4 hours. The plates were centrifuged at the end of incubation and the supernatants were tested for lactate dehydrogenase (LDH) activity using a Cytotoxicity Detection Kit™ (Roche Applied Scinece; Indianapolis, Ind.). The LDH reaction mixture was added to the supernatants and the plates were incubated at room temperature for 15 minutes with constant shaking. The reaction was terminated with 1 M H$_3$PO$_4$, and absorbance was measured at 490 nm (the background, measured at 650 nm was subtracted for each well) using a SpectraMax Plus microplate reader. Absorbance of wells containing only the target cells served as the control for the background (low control), whereas wells containing target cells lysed with Triton-X100 provided the maximum signal available (high control). Antibody-independent cellular cytotoxicity (AICC) was measured in wells containing target and effector cells without the addition of antibody. The extent of specific ADCC was calculated as follows:

$$\% \; ADCC = 100 \times \frac{A_{490} \; (Sample) - A_{490} \; (AICC)}{A_{490} \; (High \; Control) - A_{490} \; (Low \; Control)}$$

ADCC values of sample dilutions were plotted against the antibody concentration, and the dose-response curves were fitted to a four-parameter model using SoftMax Pro.

In a first set of experiments, the ADCC activity of various anti-human TfR constructs were assessed using either a human erythroleukemia cell line (HEL cells) or primary human bone marrow mononuclear cells as the target cells. Bivalent IgG1 effector function-competent anti-human TfR1 antibody 15G11 and a bispecific form of this antibody with the same anti-BACE1 arm used in the prior examples in a human IgG1 format with the D265A and N297G mutations abrogating effector function (see Example 6) were tested at various concentrations in the ADCC assay, using anti-gD WT IgG1 as a negative control and murine anti-human HLA (class I) as a positive control. The results are shown in FIGS. 13A and 13B. With either the HEL cells as targets (FIG. 13A) or the bone marrow mononuclear cells as targets (FIG. 13B), the monospecific anti-human TfR antibody 15G11 elicited significant ADCC activity. This activity was similar to that of the positive control anti-human HLA antibodies on the HEL cells, and at a robust yet lower level than the positive control on the bone marrow mononuclear cells. The somewhat lower level observed in the bone marrow mononuclear cells experiment is likely due to the fact that only a portion of the heterogenous mixture of myeloid and erythroid lineage PBMC cells used in the experiment express high levels of TfR, whereas the HEL cells have consistently high TfR expression throughout the clonal cell population. In sharp contrast, the bispecific effectorless anti-humanTfR/BACE1 antibody did not display any ADCC activity in either HEL or bone marrow mononuclear cells, similar to the negative control.

Figure 14A:
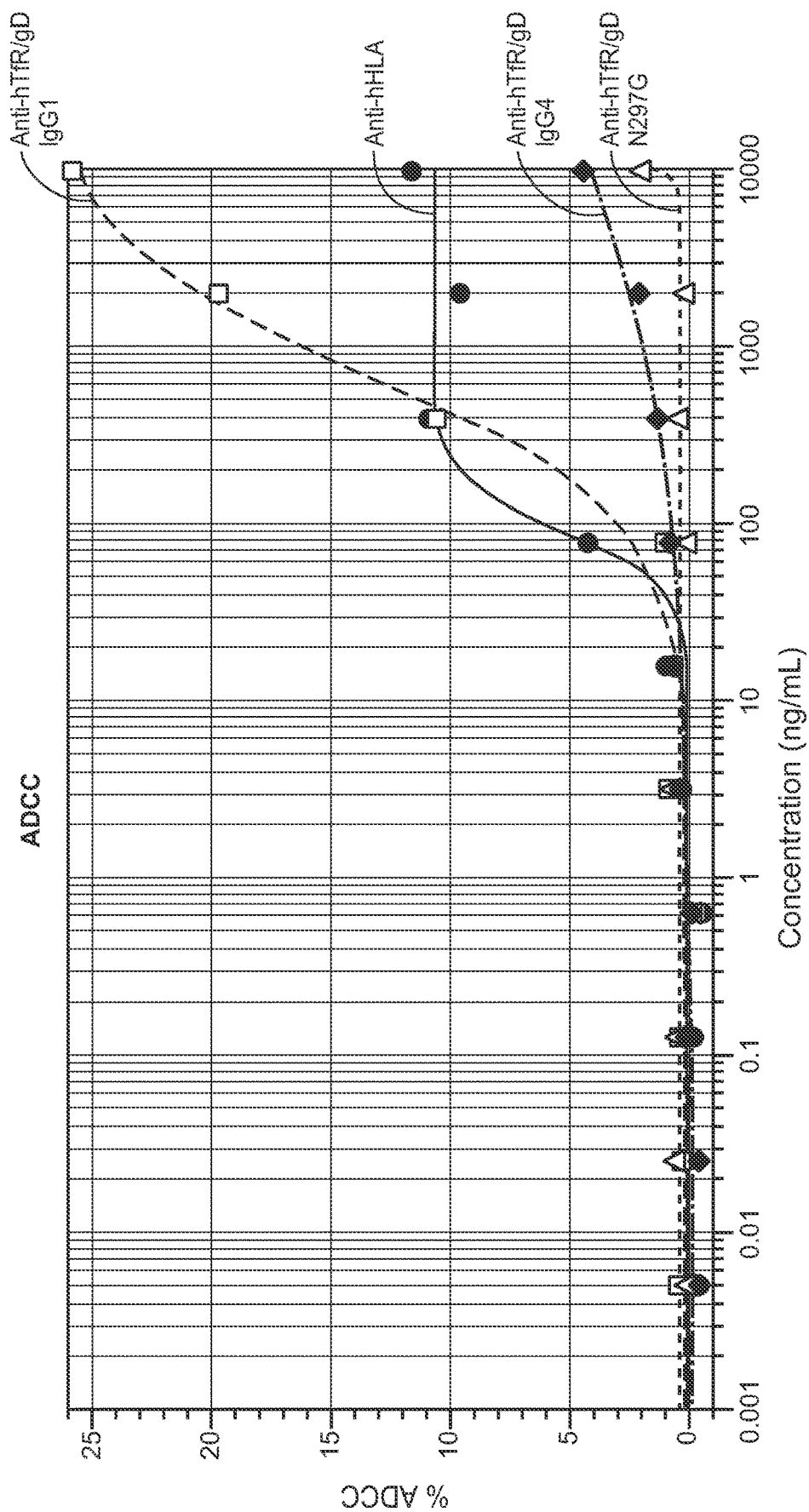
Figure 14B:
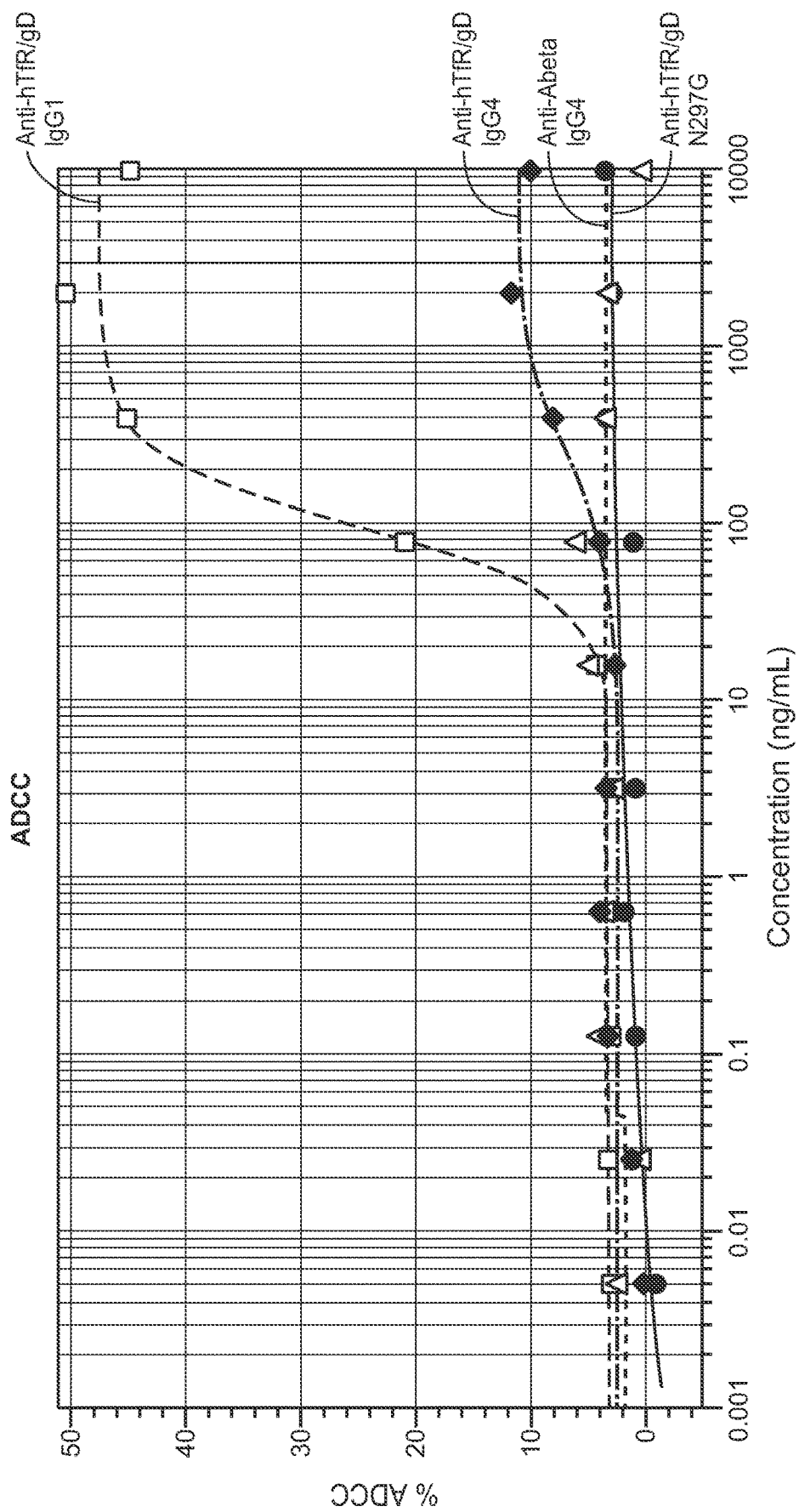

In a second set of experiments, the impact of switching the antibody isotype in this assay system was assessed. The ADCC assay procedure was identical to that described above, with the exception that all target cells were HEL cells, and the effector cells were PBMCs from healthy human donors either carrying the heterozygous FcγRIIIa-V/F158 genotype or the homozygous FcγRIIIa-V/V158 genotype. All anti-human TfR tested were bispecific with anti-gD, with three different Ig backbones: wild-type human IgG1, human IgG1 with the N297G mutation, and human IgG4. An anti-Abeta antibody with a human IgG4 backbone was also tested, and mouse anti-human HLA (class I) served as a positive control. The results are shown in FIGS. 14A and 14B. As anticipated based on the known association between effector cell activation and the V/V158 genotype (Bowles and Weiner 2005), ADCC activity was more robustly elicited by V/V158 donor PBMCs (~45% of target cells impacted) relative to F/V158 donors (~25% of target cells impacted) (compare FIG. 14A to FIG. 14B). Anti-TfR/gD with the wild-type IgG1 induced robust ADCC in HEL cells, while the anti-TfR/gD with the effectorless IgG1 did not show any ADCC activity in HEL cells, replicating the results from the first set of experiments. Notably, at concentrations of 100 ng/mL or higher, anti-TfR/gD of the IgG4 isotype showed a mild ADCC activity. This activity was not observed in the anti-Abeta IgG4 results, indicating that TfR binding was required for the ADCC activity. This finding correlates with previous reports that IgG4 has minimal, but measurable, effector function (Adolffson et al., J. Neurosci. 32(28):9677-9689 (2012); van der Zee et al. Clin Exp. Immunol. 64: 415-422 (1986)); Tao et al., J. Exp. Med. 173:1025-1028 (1991)).

Thus, the findings herein that depletion of erythroid lineage cells in mice occurs in a TfR- and effector-function-dependent manner is directly translatable to the human system. Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. A method of making an antibody useful for transporting a therapeutic compound across the blood-brain barrier with improved safety comprising selecting a first antibody specific for a transferrin receptor (TfR) that has an affinity for the TfR from about 5 nM to about 50 µM, and producing a second antibody which is a version of the first antibody and has an affinity for the TfR from about 5 nM to about 50 µM and comprises at least one of the following constant region modifications: a) an IgG4 isotype; b) a mutation of position 297 of the Fc region of the first antibody such that the wild-type asparagine residue at that position is replaced with alanine in the second antibody; c) a point mutation in the Fc region that impairs binding to one or more Fc receptors at a position selected from the following positions: 238, 239, 248, 249, 252, 254, 265, 268, 269, 270, 272, 278, 289, 292, 293, 294, 295, 296, 298, 301, 303, 322, 324, 327, 329, 333, 338, 340, 373, 376, 382, 388, 389, 414, 416, 419, 434, 435, 437, 438, and 439; d) a point mutation of the Fc region that impairs binding to C1q at a position selected from the following positions: 270, 322, 329, and 321; or e) a point mutation at position 132 of the CH1 domain,
wherein the at least one constant region modification reduces or eliminates the effector function or complement activation function of the second antibody and reduces the impact of the second antibody on reticulocyte levels and/or reduce the severity or presence of acute clinical symptoms in a subject, such that reduction of red blood cell levels in the subject upon second antibody administration is decreased or eliminated compared to the first antibody,
wherein the second antibody is an IgG antibody and comprises an Fc region, and wherein the sequence numbering is according to Kabat sequence numbering.

2. The method of claim 1, comprising coupling the second antibody to the therapeutic compound, and wherein the therapeutic compound is a neurological disorder drug, for use in therapy for a disorder selected from Alzheimer's disease (AD), stroke, dementia, muscular dystrophy (MD), multiple sclerosis (MS), amyotrophic lateral sclerosis (ALS), cystic fibrosis, Angelman's syndrome, Liddle syndrome, Parkinson's disease, Pick's disease, Paget's disease, cancer, and traumatic brain injury.

3. The method of claim 1, wherein the subject is a human.

4. The method of claim 1, wherein the second antibody isotype is an IgG4 isotype.

5. The method of claim 1, wherein the Fc region of the second antibody comprises a mutation at position 297 such that the wild-type asparagine residue at that position is replaced with alanine.

6. The method of claim 1, wherein the second antibody comprises a modification of the Fc region selected from: a point mutation of the Fc region to impair binding to one or more Fc receptors selected from the following positions: 238, 239, 248, 249, 252, 254, 265, 268, 269, 270, 272, 278, 289, 292, 293, 294, 295, 296, 298, 301, 303, 322, 324, 327, 329, 333, 338, 340, 373, 376, 382, 388, 389, 414, 416, 419, 434, 435, 437, 438, and 439; a point mutation of the Fc region to impair binding to C1q selected from the following positions: 270, 322, 329, and 321; or a point mutation at position 132 of the CH1 domain.

7. The method of claim 1, comprising coupling the second antibody to the therapeutic compound, and wherein the therapeutic compound is an imaging agent.

8. The method of claim 1, wherein the second antibody does not impair the binding of the TfR to transferrin.

9. The method of claim 1, wherein the second antibody has an affinity for the TfR from about 30 nM to about 30 µM.

10. The method of claim 1, wherein the second antibody has an affinity for the TfR from about 30 nM to about 1 µM.

11. The method of claim 1, wherein the second antibody has an affinity for the TfR from about 50 nM to about 1 µM.

12. The method of claim 1, wherein the second antibody is a multispecific antibody and the therapeutic compound forms one portion of the multispecific antibody.

13. The method of claim 1, wherein the second antibody comprises a first antigen binding site which binds the TfR and a second antigen binding site which binds a brain antigen.

14. The method of claim 13, wherein the brain antigen is selected from: beta-secretase 1 (BACE1), Abeta, epidermal growth factor receptor (EGFR), human epidermal growth factor receptor 2 (HER2), tau, apolipoprotein E4 (ApoE4), alpha-synuclein, CD20, huntingtin, prion protein (PrP), leucine rich repeat kinase 2 (LRRK2), parkin, presenilin I, presenilin 2, gamma secretase, death receptor 6 (DR6), amyloid precursor protein (APP), p75 neurotrophin receptor (p75NTR), and caspase 6.

15. The method of claim 13, wherein the second antibody binds both TfR and BACE1.

16. The method of claim 13, wherein the second antibody binds both TfR and Abeta.

* * * * *